(12) United States Patent
Felle et al.

(10) Patent No.: US 12,065,652 B2
(45) Date of Patent: Aug. 20, 2024

(54) PROMOTER FOR HETEROLOGOUS EXPRESSION

(71) Applicant: BASF SE, Ludwigshafen (DE)

(72) Inventors: Max Fabian Felle, Ludwigshafen (DE); Bogdan Tokovenko, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 233 days.

(21) Appl. No.: 16/631,999

(22) PCT Filed: Jul. 11, 2018

(86) PCT No.: PCT/EP2018/068847
§ 371 (c)(1),
(2) Date: Jan. 17, 2020

(87) PCT Pub. No.: WO2019/016052
PCT Pub. Date: Jan. 24, 2019

(65) Prior Publication Data
US 2020/0181627 A1   Jun. 11, 2020

(30) Foreign Application Priority Data

Jul. 21, 2017 (EP) .................................... 17182615
Dec. 22, 2017 (EP) .................................... 17209978

(51) Int. Cl.
*C12N 15/70* (2006.01)
*C12N 15/74* (2006.01)

(52) U.S. Cl.
CPC ............. *C12N 15/70* (2013.01); *C12N 15/74* (2013.01); *C12N 2800/101* (2013.01); *C12N 2800/70* (2013.01); *C12N 2830/005* (2013.01); *C12N 2830/34* (2013.01); *C12N 2830/55* (2013.01)

(58) Field of Classification Search
CPC .... C12N 15/70; C12N 15/74; C12N 2800/70; C12N 2830/34; C12N 2830/55
See application file for complete search history.

(56) References Cited

U.S. PATENT DOCUMENTS 7,247,450 B2 * 7/2007 Ferrari .................... C07K 14/32
435/6.15
2006/0057674 A1 * 3/2006 Hintz ....................... C12N 9/14
435/183

FOREIGN PATENT DOCUMENTS

WO    WO-2004/078953 A1    9/2004

OTHER PUBLICATIONS

Herbort et al. 1999 (Temporal Expression of the Bacillus subtilis secA gene, encoding a central component of the preprotein translocase; Journal of bacteriology, American Society for Microbiology 181(2): 493-500) (Year: 1999).*
Rosano et al. 2014 (Recombinant protein expression in *Escherichia coli*: advances and challenges; Frontiers in Microbiology; 5(171): 1-17). (Year: 2014).*
Limia et al. 2001 (Characterization and expression of secA in *Mycobacterium avium*; FEMS Microbiology Letters: 151-157) (Year: 2001).*
Kakeshtia et al. 2010 (Enhanced extracellular production of heterologous proteins in Bacillus subtilis by deleting the C-terminal Region of the SecA secretory Machinery; Mol Biotechnol 46:250-257) (Year: 2010).*
Whisstock et al., (Quarterly Reviews of Biophysics 2003, vol. 36 (3): 307-340,).*
Witowski et al., (Biochemistry 38:11643-11650, 1999).*
Kisselev L., (Structure, 2002, vol. 10: 8-9.*
Devos et al., (Proteins: Structure, Function and Genetics, 2000, vol. 41: 98-107).*
Braunstein et al., Two nonredundant SecA homologues function in mycobacteria, J. Bacteriol., 183(24):6979-90 (Dec. 2001).
Feltcher et al., Emerging themes in SecA2-mediated protein export, Nat. Rev. Microbiol., 10(11):779-89 (Nov. 2012).
Green et al., Bacterial Secretion Systems—an Overview, Microbiology Spectrum 4.1 (2016).
Herbort et al., Temporal expression of the Bacillus subtilis secA gene, encoding a central component of the preprotein translocase, J. Bacteriol., 181(2):493-500 (Jan. 1999).
International Application No. PCT/EP2018/068847, International Search Report and Written Opinion, mailed Dec. 7, 2018.
Limia et al., Characterization and expression of secA in *Mycobacterium avium*, FEMS Microbiol. Lett., 197(2):151-7 (Apr. 2001).
Lubys et al., Cloning and analysis of the plasmid-borne genes encoding the Bsp6I restriction and modification enzymes, Gene, 157(1-2):25-9 (May 1995).
Madsen et al., Cloning and characterization of the lactococcal plasmid-encoded type II restriction/modification system, LlaDII, Appl. Environ. Microbiol., 64(7):2424-31 (Jul. 1998).

(Continued)

*Primary Examiner* — Jennifer E Graser

(74) *Attorney, Agent, or Firm* — MARSHALL, GERSTEIN & BORUN LLP

(57) ABSTRACT

The present invention is directed to a nucleic acid construct comprising a polynucleotide operably linked to one or more control sequence that directs the expression of the polynucleotide in a host cell, wherein at least one control sequence comprises a promoter sequence of an operon comprising a secA gene or a functional fragment or functional variant thereof and wherein said promoter sequence is heterologous to the polynucleotide. In a further embodiment, the invention is directed to an expression vector and a host cell comprising the nucleic acid construct comprising the promoter sequence described herein and a method of expressing a polynucleotide in a host cell.

9 Claims, 5 Drawing Sheets

Specification includes a Sequence Listing.

(56) References Cited

OTHER PUBLICATIONS

Pfeiffer et al., Isolation and characterization of DNA cytosine 5-methyltransferase from human placenta, Biochim. Biophys. Acta, 740(3):323-30 (Aug. 1983).
"Bacillus subtilis gene for secA protein", Database EMBL[Online], XP002778221, retrieved from STN EBI accession No. EM_STD:D10279, May 15, 1992, 2 pages.
"Bacillus subtilis secA gene sequence SEQ: 1", Database Genesq [Online], XP002778220, retrieved from EBI accession No. GSN:AYG93130, Sep. 30, 2020, 1 page.
European Search Report for EP Patent Application No. 17182615.9, Issued on Dec. 22, 2017, 3 pages.
European Search Report for EP Patent Application No. 17209978.0, Issued on Jun. 14, 2018, 3 pages.
Roth et al., Functional Roles of Conserved Amino Acid Residues in DNA Methyltransferases Investigated by Site-directed Mutagenesis of the EcoRV Adenine-$N^6$-methyltransferase, J. Biol. Chem., 273(28):17333-17342 (1998).

* cited by examiner

PROMOTER FOR HETEROLOGOUS EXPRESSION

This application is a National Stage application of International Application No. PCT/EP2018/068847, filed Jul. 11, 2018, which claims priority to European Patent Application No. 17182615.9, filed Jul. 21, 2017 and European Patent Application No. 17209978.0, filed Dec. 22, 2017.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "170813_Seqlisting.txt", which was created on Dec. 10, 2019 and is 147,297 bytes in size. The subject matter of the Sequence Listing is incorporated herein in its entirety by reference.

FIELD OF THE INVENTION

The present invention relates to a nucleic acid construct comprising a promoter sequence of an operon comprising a secA gene or a functional fragment or functional variant thereof, which is suitable for driving expression of heterologous polynucleotides. Moreover, the present invention relates to an expression vector and a host cell comprising said nucleic acid construct and methods for expressing polynucleotides using the promoter sequence.

BACKGROUND OF THE INVENTION

Microorganisms are nowadays widely applied in industry by making use of their fermentation capacity. Microorganisms are particularly used as a host for fermentative production of a variety of substances such as enzymes, proteins, chemicals, sugars and polymers. For these purposes, microorganisms are subject of genetic engineering in order to adapt their gene expression to the demands of the specific production process.

A key element to drive gene expression in a host cell is the promoter sequence. For gene expression to take place, the RNA polymerase must attach to the promoter sequence near a gene. Thus, promoters contain specific DNA sequences that provide a binding site for RNA polymerase and also for other proteins that recruit RNA polymerase to the recognition sequence (i.e., transcription factors). In bacteria, the promoter is usually recognized by the RNA polymerase and an associated sigma factor, which are guided to the promoter DNA by an activator protein's binding to its own DNA binding site nearby. In eukaryotes, the process is more complicated, and various factors are necessary for the binding of an RNA polymerase to the promoter. Influenced by the nucleic acid sequence, promoters can confer low, moderate or high expression levels and can be constitutive or inducible.

Due to their central role in gene expression, there is a constant need for novel sequences that are suitable as a promoter for the expression of transgenes in a host cell under specific conditions.

In particular, for transgene products, which are not tolerated by the host cell in high amounts, promoter sequences that provide a moderate expression level are needed. Examples of such transgene products are components of the restriction modification system, like restriction endonucleases and methyltransferases, recombinases, and proteins conferring antibiotic resistance.

The present inventors have found that using a secA promoter for the expression of a transgene in a host cell greatly improves expression results, in particular if moderate expression levels of the transgene are desired.

BRIEF SUMMARY OF THE INVENTION

The present invention is directed to a particular type of promoter sequences and nucleic acid constructs comprising such promoter sequences.

Specifically, the present invention is directed to a nucleic acid construct comprising a polynucleotide operably linked to one or more control sequence that directs the expression of the polynucleotide in a host cell, wherein at least one control sequence comprises a promoter sequence of an operon comprising a secA gene or a functional fragment or functional variant of the promoter sequence and wherein said promoter sequence is heterologous to the polynucleotide.

In one embodiment, the promoter sequence comprises the consensus sequence TKNTTTGGAAATN(8-12)RTRTGN-TAWRATAWN(4-6)(SEQ ID NO: 117) immediately followed by a transcription start site.

In another embodiment, the promoter sequence comprises the consensus sequence TCAWTMNTGCTGYN(11-13) TTAATGRTAADATTYDTN(4-5)(SEQ ID NO: 118) immediately followed by a transcription start site.

In a further embodiment, the invention is directed to an expression vector and a host cell comprising the nucleic acid construct comprising the promoter sequence described herein.

Another embodiment of the present invention is a method of expressing a polynucleotide, comprising the steps of (a) providing a host cell comprising a heterologous nucleic acid construct comprising a promoter as described herein; (b) cultivating the recombinant host cell of step (a) under conditions conductive for the expression of the polynucleotide; and (c) optionally, recovering a protein of interest encoded by the polynucleotide.

The promoter sequence described herein is particularly useful for the expression of polynucleotides which require a moderate expression level in a host cell.

(M.Ckr1771II)), 2z6u_A (used for SEQ ID NO: 40 (M.CmaLM2II)) and 9mht_C (used for SEQ ID NO: 42 (M.Fsp4HI)). Predicted structures were structurally aligned to the predicted structure of SEQ ID NO: 33 (M.Fnu4HI) with TMalign, version 20160521 (Y. Zhang, J. Skolnick (2005), TM-align: A protein structure alignment algorithm based on TM-score, Nucleic Acids Research, 33: 2302-2309) using the default parameters. Pairwise structural alignments were combined into a multiple sequence alignment using MAFFT, version 7.221 (Katoh, S. (2013) MAFFT multiple sequence alignment software version 7: improvements in performance and usability. Molecular Biology and Evolution 30:772-780) using default parameters of the merge mode. Secondary structure annotation was added to the figure as a consensus of structural predictions. Important conserved positions are highlighted as grey columns and identified by greek letters.

Figure 2:
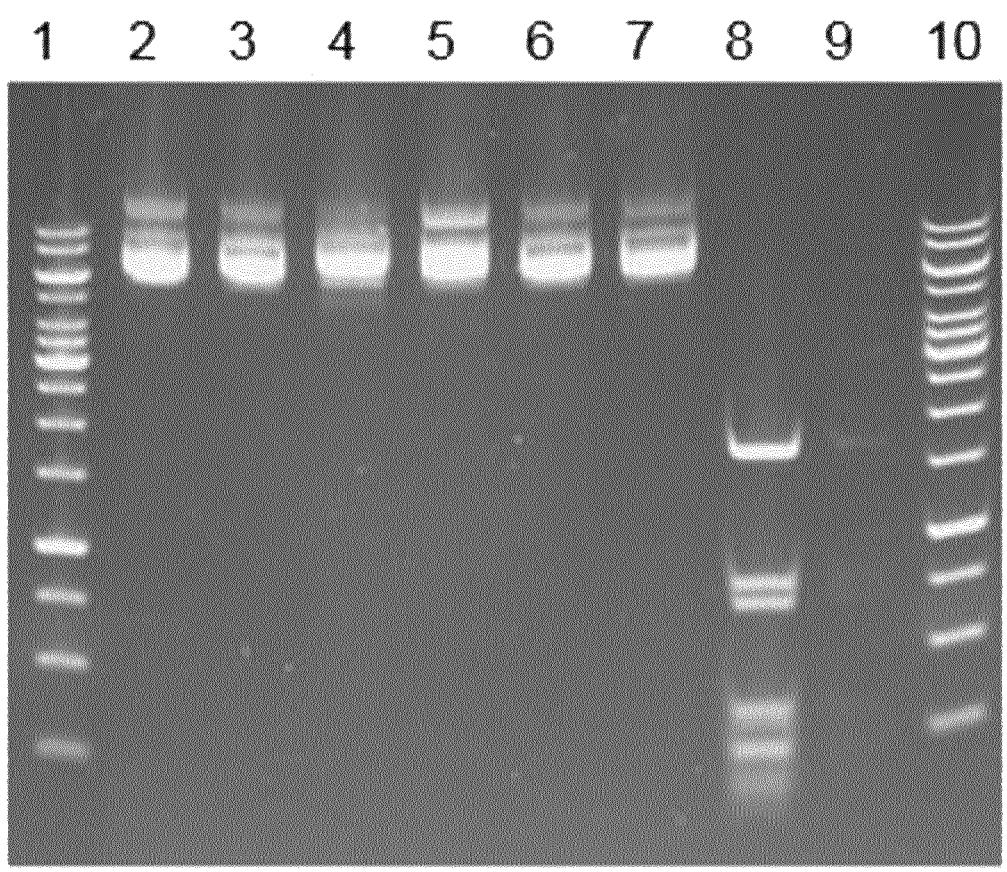

FIG. 2 shows a 0.8% agarose gel of a SatI restriction digests of plasmids isolated from different MTase containing E. coli strains (Example 1). Lane 1: DNA marker-Generuler 1 kb DNA Ladder (ThermoFisher Scientific). Lane 2: Ec #83, Lane 3: Ec #84, Lane 4: Ec #85, Lane 5: Ec #86, Lane 6: Ec #87, Lane 7: Ec #88. Lane 8: Ec #82. Lane 10: DNA marker.

Figure 3:
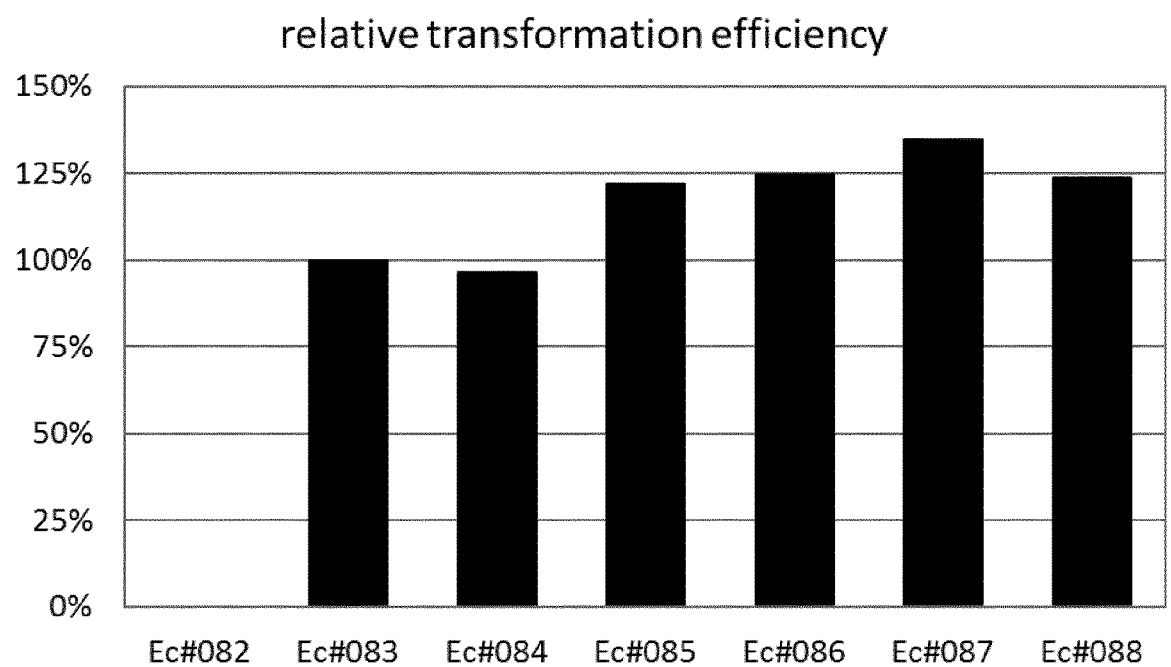

FIG. 3 shows the relative transformation efficiencies into B. licheniformis ATCC 53926 cells of plasmid DNA isolated from different E. coli strains as described in Example 2. The E. coli strain Ec #083 carries the B. licheniformis ATCC 53926 DNA methyltransferase and was set to 100%. The E. coli strain Ec #084 carries a codon-optimized variant of the B. licheniformis ATCC 53926 DNA methyltransferase and serves as control for gene expression. Plasmid DNA from E. coli Ec #082 which was not methylated by a GCNGC specific DNA methyltransferase did not recover any transformants. Plasmid DNA isolated from E. coli strains carrying MTases having a similar structure and being heterologous to B. licheniformis ATCC 53926 (Ec #85-87) transformed into B. licheniformis ATCC 53926 resulted in significantly increased transformation efficiencies. Plasmid DNA isolated from the E. coli strain carrying the homologous MTase (Ec #88) of B. licheniformis ATCC 53926 with a deletion of amino acids 103-108 from SEQ ID NO: 34 (6 amino acids were truncated in total, resulting in SEQ ID NO: 35) also resulted in a significantly increased transformation efficiency compared to Ec #83.

Figure 4:
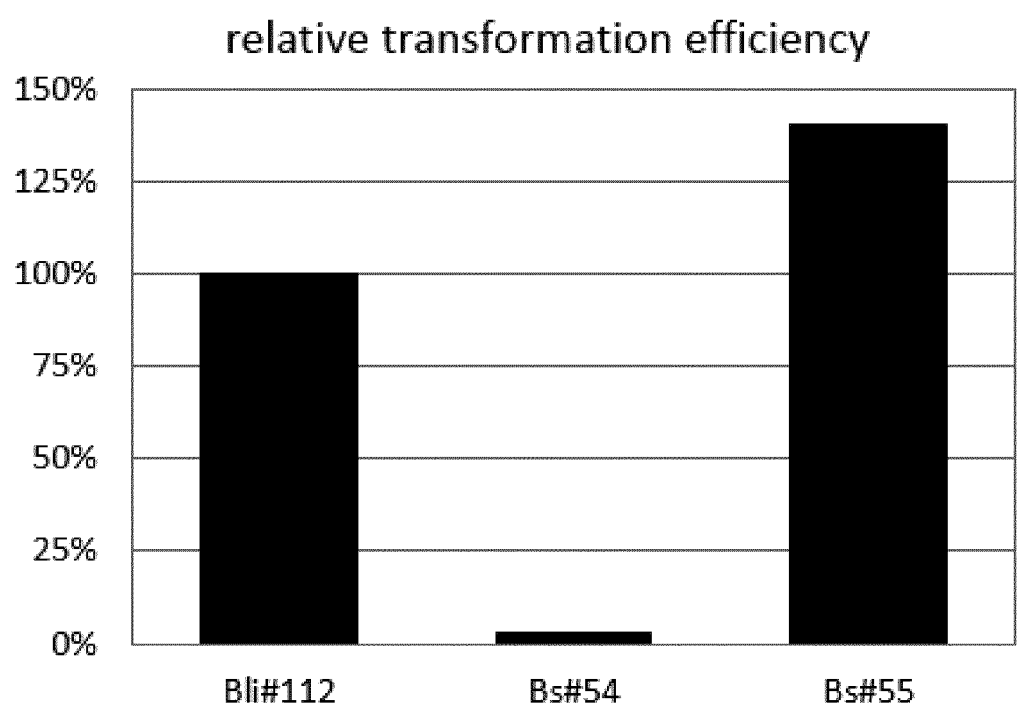

FIG. 4 shows the relative transformation efficiencies into B. licheniformis ATCC 53926 cells of pUK56 plasmid DNA isolated from B. subtilis Bs #54 and Bs #55 strains as described in Example 3. The transformation efficiency of pUK56 plasmid DNA isolated from B. licheniformis Bli #112, carrying the B. licheniformis ATCC 53926 DNA methylation pattern, was set to 100%.

Figure 5:
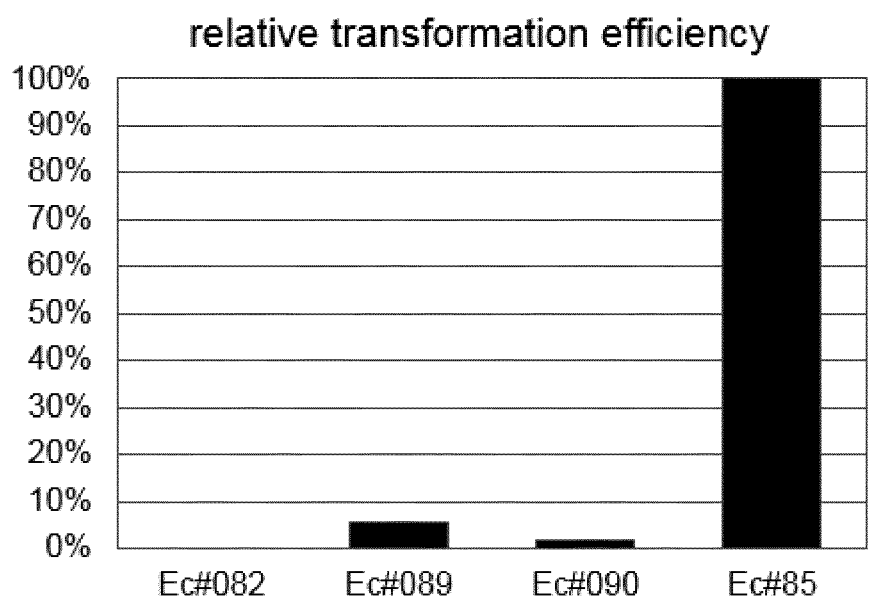

FIG. 5 shows the relative transformation efficiencies into B. licheniformis ATCC 53926 cells of plasmid DNA comprising different promoters isolated from different E. coli strains as described in Example 3. The transformation efficiency of plasmid DNA from E. coli strain Ec #85 was set to 100%. The constructs comprising SecA promoters yielded the highest transformation efficiency.

DETAILED DESCRIPTION OF THE INVENTION

The present invention may be understood more readily by reference to the following detailed description of the embodiments of the invention and the examples included herein.

Definitions

Unless otherwise noted, the terms used herein are to be understood according to conventional usage by those of ordinary skill in the relevant art.

It is to be understood that as used in the specification and in the claims, "a" or "an" can mean one or more, depending on the context in which it is used. Thus, reference to "a cell" can mean that at least one cell can be utilized.

Throughout this application, various publications are referenced. The disclosures of all of these publications and those references cited within those publications in their entireties are hereby incorporated by reference into this application in order to more fully describe the state of the art to which this invention pertains.

"Parent" sequence (e.g., "parent enzyme" or "parent protein") is the starting sequences for introduction of changes (e.g. by introducing one or more amino acid substitutions) of the sequence resulting in "variants" of the parent sequences. Thus, the term "enzyme variant" or "sequence variant" or "protein variant" are used in reference to parent enzymes that are the origin for the respective variant enzymes. Therefore, parent enzymes include wild type enzymes and variants of wild-type enzymes which are used for development of further variants.

Variant enzymes differ from parent enzymes in their amino acid sequence to a certain extent; however, variants at least maintain the enzyme properties of the respective parent enzyme. In one embodiment, enzyme properties are improved in variant enzymes when compared to the respective parent enzyme. In one embodiment, variant enzymes have at least the same enzymatic activity when compared to the respective parent enzyme or variant enzymes have increased enzymatic activity when compared to the respective parent enzyme.

When describing protein variants, the standard IUPAC single-letter or three-letter amino acid abbreviations are used.

"Substitutions" are described by providing the original amino acid followed by the number of the position within the amino acid sequence, followed by the substituted amino acid. For example, the substitution of histidine at position 120 with alanine is designated as "His120Ala" or "H120A".

"Deletions" are described by providing the original amino acid followed by the number of the position within the amino acid sequence, followed by *. Accordingly, the deletion of glycine at position 150 is designated as "Gly150*" or G150*". Alternatively, deletions are indicated by e.g. "deletion of D183 and G184".

"Insertions" are described by providing the original amino acid followed by the number of the position within the amino acid sequence, followed by the original amino acid and the additional amino acid. For example, an insertion at position 180 of lysine next to glycine is designated as "Gly180GlyLys" or "G180GK". When more than one amino acid residue is inserted, such as e.g. a Lys and Ala after Gly180 this may be indicated as: Gly180GlyLysAla or G195GKA.

In cases where a substitution and an insertion occur at the same position, this may be indicated as S99SD+S99A or in short S99AD. In cases where an amino acid residue identical to the existing amino acid residue is inserted, it is clear that degeneracy in the nomenclature arises. If for example a glycine is inserted after the glycine in the above example this would be indicated by G180GG. Variants comprising multiple alterations are separated by "+", e.g., "Arg170Tyr+Gly195Glu" or "R170Y+G195E" representing a substitution of arginine and glycine at positions 170 and 195 with tyrosine and glutamic acid, respectively. Alternatively, multiple alterations may be separated by space or a comma e.g. R170Y G195E or R170Y, G195E respectively. Where different alterations can be introduced at a position, the different alterations are separated by a comma, e.g. "Arg170Tyr, Glu" and R170T, E, respectively, represents a substitution of arginine at position 170 with tyrosine or glutamic acid. Alternatively, different alterations or optional substitutions may be indicated in brackets, e.g., Arg170[Tyr, Gly] or Arg170{Tyr, Gly} or in short R170 [Y, G] or R170 {Y, G}.

The numbering of the amino acid residues of the DNA methyltransferase described herein is according to the numbering of the Fnu4HI DNA methyltransferase from *Fusobacterium* nucleatum 4H1 as shown in SEQ ID NO: 33 (i.e., according to the numbering of SEQ ID NO: 33).

For nucleotide sequences, e.g., consensus sequences, an IUPAC nucleotide nomenclature (Nomenclature Committee of the International Union of Biochemistry (NC-IUB) (1984). "Nomenclature for Incompletely Specified Bases in Nucleic Acid Sequences") is used, with the following nucleotide and nucleotide ambiguity definitions, relevant to this invention: A, adenine; C, cytosine; G, guanine; T, thymine; K, guanine or thymine; R, adenine or guanine; W, adenine or thymine; M, adenine or cythosine; Y, cythosine or thymine; D, not a cythosine; N, any nucleotide.

In addition, notation "N(3-5)" means that indicated consensus position may have 3 to 5 any (N) nucleotides. For example, a consensus sequence "AWN(4-6)" represents 3 possible variants—with 4, 5, or 6 any nucleotides at the end: AWNNNN, AWNNNNN, AWNNNNNN.

Variants of the parent enzyme molecules may have an amino acid sequence which is at least n percent identical to the amino acid sequence of the respective parent enzyme having enzymatic activity with n being an integer between 50 and 100, preferably 50, 55, 60, 65, 70, 75, 80, 85, 90, 91, 92, 93, 94, 95, 96, 97, 98 or 99 compared to the full length polypeptide sequence. Variant enzymes described herein which are n percent identical when compared to a parent enzyme, have enzymatic activity.

Enzyme variants may be defined by their sequence identity when compared to a parent enzyme. Sequence identity usually is provided as "% sequence identity" or "% identity". To determine the percent-identity between two amino acid sequences in a first step a pairwise sequence alignment is generated between those two sequences, wherein the two sequences are aligned over their complete length (i.e., a pairwise global alignment). The alignment is generated with a program implementing the Needleman and Wunsch algorithm (J. Mol. Biol. (1979) 48, p. 443-453), preferably by using the program "NEEDLE" (The European Molecular Biology Open Software Suite (EMBOSS)) with the programs default parameters (gapopen=10.0, gapextend=0.5 and matrix=EBLOSUM62). The preferred alignment for the purpose of this invention is that alignment, from which the highest sequence identity can be determined.

After aligning the two sequences, in a second step, an identity value shall be determined from the alignment. Therefore, according to the present invention the following calculation of percent-identity applies:

%-identity=(identical residues/length of the alignment region which is showing the respective sequence of this invention over its complete length)*100. Thus sequence identity in relation to comparison of two amino acid sequences according to this embodiment is calculated by dividing the number of identical residues by the length of the alignment region which is showing the respective sequence of this invention over its complete length. This value is multiplied with 100 to give "%-identity".

For calculating the percent identity of two DNA sequences the same applies as for the calculation of percent identity of two amino acid sequences with some specifications. For DNA sequences encoding for a protein the pairwise alignment shall be made over the complete length of the coding region from start to stop codon excluding introns. For non-protein-coding DNA sequences the pairwise alignment shall be made over the complete length of the sequence of this invention, so the complete sequence of this invention is compared to another sequence, or regions out of another sequence. Moreover, the preferred alignment program implementing the Needleman and Wunsch algorithm (J. Mol. Biol. (1979) 48, p. 443-453) is "NEEDLE" (The European Molecular Biology Open Software Suite (EMBOSS)) with the programs default parameters (gapopen=10.0, gapextend=0.5 and matrix=EDNAFULL).

The following example is meant to illustrate the embodiments of the invention, which is on two nucleotide sequences, but same calculations apply to protein sequences:

```
Seq A: AAGATACTG length: 9 bases
Seq B: GATCTGA   length: 7 bases
```

Hence, the shorter sequence is sequence B.

Producing a pairwise global alignment which is showing both sequences over their complete lengths results in

```
Seq A: AAGATACTG-
          ||| |||
Seq B: --GAT-CTGA
```

The "I" symbol in the alignment indicates identical residues (which means bases for DNA or amino acids for proteins). The number of identical residues is 6.

The "−" symbol in the alignment indicates gaps. The number of gaps introduced by alignment within the Seq B is 1. The number of gaps introduced by alignment at borders of Seq B is 2, and at borders of Seq A is 1.

The alignment length showing the aligned sequences over their complete length is 10.

Producing a pairwise alignment which is showing the shorter sequence over its complete length according to the invention consequently results in:

```
Seq A: GATACTG-
       ||| |||
Seq B: GAT-CTGA
```

Producing a pairwise alignment which is showing sequence A over its complete length according to the invention consequently results in:

```
Seq A: AAGATACTG
          ||| |||
Seq B: --GAT-CTG
```

Producing a pairwise alignment which is showing sequence B over its complete length according to the invention consequently results in:

```
Seq A: GATACTG-
       ||| |||
Seq B: GAT-CTGA
```

The alignment length showing the shorter sequence over its complete length is 8 (one gap is present which is factored in the alignment length of the shorter sequence).

Accordingly, the alignment length showing Seq A over its complete length would be 9 (meaning Seq A is the sequence of the invention).

Accordingly, the alignment length showing Seq B over its complete length would be 8 (meaning Seq B is the sequence of the invention).

According to the example provided above, %-identity is: for Seq A being the sequence of the invention (6/9) *100=66.7%; for Seq B being the sequence of the invention (6/8)*100=75%.

Enzyme variants may be defined by their sequence similarity when compared to a parent enzyme. Sequence similarity usually is provided as "% sequence similarity" or "%-similarity". For calculating sequence similarity in a first step a sequence alignment has to be generated as described above. In a second step, the percent-similarity has to be calculated, whereas percent sequence similarity takes into account that defined sets of amino acids share similar properties, e.g., by their size, by their hydrophobicity, by their charge, or by other characteristics. Herein, the exchange of one amino acid with a similar amino acid is referred to as "conservative mutation". Enzyme variants comprising conservative mutations appear to have a minimal effect on protein folding resulting in certain enzyme properties being substantially maintained when compared to the enzyme properties of the parent enzyme.

For determination of %-similarity according to this invention the following applies, which is also in accordance with the BLOSUM62 matrix, which is one of the most used amino acids similarity matrix for database searching and sequence alignments Amino acid A is similar to amino acids S
Amino acid D is similar to amino acids E; N
Amino acid E is similar to amino acids D; K; Q
Amino acid F is similar to amino acids W; Y
Amino acid H is similar to amino acids N; Y
Amino acid I is similar to amino acids L; M; V
Amino acid K is similar to amino acids E; Q; R
Amino acid L is similar to amino acids I; M; V
Amino acid M is similar to amino acids I; L; V
Amino acid N is similar to amino acids D; H; S
Amino acid Q is similar to amino acids E; K; R
Amino acid R is similar to amino acids K; Q
Amino acid S is similar to amino acids A; N; T
Amino acid T is similar to amino acids S
Amino acid V is similar to amino acids I; L; M
Amino acid W is similar to amino acids F; Y
Amino acid Y is similar to amino acids F; H; W.

Conservative amino acid substitutions may occur over the full length of the sequence of a polypeptide sequence of a functional protein such as an enzyme. In one embodiment, such mutations are not pertaining the functional domains of an enzyme. In another embodiment conservative mutations are not pertaining the catalytic centers of an enzyme.

Therefore, according to the present invention the following calculation of percent-similarity applies:

%-similarity=[(identical residues+similar residues)/ length of the alignment region which is showing the respective sequence of this invention over its complete length]*100. Thus sequence similarity in relation to comparison of two amino acid sequences herein is calculated by dividing the number of identical residues plus the number of similar residues by the length of the alignment region which is showing the respective sequence of this invention over its complete length.

This value is multiplied with 100 to give "%-similarity".

Especially, variant enzymes comprising conservative mutations which are at least m percent similar to the respective parent sequences with m being an integer between 50 and 100, preferably 50, 55, 60, 65, 70, 75, 80, 85, 90, 91, 92, 93, 94, 95, 96, 97, 98 or 99 compared to the full length polypeptide sequence, are expected to have essentially unchanged enzyme properties. Variant enzymes described herein with m percent-similarity when compared to a parent enzyme, have enzymatic activity.

The term "hybridisation" as defined herein is a process wherein substantially complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, sepharose beads or any other resin. The hybridisation process can furthermore occur with one of the complementary nucleic acids immobilised to a solid support such as a nitro-cellulose or nylon membrane or immobilised by e.g. photolithography to a carrier, including, but not limited to a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

This formation or melting of hybrids is dependent on various parameters, including but not limited thereto the temperature. An increase in temperature favours melting, while a decrease in temperature favours hybridisation. However, this hybrid forming process is not following an applied change in temperature in a linear fashion: the hybridisation process is dynamic, and already formed nucleotide pairs are supporting the pairing of adjacent nucleotides as well. So, with good approximation, hybridisation is a yes-or-no process, and there is a temperature, which basically defines the border between hybridisation and no hybridisation. This temperature is the melting temperature (Tm). Tm is the temperature in degrees Celsius, at which 50% of all molecules of a given nucleotide sequence are hybridised into a double strand, and 50% are present as single strands.

The melting temperature (Tm) is dependent from the physical properties of the analysed nucleic acid sequence and hence can indicate the relationship between two distinct sequences.

However, the melting temperature (Tm) is also influenced by various other parameters, which are not directly related with the sequences, and the applied conditions of the hybridization experiment must be taken into account. For example, an increase of salts (e.g. monovalent cations) is resulting in a higher Tm.

Tm for a given hybridisation condition can be determined by doing a physical hybridisation experiment, but Tm can also be estimated in silico for a given pair of DNA sequences. In this embodiment, the equation of Meinkoth and Wahl (Anal. Biochem., 138:267-284, 1984) is used for stretches having a length of 50 or more bases: $Tm=81.5°C.+16.6 (\log M)+0.41 (\% GC)-0.61 (\% form)-500/L$.

M is the molarity of monovalent cations, % GC is the percentage of guanosine and cytosine nucleotides in the DNA stretch, % form is the percentage of formamide in the hybridisation solution, and L is the length of the hybrid in base pairs. The equation is for salt ranges of 0.01 to 0.4 M and % GC in ranges of 30% to 75%.

While above Tm is the temperature for a perfectly matched probe, Tm is reduced by about 1° C. for each 1% of mismatching (Bonner et al., J. Mol. Biol. 81: 123-135, 1973): Tm=[81.5° C.+16.6 (log M)+0.41 (% GC)−0.61 (% formamide)−500/L]−% non-identity.

This equation is useful for probes having 35 or more nucleotides and is widely referenced in scientific method literature (e.g. in: "Recombinant DNA Principles and Methodologies", James Greene, Chapter "Biochemistry of Nucleic acids", Paul S. Miller, page 55; 1998, CRC Press), in many patent applications (e.g. in: U.S. Pat. No. 7,026, 149), and also in data sheets of commercial companies (e.g. "Equations for Calculating Tm" from www.genomics.agilent.com).

Other formulas for Tm calculations, which are less preferred in this embodiment, might be only used for the indicated cases:

For DNA-RNA hybrids (Casey, J. and Davidson, N. (1977) Nucleic Acids Res., 4:1539): Tm=79.8° C.+18.5 (log M)+0.58 (% GC)+11.8 (% GC * % GC)−0.5 (% form)−820/L.

For RNA-RNA hybrids (Bodkin, D. K. and Knudson, D. L. (1985) J. Virol. Methods, 10: 45): Tm=79.8° C.+18.5 (log M)+0.58 (% GC)+11.8 (% GC * % GC)−0.35 (% form)−820/L.

For oligonucleotide probes of less than 20 bases (Wallace, R. B., et al. (1979) Nucleic Acid Res. 6: 3535): Tm=2×n(A+T)+4×n(G+C), with n being the number of respective bases in the probe forming a hybrid.

For oligonucleotide probes of 20-35 nucleotides, a modified Wallace calculation could be applied: Tm=22+1.46 n(A+T)+2.92 n(G+C), with n being the number of respective bases in the probe forming a hybrid.

For other oligonucleotides, the nearest-neighbour model for melting temperature calculation should be used, together with appropriate thermodynamic data:

$$Tm=(\Sigma(\Delta Hd)+\Delta Hi)/(\Sigma(\Delta Sd)+\Delta Si+\Delta Sself+R\times \ln(cT/b))+16.6 \log[Na+]-273.15$$

(Breslauer, K. J., Frank, R., Blöcker, H., Marky, L. A. 1986 Predicting DNA duplex stability from the base sequence. Proc. Natl Acad. Sci. USA 833746-3750; Alejandro Panjkovich, Francisco Melo, 2005. Comparison of different melting temperature calculation methods for short DNA sequences. Bioinformatics, 21 (6): 711-722)

where:

Tm is the melting temperature in degrees Celsius;

$\Sigma(\Delta Hd)$ and $J(\Delta Sd)$ are sums of enthalpy and entropy (correspondingly), calculated over all internal nearest-neighbor doublets;

$\Delta Sself$ is the entropic penalty for self-complementary sequences;

$\Delta Hi$ and $\Delta Si$ are the sums of initiation enthalpies and entropies, respectively;

R is the gas constant (fixed at 1.987 cal/K·mol);

cT is the total strand concentration in molar units;

constant b adopts the value of 4 for non-self-complementary sequences or equal to 1 for duplexes of self-complementary strands or for duplexes when one of the strands is in significant excess.

The thermodynamic calculations assume that the annealing occurs in a buffered solution at pH near 7.0 and that a two-state transition occurs.

Thermodynamic values for the calculation can be obtained from Table 1 in (Alejandro Panjkovich, Francisco Melo, 2005. Comparison of different melting temperature calculation methods for short DNA sequences. Bioinformatics, 21 (6): 711-722), or from the original research papers (Breslauer, K. J., Frank, R., Blocker, H., Marky, L. A. 1986 Predicting DNA duplex stability from the base sequence. Proc. Natl Acad. Sci. USA 833746-3750; SantaLucia, J., Jr, Allawi, H. T., Seneviratne, P. A. 1996 Improved nearest-neighbor parameters for predicting DNA duplex stability. Biochemistry 353555-3562; Sugimoto, N., Nakano, S., Yoneyama, M., Honda, K. 1996 Improved thermodynamic parameters and helix initiation factor to predict stability of DNA duplexes. Nucleic Acids Res. 244501-4505).

For an in silico estimation of Tm according to this embodiment, first a set of bioinformatic sequence alignments between the two sequences are generated. Such alignments can be generated by various tools known to a person skilled in the art, like programs "Blast" (NCBI), "Water" (EMBOSS) or "Matcher" (EMBOSS), which are producing local alignments, or "Needle" (EMBOSS), which is producing global alignments. Those tools should be applied with their default parameter setting, but also with some parameter variations. For example, program "MATCHER" can be applied with various parameter for gapopen/gapextend (like 14/4; 14/2; 14/5; 14/8; 14/10; 20/2; 20/5; 20/8; 20/10; 30/2; 30/5; 30/8; 30/10; 40/2; 40/5; 40/8; 40/10; 10/2; 10/5; 10/8; 10/10; 8/2; 8/5; 8/8; 8/10; 6/2; 6/5; 6/8; 6/10) and program "WATER" can be applied with various parameter for gapopen/gapextend (like 10/0,5; 10/1; 10/2; 10/3; 10/4; 10/6; 15/1; 15/2; 15/3; 15/4; 15/6; 20/1; 20/2; 20/3; 20/4; 20/6; 30/1; 30/2; 30/3; 30/4; 30/6; 45/1; 45/2; 45/3; 45/4; 45/6; 60/1; 60/2; 60/3; 60/4; 60/6), and also these programs shall be applied by using both nucleotide sequences as given, but also with one of the sequences in its reverse complement form. For example, BlastN (NCBI) can be applied with an increased e-value cut-off (e.g. e+1 or even e+10) to also identify very short alignments, especially in data bases of small sizes.

Important is that local alignments are considered, since hybridisation may not necessarily occur over the complete length of the two sequences, but may be best at distinct regions, which then are determining the actual melting temperature. Therefore, from all created alignments, the alignment length, the alignment % GC content (in a more accurate manner, the % GC content of the bases which are matching within the alignment), and the alignment identity has to be determined. Then the predicted melting temperature (Tm) for each alignment has to be calculated. The highest calculated Tm is used to predict the actual melting temperature.

The term "hybridisation over the complete sequence of the invention" as defined herein means that for sequences longer than 300 bases when the sequence of the invention is fragmented into pieces of about 300 to 500 bases length, every fragment must hybridise. For example, a DNA can be fragmented into pieces by using one or a combination of restriction enzymes. A bioinformatic in silico calculation of Tm is then performed by the same procedure as described above, just done for every fragment. The physical hybridisation of individual fragments can be analysed by sta8ndard Southern analysis, or comparable methods, which are known to a person skilled in the art.

The term "stringency" as defined herein is describing the ease by which hybrid formation between two nucleotide sequences can take place. Conditions of a "higher stringency" require more bases of one sequence to be paired with the other sequence (the melting temperature Tm is lowered in conditions of "higher stringency"), conditions of "lower stringency" allow some more bases to be unpaired. Hence the degree of relationship between two sequences can be estimated by the actual stringency conditions at which they are still able to form hybrids. An increase in stringency can be achieved by keeping the experimental hybridisation temperature constant and lowering the salts concentrations, or by keeping the salts constant and increasing the experimental hybridisation temperature, or a combination of these parameter. Also an increase of formamide will increase the stringency. The skilled artisan is aware of additional parameters which may be altered during hybridisation and which will either maintain or change the stringency conditions (Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

A typical hybridisation experiment is done by an initial hybridisation step, which is followed by one to several washing steps. The solutions used for these steps may contain additional components, which are preventing the degradation of the analyzed sequences and/or prevent unspecific background binding of the probe, like EDTA, SDS, fragmented sperm DNA or similar reagents, which are known to a person skilled in the art (Sambrook et al. (2001) Molecular Cloning: a laboratory manual, $3^{rd}$ Edition, Cold Spring Harbor Laboratory Press, CSH, New York or to Current Protocols in Molecular Biology, John Wiley & Sons, N.Y. (1989 and yearly updates).

A typical probe for a hybridisation experiment is generated by the random-primed-labelling method, which was initially developed by Feinberg and Vogelstein (Anal. Biochem., 132 (1), 6-13 (1983); Anal. Biochem., 137 (1), 266-7 (1984) and is based on the hybridisation of a mixture of all possible hexanucleotides to the DNA to be labelled. The labelled probe product will actually be a collection of fragments of variable length, typically ranging in sizes of 100-1000 nucleotides in length, with the highest fragment concentration typically around 200 to 400 bp. The actual size range of the probe fragments, which are finally used as probes for the hybridisation experiment, can also be influenced by the used labelling method parameter, subsequent purification of the generated probe (e.g. agarose gel), and the size of the used template DNA which is used for labelling (large templates can e.g. be restrictiondigested using a 4 bp cutter, e.g. HaeIII, prior labeling).

For the present invention, the sequence described herein is analysed by a hybridisation experiment, in which the probe is generated from the other sequence, and this probe is generated by a standard random-primed-labelling method. For the present invention, the probe is consisting of a set of labelled oligonucleotides having sizes of about 200-400 nucleotides. A hybridisation between the sequence of this invention and the other sequence means, that hybridisation of the probe occurs over the complete sequence of this invention, as defined above. The hybridisation experiment is done by achieving the highest stringency by the stringency of the final wash step. The final wash step has stringency conditions comparable to the stringency conditions of at least Wash condition 1: 1.06×SSC, 0.1% SDS, 0% formamide at 50° C., in another embodiment of at least Wash condition 2: 1.06×SSC, 0.1% SDS, 0% formamide at 55° C., in another embodiment of at least Wash condition 3:1.06× SSC, 0.1% SDS, 0% formamide at 60° C., in another embodiment of at least Wash condition 4: 1.06×SSC, 0.1% SDS, 0% formamide at 65° C., in another embodiment of at least Wash condition 5: 0.52×SSC, 0.1% SDS, 0% formamide at 65° C., in another embodiment of at least Wash condition 6: 0.25×SSC, 0.1% SDS, 0% formamide at 65° C., in another embodiment of at least Wash condition 7: 0.12× SSC, 0.1% SDS, 0% formamide at 65° C., in another embodiment of at least Wash condition 8: 0.07×SSC, 0.1% SDS, 0% formamide at 65° C.

A "low stringent wash" has stringency conditions comparable to the stringency conditions of at least Wash condition 1, but not more stringent than Wash condition 3, wherein the wash conditions are as described above.

A "high stringent wash" has stringency conditions comparable to the stringency conditions of at least Wash condition 4, in another embodiment of at least Wash condition 5, in another embodiment of at least Wash condition 6, in another embodiment of at least Wash condition 7, in another embodiment of at least Wash condition 8, wherein the wash conditions are as described above.

The term "heterologous" (or exogenous or foreign or recombinant or non-native) polypeptide is defined herein as a polypeptide that is not native to the host cell, a polypeptide native to the host cell in which structural modifications, e.g., deletions, substitutions, and/or insertions, have been made by recombinant DNA techniques to alter the native polypeptide, or a polypeptide native to the host cell whose expression is quantitatively altered or whose expression is directed from a genomic location different from the native host cell as a result of manipulation of the DNA of the host cell by recombinant DNA techniques, e.g., a stronger promoter. Similarly, the term "heterologous" (or exogenous or foreign or recombinant or non-native) polynucleotide refers to a polynucleotide that is not native to the host cell, a polynucleotide native to the host cell in which structural modifications, e.g., deletions, substitutions, and/or insertions, have been made by recombinant DNA techniques to alter the native polynucleotide, or a polynucleotide native to the host cell whose expression is quantitatively altered as a result of manipulation of the regulatory elements of the polynucleotide by recombinant DNA techniques, e.g., a stronger promoter, or a polynucleotide native to the host cell, but integrated not within its natural genetic environment as a result of genetic manipulation by recombinant DNA techniques.

With respect to two or more polynucleotide sequences or two or more amino acid sequences, the term "heterologous" is used to characterized that the two or more polynucleotide sequences or two or more amino acid sequences are naturally not occurring in the specific combination with each other.

For the purposes of the invention, "recombinant" (or transgenic) with regard to a cell or an organism means that the cell or organism contains a heterologous polynucleotide which is introduced by man by gene technology and with regard to a polynucleotide includes all those constructions brought about by man by gene technology/recombinant DNA techniques in which either (a) the sequence of the polynucleotide or a part thereof, or
(b) one or more genetic control sequences which are operably linked with the polynucleotide, including but not limited thereto a promoter, or
(c) both a) and b) are not located in their wildtype genetic environment or have been modified.

The term "native" (or wildtype or endogenous) cell or organism and "native" (or wildtype or endogenous) polynucleotide or polypeptide refers to the cell or organism as found in nature and to the polynucleotide or polypeptide in question as found in a cell in its natural form and genetic environment, respectively (i.e., without there being any human intervention).

A "DNA with methylation pattern foreign to a cell" refers to a DNA comprising a methylation pattern not naturally occurring in the cell and thus can be recognized and cleaved by one or more restriction enzymes of the cell.

The terms "polynucleotide", "nucleic acid sequence", "nucleotide sequence", "nucleic acid", "nucleic acid molecule" are used interchangeably herein and refer to nucleotides, either ribonucleotides or deoxyribonucleotides or a combination of both, in a polymeric unbranched form of any length. "Polynucleotides" are composed of monomers, which are "nucleotides" made of three components: a pentose sugar, a phosphate group, and a nitrogenous base.

The term "nucleic acid construct" as used herein refers to a nucleic acid molecule, either single- or double-stranded, which is isolated from a naturally occurring gene or is modified to contain segments of nucleic acids in a manner that would not otherwise exist in nature or is synthetic. The term "nucleic acid construct" is synonymous with the term "expression cassette" when the nucleic acid construct contains the control sequences required for expression of a polynucleotide.

The term "control sequence" is defined herein to include all sequences affecting the expression of a polynucleotide, including but not limited thereto, the expression of a polynucleotide encoding a polypeptide. Each control sequence may be native or foreign to the polynucleotide or native or foreign to each other. Such control sequences include, but are not limited to, promoter sequence, 5'-UTR (also called leader sequence), ribosomal binding site (RBS, shine dalgarno sequence), 3'-UTR, and transcription start and stop sites.

The term "functional linkage" or "operably linked" with respect to regulatory elements, is to be understood as meaning the sequential arrangement of a regulatory element (including but not limited thereto a promoter) with a nucleic acid sequence to be expressed and, if appropriate, further regulatory elements (including but not limited thereto a terminator) in such a way that each of the regulatory elements can fulfil its intended function to allow, modify, facilitate or otherwise influence expression of said nucleic acid sequence. For example, a control sequence is placed at an appropriate position relative to the coding sequence of the polynucleotide sequence such that the control sequence directs the expression of the coding sequence of a polypeptide. Preferred arrangements are those in which the nucleic acid sequence to be expressed recombinantly is positioned behind the sequence acting as promoter, so that the two sequences are linked covalently to each other. In one embodiment, the nucleic acid sequence to be transcribed is located behind the promoter in such a way that the transcription start is identical with the desired beginning of the RNA. Functional linkage, and an expression construct, can be generated by means of customary recombination and cloning techniques as described (e.g., Sambrook, J. and Russell, D. W. Molecular cloning. A laboratory manual, 3rd ed, Cold Spring Harbor Laboratory Press, Cold Spring Harbor, N Y. 2001.); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands; Plant Molecular Biology Labfax (1993) by R. D. D. Croy, published by BIOS Scientific Publications Ltd (UK) and Blackwell Scientific Publications (UK)). However, further sequences, including but not limited thereto a sequence, which acts as a linker with specific cleavage sites for restriction enzymes, or as a signal peptide, may also be positioned between the two sequences. The insertion of sequences may also lead to the expression of fusion proteins.

A "promoter" or "promoter sequence" is a nucleotide sequence located upstream of a gene on the same strand as the gene that enables that gene's transcription. Promoter is followed by the transcription start site of the gene. Promoter is recognized by RNA polymerase (together with any required transcription factors), which initiates transcription. A functional fragment or functional variant of a promoter is a nucleotide sequence which is recognizable by RNA polymerase, and capable of initiating transcription.

The term "promoter sequence comprising a consensus sequence and wherein the consensus sequence is immediately followed by a transcription start site" or the term "promoter sequence comprising a consensus sequence immediately followed by a transcription start site" are meant herein as the transcription start site being directly adjacent to the consensus sequence, i.e., without any linking additional nucleotides between consensus sequence and transcription start site.

The term "transcription start site" or "transcriptional start site" shall be understood as the location where the transcription starts at the 5' end of a gene sequence. In prokaryotes the first nucleotide, referred to as +1 is in general an adenosine (A) or guanosine (G) nucleotide. In this context, the terms "sites" and "signal" can be used interchangeably herein.

When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG, CTG or TTG and ends with a stop codon such as TAA, TAG, or TGA. The coding sequence may be a DNA, cDNA, synthetic, or recombinant nucleotide sequence. The start codon can also be named herein as "translational start signal" or "translational start site". The stop codon can also be named herein as "translational stop signal" or "translational stop site".

The term "expression" or "gene expression" means the transcription of a specific gene or specific genes or specific nucleic acid construct. The term "expression" or "gene expression" in particular means the transcription of a gene or genes or genetic construct into structural RNA (e.g., rRNA, tRNA) or mRNA with or without subsequent translation of the latter into a protein. The process includes transcription of DNA and processing of the resulting mRNA product.

The term "expression vector" is defined herein as a linear or circular DNA molecule that comprises a polynucleotide that is operably linked to one or more control sequences that provides for the expression of the polynucleotide.

The term "moderate expression" of a gene is defined herein as an expression level of a given gene that does not impair cellular growth or viability and allows continuous cultivation of the host cell.

The term "host cell", as used herein, includes any cell type that is susceptible to transformation, transfection, transduction, conjugation, and the like with a nucleic acid construct or expression vector.

The term "introduction" and variations thereof are defined herein as the transfer of a DNA into a host cell. The introduction of a DNA into a host cell can be accomplished by any method known in the art, including, the not limited to, transformation, transfection, transduction, conjugation, and the like.

The term "donor cell" is defined herein as a cell that is the source of DNA introduced by any means to another cell.

The term "recipient cell" is defined herein as a cell into which DNA is introduced.

The term "fermentation in industrial scale" (also called large-scale fermentation) refers to fermentation processes with fermenter volumes of greater than or equal to 20 liters.

The term "DNA methyltransferase that methylates DNA resulting in a DNA containing 5-methylcytosine within the recognition sequence GCNGC" is defined herein as a DNA (cytosine-5)-methyltransferase (EC 2.1.1.37) that catalyzes the transfer of a methyl group from S-adenosyl-L-methionine to cytosine within the sequence GCNGC, resulting in S-adenosyl-Lhomocysteine and DNA containing 5-methylcytosine. For purposes of the present invention, DNA methyltransferase activity is determined according to the procedure described by Pfeifer et al., 1983, Biochim. Biophys. Acta 740: 323-30. One unit of DNA methyltransferase activity is the amount required to protect 1 µg of lambda DNA in 1 hour in a total reaction volume of 20 µl against cleavage by the corresponding restriction endonuclease.

The term "restriction-modification system" is defined herein as a restriction endonuclease, a corresponding DNA methyltransferase that protects DNA from cleavage by the restriction endonuclease, and the genes encoding at least these two enzymes.

The term "operon" is understood herein as a unit of genomic DNA, containing a single promoter, and one or more genes, all of which are transcribed from that single promoter. The genes in the operon may overlap, or may have untranslated regions (UTRs) between each other. These UTRs may optionally have additional control elements, affecting translational efficiency.

The term "secA operon" is understood herein as on operon comprising a secA gene and a promoter sequence endogenously linked thereto, i.e., the wildtype promoter of this secA operon ("secA promoter"). Without being limited thereto, an example of a secA-containing operon is a construct consisting of a promoter, a 5'UTR, a secM gene (secretion monitor, SecA regulator SecM), a UTR, and a secA gene, wherein the promoter is the native promoter sequence of the secA gene containing operon.

The SecA protein is a multi-functional protein involved in the process of protein secretion (protein translocation) across the bacterial inner cell membrane (Green, Erin R., and Joan Mecsas. "Bacterial Secretion Systems—An Overview." Microbiology spectrum 4.1 (2016)).

The secA gene, coding the SecA protein, is usually annotated as "translocase subunit SecA", "preprotein translocase subunit SecA", "protein translocase subunit SecA", "translocase binding subunit (ATPase)", or "preprotein translocase; secretion protein". Some organisms have two SecA protein homologs, one of which is essential and the other one is not (Braunstein M, Brown A M, Kurtz S, Jacobs W R Jr. "Two nonredundant SecA homologues function in mycobacteria." Journal of Bacteriology, 1 Dec. 2001, 183 (24):6979-6990; Feltcher M E, Braunstein M. "Emerging themes in SecA2-mediated protein export." Nature Reviews Microbiology, 24 Sep. 2012, 10(11):779-789). In organisms, which have two SecA-like translocase proteins, the annotation of the protein translocase subunit SecA gene pertinent to this patent application is usually marked by an additional index 1, e.g. "protein translocase subunit SecA1", and denotes the essential translocase.

The term "reporter gene" is understood herein as a gene whose product can be readily assayed subsequent to introduction a host cell, and can be used as markers for screening successfully transformed cells, for studying regulation of gene expression, or serve as controls for standardizing transformation efficiencies. Common reporter genes encode for fluorescent proteins, for example but not limited to green fluorescent protein GFP, red fluorescent protein RFP, and genes encoding for enzymes catalyzing a chemical reaction resulting in a detectable product, for example but not limited to galactosidase, and luciferase genes. The protein encoded by the reporter gene is also called herein "reporter protein".

DETAILED DESCRIPTION

Nucleic Acid Constructs

In one embodiment, the present invention is directed to a nucleic acid construct comprising a polynucleotide operably linked to one or more control sequence that directs the expression of the polynucleotide in a host cell, wherein at least one control sequence comprises a promoter sequence of a secA operon comprising a secA gene (such promoter sequence herein also called "secA promoter") or a functional fragment or functional variant of the promoter sequence and wherein said promoter sequence is heterologous to the polynucleotide. In one embodiment, the promoter sequence of an operon comprising a secA gene or the functional fragment or functional variant thereof confers a moderate expression level.

In a further embodiment, the promoter sequence comprises the consensus sequence (SEQ ID NO: 117)
TKNTTTGGAAATN(8-12)RTRTGNTAWRATAWN(4-6)

and wherein the consensus sequence is immediately followed by a transcription start site.

In a further embodiment, the promoter sequence comprises the consensus sequence

TKNTTTGGAAATNNNNNNNNNRTRTGNTAWRATAWNNNN and wherein the consensus sequence is immediately followed by a transcription start site.

In yet another embodiment, the promoter sequence
(a) has at least 70% sequence identity with SEQ ID NO: 9, 53, 54, 55, 56, 57, 58, 59, 60, 61, 62, 63, 64, 65, 66, 67, or 68;
(b) hybridizes under high stringency conditions with (i) a polynucleotide comprising SEQ ID NO: 9, 53, 54, 55, 56, 57, 58, 59, 60, 61, 62, 63, 64, 65, 66, 67, or 68, or (ii) the full-length complement of (i); or
(c) is a variant of the promoter sequence of SEQ ID NO: 9, 53, 54, 55, 56, 57, 58, 59, 60, 61, 62, 63, 64, 65, 66, 67, or 68 comprising a substitution, deletion, and/or insertion at one or more positions and wherein the variant of the promoter sequence has promoter activity.

In yet another embodiment, the promoter sequence has at least 70% sequence identity with SEQ ID NO: 9, 53, 54, 55, 56, 57, 58, 59, 60, 61, 62, 63, 64, 65, 66, 67, or 68.

In a preferred embodiment, the promoter sequence has at least 70%, at least 75%, at least 80%, at least 85%, at least 90%, at least 92%, at least 95%, at least 98%, at least 99%, or even 100% sequence identity with SEQ ID NO: 9. Preferably, the promoter sequence has at least 90% or at least 95% sequence identity with SEQ ID NO: 9.

In another embodiment, the promoter sequence of an operon comprising a secA gene is from a *Bacillus* species. The *Bacillus* species may be, but is not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus methylotrophicus, Bacillus cereus Bacillus paralicheniformis, Bacillus subtilis,* and *Bacillus thuringiensis* cells. In one embodiment, the *Bacillus* species is *Bacillus amyloliquefaciens, Bacillus lentus, Bacillus* licheniformis, *Bacillus stearothermophilus* or *Bacillus subtilis*. In another embodiment, the *Bacillus* species is *Bacillus licheniformis* or *Bacillus subtilis*. In another embodiment, the *Bacillus* species is *Bacillus licheniformis*. Preferably, the *Bacillus* species is *Bacillus licheniformis*.

In yet another embodiment, the promoter sequence has at least 70%, at least 75%, at least 80%, at least 85%, at least 90%, at least 92%, at least 95%, at least 98%, at least 99%, or even 100% sequence identity with SEQ ID NO: 9, 53, 54, 55, 56, 57, 58, 59, 60, 61, 62, 63, 64, 65, 66, 67, or 68 and wherein the promoter sequence is from a *Bacillus* species.

In a preferred embodiment, the promoter sequence has at least 70%, at least 75%, at least 80%, at least 85%, at least 90%, at least 92%, at least 95%, at least 98%, at least 99%, or even 100% sequence identity with SEQ ID NO: 9 and wherein the promoter sequence is from a *Bacillus* species, in a specific embodiment from *Bacillus licheniformis*.

In another embodiment, the promoter sequence comprises the consensus sequence

```
                                            (SEQ ID NO: 118)
TCAWTMNTGCTGYN(11-13)TTAATGRTAADATTYDTN(4-5)
``` and wherein the consensus sequence is immediately followed by a transcription start site.

In another embodiment, the promoter sequence comprises the consensus sequence

```
TCAWTMNTGCTGYNNNNNNNNNNNNNNTTAATGRTAADATTYDTNNNN
``` and wherein the consensus sequence is immediately followed by a transcription start site.

In yet another embodiment, the promoter sequence
(a) has at least 70% sequence identity with SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98;
(b) hybridizes under high stringency conditions with (i) a polynucleotide comprising SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98, or (ii) the full-length complement of (i); or
(c) is a variant of the promoter sequence of SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98 comprising a substitution, deletion, and/or insertion at one or more positions and wherein the variant of the promoter sequence has promoter activity.

In yet another embodiment, the promoter sequence has at least 70%, at least 75%, at least 80%, at least 85%, at least 90%, at least 92%, at least 95%, at least 98%, at least 99%, or even 100% sequence identity with SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98.

In yet another embodiment, the promoter sequence has at least 70%, at least 75%, at least 80%, at least 85%, at least 90%, at least 92%, at least 95%, at least 98%, at least 99%, or even 100% sequence identity with SEQ ID NO: 82.

In a further embodiment, the promoter sequence of an operon comprising a secA gene is from an Enterobacteria species. In another embodiment, the promoter sequence is from an Enterobacteriaceae species. In yet another embodiment, the promoter sequence is from *Escherichia coli*.

In yet another embodiment, the promoter sequence has at least 70%, at least 75%, at least 80%, at least 85%, at least 90%, at least 92%, at least 95%, at least 98%, at least 99%, or even 100% sequence identity with SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98 and wherein the promoter sequence is from an Enterobacteria species.

In yet another embodiment, the promoter sequence has at least 70%, at least 75%, at least 80%, at least 85%, at least 90%, at least 92%, at least 95%, at least 98%, at least 99%, or even 100% sequence identity with SEQ ID NO: 82 and wherein the promoter sequence is from an Enterobacteria species, in a specific embodiment from *Escherichia coli*.

In one embodiment, the promoter sequence is from an operon comprising a secA gene from a microorganism selected from the group consisting of Bacillaceae, Lactobacillaceae, Enterobacteriaceae, Staphylococcaceae, Corynebacteriaceae, Brevibacteriaceae, Pseudomonadaceae, Streptomycetaceae, Acetobacteraceae, and Clostridiaceae.

In another embodiment, the promoter sequence is from an operon comprising a secA gene from a microorganism selected from the group consisting of *Bacillus licheniformis, Lactobacillus acidophilus, Escherichia coli, Staphylococcus aureus, Corynebacterium glutamicum, Pseudomonas putida, Streptomyces coelicolor, Gluconobacter oxydans,* and *Clostridium acetobutylicum*.

In one embodiment, the promoter sequence is from an operon comprising a secA gene which encodes for a SecA protein having at least 60% sequence identity to the amino acid sequence displayed in SEQ ID NO: 44, 45, 46, 47, 48, 49, 50, 51, or 52.

In one embodiment, the promoter sequence is from an operon comprising a secA gene which encodes for a SecA protein having at least 60%, at least 65%, at least 70%, at least 75%, at least 80%, at least 85%, at least 90%, at least 92%, at least 95%, at least 98%, at least 99%, or even 100% sequence identity with the amino acid sequence displayed in SEQ ID NO: 44, 45, 46, 47, 48, 49, 50, 51, or 52.

In a further one embodiment, the promoter sequence is from an operon comprising a secA gene which encodes for a SecA protein having at least 60%, at least 65%, at least 70%, at least 75%, at least 80%, at least 85%, at least 90%, at least 92%, at least 95%, at least 98%, at least 99%, or even 100% sequence identity with the amino acid sequence displayed in SEQ ID NO: 44.

In a further one embodiment, the promoter sequence is from an operon comprising a secA gene which encodes for a SecA protein having at least 60%, at least 65%, at least 70%, at least 75%, at least 80%, at least 85%, at least 90%, at least 92%, at least 95%, at least 98%, at least 99%, or even 100% sequence identity with the amino acid sequence displayed in SEQ ID NO: 45.

In one embodiment, the nucleic acid construct and/or the expression vector described herein comprises one or more further control sequences. Such control sequences include, but are not limited to promoter sequence, 5'-UTR (also called leader sequence), ribosomal binding site (RBS, shine dalgarno sequence), 3'-UTR, and transcription and translation terminator. In one embodiment, the control sequences may be provided with linkers for the purpose of introducing specific restriction sites facilitating ligation of the control sequences with the polynucleotide to be expressed.

The nucleic acid construct comprises a suitable transcription start and terminator sequence. Any transcription start or terminator that is functional in the host cell of choice may be used in the present invention.

In one embodiment the nucleic acid construct comprises a suitable UTR (untranslated region) sequence. In one embodiment, the nucleic acid construct described herein comprises a 5'UTR and/or a 3'UTR sequence. In one embodiment, the one or more control sequence of the nucleic acid construct comprises a 5'UTR, also referred to as leader sequence. In another one embodiment, the one or more control sequence of the nucleic acid construct comprises a 5'UTR sequence comprising a ribosome-binding site also referred to as a shine-dalgarno sequence. Any leader sequence that is functional in the host cell of choice may be used in the present invention. The UTR can be natural or artificial. In one embodiment, the 5'UTR has at least 90%, at least 92%, at least 95%, at least 98% or even 100% sequence identity to SEQ ID NO: 13 or to any of SEQ ID NO: 99 to 116.

The nucleic acid constructs described herein can be used for expression of a protein of interest. Hence, in one embodiment the polynucleotide of the nucleic acid construct operably linked to one or more control sequence that directs the expression of the polynucleotide in a host cell, wherein at least one control sequence comprises a promoter sequence of an operon comprising a secA gene or a functional fragment or functional variant thereof, is a polynucleotide encoding for a protein of interest. In one embodiment the protein of interest is selected from the group consisting of a methyltransferase, an endonuclease, a serine recombinase, a tyrosine recombinase, and a protein conferring antibiotic resistance.

The nucleic acid construct and/or the expression vector described herein can be used for providing a moderate expression level of a polynucleotide, preferably a polynucleotide encoding a protein of interest, in a host cell.

In one embodiment, the nucleic acid construct and/or the expression vector described herein can be used for expression of a polynucleotide, preferably a polynucleotide encoding a protein of interest in a host cell, providing an expression level of said polynucleotide allowing continuous cultivation of the host cell.

Expression Vectors

In another embodiment, the present invention is directed to an expression vector comprising the nucleic acid construct described herein. Thus, in one embodiment, the present invention is directed to an expression vector comprising a nucleic acid construct comprising a polynucleotide operably linked to one or more control sequence that directs the expression of the polynucleotide in a host cell, wherein at least one control sequence comprises a promoter sequence of an operon comprising a secA gene or a functional fragment or functional variant thereof and wherein said promoter sequence is heterologous to the polynucleotide.

In one embodiment, the expression vector is located outside the chromosomal DNA of the host cell. In another embodiment, the expression vector is integrated into the chromosomal DNA of the host cell. The expression vector can be linear or circular. In one embodiment, the expression vector is a viral vector or a plasmid.

For autonomous replication, the expression vector may further comprise an origin of replication enabling the vector to replicate autonomously in the host cell in question. Bacterial origins of replication include but are not limited to the origins of replication of plasmids pBR322, pUC19, pSC101, pACYC177, and pACYC184 permitting replication in *E. coli* (Sambrook, J. and Russell, D. W. Molecular cloning. A laboratory manual, 3rd ed, Cold Spring Harbor Laboratory Press, Cold Spring Harbor, N.Y. 2001; Cohen, S. N., Chang, A. C. Y., Boyer, H. W., & Helling, R. B. (1973). Construction of Biologically Functional Bacterial Plasmids In Vitro. Proceedings of the National Academy of Sciences of the United States of America, 70(11), 3240-3244), and pUB110, pC194, pTB19, pAMB1, and pTA1060 permitting replication in *Bacillus* (Janniere, L., Bruand, C., and Ehrlich, S. D. (1990). Structurally stable *Bacillus subtilis* cloning vectors. Gene 87, 53-6; Ehrlich, S. D., Bruand, C., Sozhamannan, S., Dabert, P., Gros, M. F., Janniere, L., and Gruss, A. (1991). Plasmid replication and structural stability in *Bacillus subtilis*. Res. Microbiol. 142, 869-873), and pE194 (Dempsey, L. A. and Dubnau, D. A. (1989). Localization of the replication origin of plasmid pE194. J. Bacteriol. 171, 2866-2869). The origin of replication may be one having a mutation to make its function temperature-sensitive in the host cell (see, e.g., Ehrlich, 1978, Proceedings of the National Academy of Sciences USA 75:1433-1436).

In one embodiment, the expression vector contains one or more selectable markers that permit easy selection of transformed cells. A selectable marker is a gene encoding a product, which provides for biocide resistance, resistance to heavy metals, prototrophy to auxotrophs, and the like. Bacterial selectable markers include but are not limited to the dal genes from *Bacillus subtilis* or *Bacillus licheniformis*, or markers that confer antibiotic resistance such as ampicillin, kanamycin, erythromycin, chloramphenicol or tetracycline resistance. Furthermore, selection may be accomplished by co-transformation, e.g., as described in WO91/09129, where the selectable marker is on a separate vector.

Proteins of Interest

The nucleic acid constructs described herein can be used for expression of a protein of interest. Thus, in one embodiment the nucleic acid construct described herein comprises a polynucleotide, wherein the polynucleotide encodes for a protein of interest. Hence, in one embodiment the polynucleotide of the nucleic acid construct operably linked to one or more control sequence that directs the expression of the polynucleotide in a host cell, wherein at least one control sequence comprises a promoter sequence of an operon comprising a secA gene or a functional fragment or functional variant thereof, is a polynucleotide encoding for a protein of interest.

As the present invention is directed to the use of a promoter sequence of an operon comprising a secA gene or a functional fragment or functional variant thereof for heterologous expression of a polynucleotide, the promoter sequence of an operon comprising a secA gene or a functional fragment or functional variant thereof is not naturally associated with the polynucleotide. Thus, in a preferred embodiment the polynucleotide to be expressed by the promoter sequence of an operon comprising a secA gene or a functional fragment or functional variant thereof does not comprise a secA gene.

In one embodiment, the polynucleotide does not comprise a reporter gene. Thus, in one embodiment the protein of interest is not a reporter protein. In a preferred embodiment, the protein of interest is not a reporter protein selected from the group consisting of β-galactosidase, chloramphenicol acetyltransferase, alkaline phosphatase, β-glucoronidase, luciferase, aequorin, and fluorescent protein, preferably green fluorescent protein, red fluorescent protein, and yellow fluorescent protein.

In one embodiment, the polynucleotide does not comprise a reporter gene selected from the group consisting of lacZ, spoVG-lacZ, cat, phoA, gusA, luciferase gene, aequorine gnee, gfp, yfp, and rfp.

In a particular embodiment, the present invention is further directed to methods of producing a native or foreign polypeptide comprising: (a) cultivating a recombinant host cell comprising the nucleic acid construct as described herein under conditions conducive for production of the protein of interest; and (b) optionally recovering the protein of interest.

In one embodiment, the protein of interest is tolerated by the host cell only in limited quantities. Thus, in one embodiment the expression of protein of interest by using the secA promoter described herein allows for continuous cultivation of the host cell without negative growth effects. Thus, in one embodiment the expression level of protein of interest conferred by the secA promoter described herein is not toxic to the host cell. In one embodiment, the secA promoter described herein provides to the cell the protein of interest in a moderate expression level. In a one embodiment, the protein of interest is toxic to the host cell when expressed in large quantities. In one embodiment, the protein of interest is an enzyme. In another embodiment, the protein of interest is an enzyme that is tolerated by the host cell only in limited quantities.

In one embodiment the protein of interest is selected from the group consisting of a DNA or RNA modifying enzyme, and a protein conferring antibiotic resistance. In one embodiment the protein of interest is selected from the group consisting of a DNA or RNA modifying enzyme. In one embodiment the protein of interest is a DNA or RNA modifying enzyme, selected from the list of a methyltransferase, an endonuclease, a serine recombinase, and a tyrosine recombinase.

In a further embodiment, the endonuclease is i-SceI or Cas9 endonuclease. In another embodiment, the serine recombinase is cre from P1 phage or FLP from *S. cerevisiae*. In yet another embodiment, the tyrosine recombinase is lambda integrase. In a further embodiment, the protein conferring antibiotic resistance is encoded by a gene selected from the group consisting of a blasticidin S resistance gene, a bleomycin resistance gene, a chloramphenicol acetyltransferase gene, an aminoglycoside modifying enzyme, including but not limited to aminoglycoside acetyltransferases, aminoglycoside acetyltransferases, aminoglycoside nucleotidyltransferases, a tetracycline resistance gene, including but not limited to ribosomal protection via Tet(M), TetO-Q), Tet(S), OtrA, tetracycline efflux transporters Tet(A-E, G, H, K, L, P [tetA(P)]), and OtrB.

In a further embodiment, the protein of interest is a DNA methyltransferase.

Figure 1:
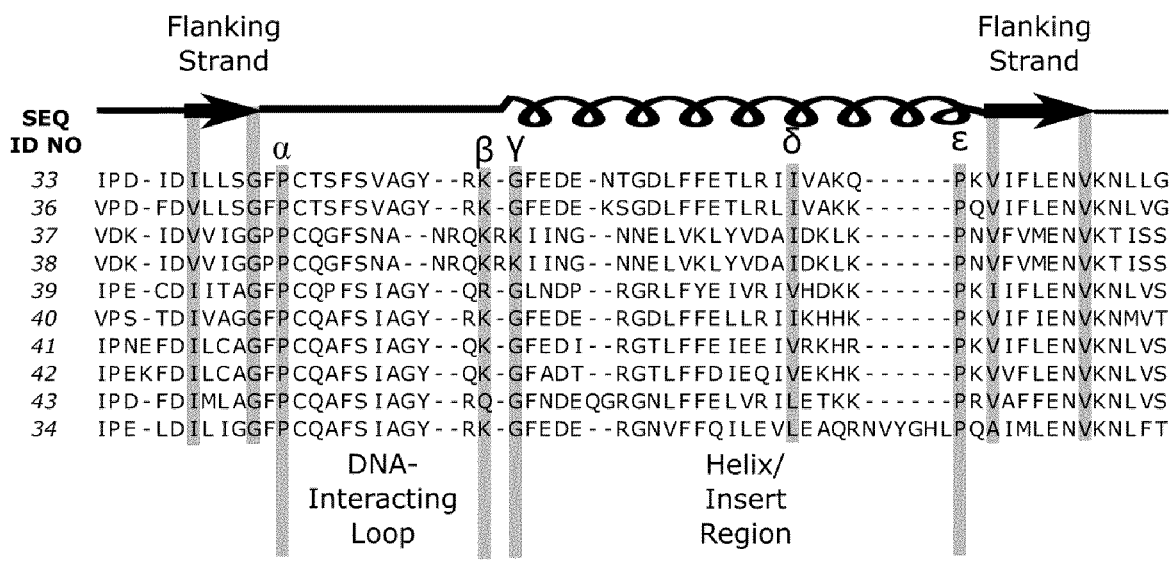
FIG. 1 shows relevant sections from a structure-based multiple sequence alignment of predicted structures of the methyltransferases disclosed herein, which can be created using standard homology modelling programs such as the SWISS-MODEL webserver (Biasini M., Bienert S., Waterhouse A., Arnold K., Studer G., Schmidt T., Kiefer F., Cassarino T. G., Bertoni M., Bordoli L., Schwede T. (2014). SWISS-MODEL: modelling protein tertiary and quaternary structure using evolutionary information Nucleic Acids Research 2014 (1 Jul. 2014) 42 (W1): W252-W258) using default parameters and the following structural templates from the RCSB PDB database (Berman H. M., Westbrook J., Feng Z., Gilliland G., Bhat T. N., Weissig H., Shindyalov I. N., Bourne P. E. (2000) The Protein Data Bank Nucleic Acids Research, 28: 235-242.): 2uyc_A (used for SEQ ID NO: 33 (M.Fnu4HI), SEQ ID NO: 34 (M.RBH3250), SEQ ID NO: 41 (M.CocII)), 2i9k_C (used for SEQ ID NO: 36 (M.Bsp61), SEQ ID NO: 43 (M.LlaDII)), 3swr_A (used for SEQ ID NO: 37 (M.Cdi1330711), SEQ ID NO: 38 (M.Cdi6301V)), 1mht_C (used for SEQ ID NO: 39

FIG. 1 shows a structure-based multiple sequence alignment of the amino acid sequences of various DNA methyltransferases comprising these structural features. It can be derived from FIG. 1 that between amino acid residue 72 and amino acid residue 106 according to the numbering of SEQ ID NO: 33 there are 33 amino acids in SEQ ID NOs: 33, 36, 37, and 38, there are 32 amino acids in SEQ ID NOs: 39-42 and there are 34 amino acids in SEQ ID NO: 43. However, there are 38 amino acids between amino acid residue 72 and amino acid residue 106 according to the numbering of SEQ ID NO: 33 in SEQ ID NO: 34. Thus, compared to SEQ ID NO: 34 there is a deletion in SEQ ID NO: 33 and SEQ ID NO: 36-43.

Hence, the DNA methyltransferase described herein and used in the methods of the present invention methylates DNA within the recognition sequence GCNGC resulting in DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33.

In one embodiment, the DNA methyltransferase described herein and used in the methods of the present invention methylates DNA within the recognition sequence GCNGC resulting in DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33, wherein the DNA methyltransferase comprises at least 22, preferably at least 28 amino acid residues between amino acid residue 72 and amino acid residue 106 according to the numbering of SEQ ID NO: 33. Hence, preferably, the DNA methyltransferase comprises between amino acid residue 72 and amino acid residue 106 according to the numbering of SEQ ID NO: 33 22-34, preferably 28-34, more preferably 22-33, even more preferably 28-33, most preferably 30-34 or 30-33 amino acid residues. Most preferred, there are 33 amino acids residues between amino acid residue 72 and amino acid residue 106 according to the numbering of SEQ ID NO: 33.

In another embodiment, the DNA methyltransferase used in these methods of the present comprises less than 23 amino acid residues between amino acid residue 84 and amino acid residue 106 according to the numbering of SEQ ID NO: 33.

In another embodiment, the DNA methyltransferase comprises less than 23 amino acid residues between amino acid residue 84 and amino acid residue 106 according to the numbering of SEQ ID NO: 33, wherein the DNA methyltransferase comprises at least 12, preferably at least 18 amino acid residues between amino acid residue 84 and amino acid residue 106 according to the numbering of SEQ ID NO: 33. Hence, preferably, the DNA methyltransferase comprises between amino acid residue 84 and amino acid residue 106 according to the numbering of SEQ ID NO: 33 12-22, preferably 18-22, more preferably 12-21, even more preferably 18-21 amino acid residues.

In another embodiment the DNA methyltransferase used in the methods of the present invention methylates DNA within the recognition sequence GCNGC resulting in DNA containing 5-methylcytosine within the recognition sequence GCNGC and comprises less than 5 amino acid residues between amino acid residue 101 and amino acid residue 106 according to the numbering of SEQ ID NO: 33.

In preferred embodiment the DNA methyltransferase described herein and used in the methods of the present invention methylates DNA within the recognition sequence GCNGC resulting in DNA containing 5-methylcytosine within the recognition sequence GCNGC and comprises less than 5 amino acid residues between amino acid residue 101 and amino acid residue 106 according to the numbering of SEQ ID NO: 33, wherein the DNA methyltransferase comprises 0-4, preferably 2-4, more preferably 3-4, 0, 1, 2, 3, 4, preferably 4, amino acid residues between amino acid residue 101 and amino acid residue 106 according to the numbering of SEQ ID NO: 33.

In another embodiment, the DNA methyltransferase comprises less than 11 amino acid residues between amino acid residue 72 and amino acid residue 83 according to the numbering of SEQ ID NO: 33.

In another embodiment, the DNA methyltransferase comprises less than 11 amino acid residues between amino acid residue 72 and amino acid residue 83 according to the numbering of SEQ ID NO: 33, wherein the DNA methyltransferase comprises at least 7, preferably at least 8 amino acid residues between amino acid residue 72 and amino acid residue 83 according to the numbering of SEQ ID NO: 33. Hence, preferably, the DNA methyltransferase comprises between amino acid residue 72 and amino acid residue 83 according to the numbering of SEQ ID NO: 33 7-10, preferably 8-10, more preferably 9-10 amino acid residues.

In another embodiment the DNA methyltransferase used in the methods of the present invention methylates DNA within the recognition sequence GCNGC resulting in DNA containing 5-methylcytosine within the recognition sequence GCNGC and comprises less than 35 amino acid residues between amino acid residue 72 and amino acid residue 106 according to the numbering of SEQ ID NO: 33 and further comprises less than 23 amino acid residues between amino acid residue 84 and amino acid residue 106 according to the numbering of SEQ ID NO: 33.

In another embodiment the DNA methyltransferase used in the methods of the present invention methylates DNA within the recognition sequence GCNGC resulting in DNA containing 5-methylcytosine within the recognition sequence GCNGC and comprises less than 35 amino acid residues between amino acid residue 72 and amino acid residue 106 according to the numbering of SEQ ID NO: 33 and further comprises less than 5 amino acid residues between amino acid residue 101 and amino acid residue 106 according to the numbering of SEQ ID NO: 33.

In another embodiment, the DNA methyltransferase further comprises less than 11 amino acid residues between amino acid residue 72 and amino acid residue 83 according to the numbering of SEQ ID NO: 33.

In a preferred embodiment the DNA methyltransferase described herein and used in the methods of the present invention methylates DNA within the recognition sequence GCNGC resulting in DNA containing 5-methylcytosine within the recognition sequence GCNGC and comprises less than 5 amino acid residues between amino acid residue 101 and amino acid residue 106 according to the numbering of SEQ ID NO: 33. Preferably, the DNA methyltransferase described herein and used in the methods of the present invention comprises 0-4, preferably 2-4, more preferably 3-4 amino acid residues between amino acid residue 101 and amino acid residue 106 according to the numbering of SEQ ID NO: 33. Preferably, the DNA methyltransferase described herein and used in the methods of the present invention comprises 0, 1, 2, 3, or 4, preferably 4 amino acid residues between amino acid residue 101 and amino acid residue 106 according to the numbering of SEQ ID NO: 33.

As shown in FIG. 1, the DNA methyltransferase described herein and used in the methods of the present invention comprises in one embodiment the following structural features with respect to the indicated amino acid positions corresponding to SEQ ID NO: 33.

| | Identifier | | | | | | | |
|---|---|---|---|---|---|---|---|---|
| | α | β | γ | δ | | ε | | |
| | Position in SEQ ID NO: 33 | | | | | | | |
| | I66 | G70 | P72 | K83 | G84 | I101 | P106 | V108 V114 |
| Comment | start of sheet | end of sheet | start of DNA-interacting loop | end of DNA-interacting loop | beginning of helix | beginning of helix | end of helix/ insert region | start end of of sheet sheet |
| | | | | | | | end of insert region | |

Thus, the DNA methyltransferase described herein and used in the methods of the present invention that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 comprises between amino acid residue 72 and amino acid residue 106 according to the numbering of SEQ ID NO: 33 a DNA interacting loop region and an alpha helix region. Preferably, the DNA interacting loop region is between amino acid residue 72 and amino acid residue 83 according to the numbering of SEQ ID NO: 33 and the alpha helix region is between residue 84 and 106 according to the numbering of SEQ ID NO: 33.

In one embodiment, the DNA methyltransferase described herein and used in the methods of the present invention that methylates DNA resulting in a DNA containing 5-methylcytosine within the recognition sequence GCNGC comprises at least 70%, at least 80%, at least 90%, or at least 95% sequence identity to SEQ ID NO: 34 and comprises a deletion between amino acid residue 72 and amino acid residue 106 according to the numbering of SEQ ID NO: 33 so that there are less than 35 amino acid residues between amino acid residue 72 and amino acid residue 106 according to the numbering of SEQ ID NO: 33. In one embodiment, the deletion is in the alpha helix region between amino acid residue 84 and 106 according to the numbering of SEQ ID NO: 33. Preferably, there is a deletion between amino acid residue 72 and amino acid residue 106 according to the numbering of SEQ ID NO: 33 of 1-20 amino acids, preferably 3-12, more preferably 4-8. Preferably, the deletion in the helix region between amino acid residue 84 and 106 according to the numbering of SEQ ID NO: 33 is a deletion of 1-15, preferably 2-10, more preferably 4-8 amino acid residues. In another embodiment, the deletion is in the DNA interacting loop region between amino acid residue 72 and 83 according to the numbering of SEQ ID NO: 33. Preferably, the deletion in the DNA interacting loop region between amino acid residue 72 and 83 according to the numbering of SEQ ID NO: 33 is a deletion of 1-6, preferably 2-4, most preferably 1-2 amino acid residues. In one embodiment, the deletion is in the alpha helix region between amino acid residue 84 and 106 according to the numbering of SEQ ID NO: 33 and in the DNA interacting loop region between amino acid residue 72 and 83 according to the numbering of SEQ ID NO: 33. Preferably, the deletion is in the alpha helix region between amino acid residue 84 and 106 according to the numbering of SEQ ID NO: 33 and in the DNA interacting loop region between amino acid residue 72 and 83 according to the numbering of SEQ ID NO: 33 is a deletion of 1-20, preferably 2-12, more preferably 4-10, most preferably 4-8 amino acid residues. Preferably, the deletion between amino acid residue 72 and amino acid residue 106 according to the numbering of SEQ ID NO: 33 does not abolish the function of the DNA interacting loop region between amino acid residue 72 and 83 according to the numbering of SEQ ID NO: 33 and does not completely remove the alpha helix region between amino acid residue 84 and 106 according to the numbering of SEQ ID NO: 33.

The DNA methyltransferase variant of SEQ ID NO: 34 comprises a DNA interacting loop region and an alpha helix region between amino acid residue 72 and amino acid residue 106 according to the numbering of SEQ ID NO: 33.

In one embodiment, the DNA methyltransferase described herein and used in the methods of the present invention that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 is selected from the group consisting of:
  (a) a DNA methyltransferase having at least 90% identity with SEQ ID NO: 33, 35, 36, 37, 38, 39, 40, 41, 42, or 43;
  (b) a DNA methyltransferase encoded by a polynucleotide having at least 80% identity with SEQ ID NO: 18, 19, 20, 21, 24, 25, 26, 27, 28, 29, 30, 31, or 32;
  (c) a DNA methyltransferase encoded by a polynucleotide that hybridizes under high stringency conditions with (i) a polynucleotide comprising SEQ ID NO: 18, 19, 20, 21, 24, 25, 26, 27, 28, 29, 30, 31, or 32, or (ii) the full-length complement of (i);
  (d) a variant of the DNA methyltransferase of SEQ ID NO: 33, 35, 36, 37, 38, 39, 40, 41, 42, or 43 comprising a substitution, deletion, and/or insertion at one or more positions and having DNA methyltransferase activity;
  (e) a DNA methyltransferase encoded by a polynucleotide that differs from SEQ ID NO: 18, 19, 20, 21, 24, 25, 26, 27, 28, 29, 30, 31, or 32 due to the degeneracy of the genetic code; and
  (f) a fragment of the DNA methyltransferase of (a), (b), (c), (d) or (e) that has DNA methyltransferase activity.

In one embodiment, the DNA methyltransferase described herein and used in the methods of the present invention that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 selected from the group consisting of:
  (a) a DNA methyltransferase having at least 55% identity with SEQ ID NO: 33;
  (b) a DNA methyltransferase encoded by a polynucleotide having at least 70% identity with SEQ ID NO: 19;
  (c) a DNA methyltransferase encoded by a polynucleotide that hybridizes under high stringency conditions with (i) a polynucleotide comprising SEQ ID NO: 19, or (ii) the full-length complement of (i);
  (d) a variant of the DNA methyltransferase of SEQ ID NO: 33 comprising a substitution, in one embodiment a conservative substitution, deletion, and/or insertion at one or more positions and having DNA methyltransferase activity;
  (e) a DNA methyltransferase encoded by a polynucleotide that differs from SEQ ID NO: 19 due to the degeneracy of the genetic code; and
  (f) a fragment of the DNA methyltransferase of (a), (b), (c), (d) or (e) that has DNA methyltransferase activity.

In one embodiment, the DNA methyltransferase described herein and used in the methods of the present invention that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 is selected from the group consisting of:
  (a) a DNA methyltransferase having at least 80%, at least 90%, at least 95%, at least 98%, or 100% identity with SEQ ID NO: 33; and
  (b) a DNA methyltransferase encoded by a polynucleotide having at least 90%, at least 95%, at least 98%, or 100% identity with SEQ ID NO: 18.

In a preferred embodiment, the DNA methyltransferase described herein and used in the methods of the present invention that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 is selected from the group consisting of:
  (a) a DNA methyltransferase having at least 80%, at least 90%, at least 95%, at least 98%, or 100% identity with SEQ ID NO: 33; and
  (b) a DNA methyltransferase encoded by a polynucleotide having at least 90%, at least 95%, at least 98%, or 100% identity with SEQ ID NO: 18;
  wherein the DNA methyltransferase comprise between amino acid residue 72 and amino acid residue 106 according to the numbering of SEQ ID NO: 33 a DNA interacting loop region and an alpha helix region. Preferably, the DNA interacting loop region is between amino acid residue 72 and amino acid residue 83 according to the numbering of SEQ ID NO: 33 and the alpha helix region is between residue 84 and 106 according to the numbering of SEQ ID NO: 33.

In one embodiment, the DNA methyltransferase described herein and used in the methods of the present invention that methylates DNA resulting in a DNA containing 5-methylcytosine within the recognition sequence GCNGC and comprises less than 23 amino acid residues between amino acid residue 84 and amino acid residue 106 according to the numbering of SEQ ID NO: 33 is selected from the group consisting of:
  (a) a DNA methyltransferase having at least 90%, at least 95%, at least 98%, or 100% identity with SEQ ID NO: 33; and
  (b) a DNA methyltransferase encoded by a polynucleotide having at least 90%, at least 95%, at least 98%, or 100% identity with SEQ ID NO: 18.

In a further preferred embodiment, the DNA methyltransferase described herein and used in the methods of the present invention that methylates DNA resulting in a DNA containing 5-methylcytosine within the recognition sequence GCNGC and comprises less than 23 amino acid residues between amino acid residue 84 and amino acid residue 106 according to the numbering of SEQ ID NO: 33 is selected from the group consisting of:
  (a) a DNA methyltransferase having at least 90%, at least 95%, at least 98% identity, or 100% with SEQ ID NO: 33; and
  (b) a DNA methyltransferase encoded by a polynucleotide having at least 90%, at least 95%, at least 98%, or 100% identity with SEQ ID NO: 18;
  wherein the DNA methyltransferase comprise between amino acid residue 84 and amino acid residue 106 according to the numbering of SEQ ID NO: 33 an alpha helix region.

In a most preferred embodiment, the DNA methyltransferase described herein and used in the methods of the present invention that methylates DNA resulting in a DNA containing 5-methylcytosine within the recognition sequence GCNGC and comprises less than 5 amino acid residues between amino acid residue 101 and amino acid residue 106 according to the numbering of SEQ ID NO: 33 is selected from the group consisting of:
  (a) a DNA methyltransferase having at least 90%, at least 95%, at least 98%, or 100% identity with SEQ ID NO: 33; and
  (b) a DNA methyltransferase encoded by a polynucleotide having at least 90%, at least 95%, at least 98%, or 100% identity with SEQ ID NO: 18.

In one embodiment, the DNA methyltransferase described herein and used in the methods of the present invention that methylates DNA resulting in a DNA containing 5-methylcytosine within the recognition sequence GCNGC and comprises less than 5 amino acid residues between amino acid residue 101 and amino acid residue 106 according to the numbering of SEQ ID NO: 33 is selected from the group consisting of:
  (a) a DNA methyltransferase having at least 90%, at least 95%, at least 98% identity, or 100% with SEQ ID NO: 33; and
  (b) a DNA methyltransferase encoded by a polynucleotide having at least 90%, at least 95%, at least 98%, or 100% identity with SEQ ID NO: 18;
  wherein the DNA methyltransferase comprise between amino acid residue 72 and amino acid residue 106 according to the numbering of SEQ ID NO: 33 a DNA interacting loop region and an alpha helix region. Preferably, the DNA interacting loop region is between amino acid residue 72 and amino acid residue 83 according to the numbering of SEQ ID NO: 33 and the alpha helix region is between residue 84 and 106 according to the numbering of SEQ ID NO: 33.

In one embodiment, the variant of the DNA methyltransferase of SEQ ID NO: 33, 35, 36, 37, 38, 39, 40, 41, 42, or 43 comprising a substitution at one or more positions and having DNA methyltransferase activity comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 substitutions. In another embodiment, the variant of the DNA methyltransferase of SEQ ID NO: 33, 35, 36, 37, 38, 39, 40, 41, 42, or 43 comprising a substitution at one or more positions and having DNA methyltransferase activity comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 conservative substitutions.

The DNA methyltransferase described herein and used in the methods of the present invention is in one embodiment a DNA methyltransferase having at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or even 100% sequence identity with SEQ ID NO: 33, 35, 36, 37, 38, 39, 40, 41, 42, or 43, wherein the DNA methyltransferase methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33.

In one embodiment, the DNA methyltransferase described herein and used in the methods of the present invention methylates DNA resulting in a DNA containing 5-methylcytosine within the recognition sequence GCNGC and further comprises less than 5 amino acid residues between amino acid residue 101 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33.

In one embodiment, the DNA methyltransferase described herein and used in the methods of the present invention methylates DNA resulting in a DNA containing 5-methylcytosine within the recognition sequence GCNGC and further comprises less than 5 amino acid residues between amino acid residue 101 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33, wherein the DNA methyltransferase comprises 0-4, preferably 2-4, more preferably 3-4, 0, 1, 2, 3, or 4, preferably 4 amino acid residues between amino acid residue 101 and amino acid residue 106 according to the numbering of SEQ ID NO: 33.

In one embodiment, the DNA methyltransferase described herein and used in the methods of the present invention further comprises less than 5 amino acid residues between amino acid residue 101 and amino acid residue 106 according to the numbering of SEQ ID NO: 33 and in another embodiment comprises less than 11 amino acid residues between amino acid residue 72 and amino acid residue 83 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or even 100% sequence identity to an amino acid sequence displayed in SEQ ID NO: 33.

In one embodiment, the DNA methyltransferase described herein and used in the methods of the present invention comprises less than 35 amino acid residues between amino acid residue 72 and amino acid residue 106 according to the numbering of SEQ ID NO: 33 and further comprises less than 5 amino acid residues between amino acid residue 101 and amino acid residue 106 according to the numbering of SEQ ID NO: 33 and comprises less than 11 amino acid residues between amino acid residue 72 and amino acid residue 83 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33.

In one embodiment, the DNA methyltransferase described herein and used in the methods of the present invention comprises less than 35 amino acid residues between amino acid residue 72 and amino acid residue 106 according to the numbering of SEQ ID NO: 33 and further comprises less than 5 amino acid residues between amino acid residue 101 and amino acid residue 106 according to the numbering of SEQ ID NO: 33 and comprises less than 11 amino acid residues between amino acid residue 72 and amino acid residue 83 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33, wherein the DNA methyltransferase methylates DNA resulting in a DNA containing 5-methylcytosine within the recognition sequence GCNGC.

In another embodiment, the DNA methyltransferase used in the present invention is defined as above, whereas the indicated sequence identity is exchanged to sequence similarity as defined herein.

In another embodiment, the DNA methyltransferase is a variant of the DNA methyltransferase of SEQ ID NO: 33, 35, 36, 37, 38, 39, 40, 41, 42, or 43 comprising a conservative substitution at one or more positions and having DNA methyltransferase activity. In another embodiment, the DNA methyltransferase is a variant of the DNA methyltransferase of SEQ ID NO: 33, 35, 36, 37, 38, 39, 40, 41, 42, or 43 comprising compared to the parent sequence only conservative substitution at one or more positions and having DNA methyltransferase activity.

In another embodiment, the DNA methyltransferase is a fragment of a DNA methyltransferase that has DNA methyltransferase activity. In one embodiment, the DNA methyltransferase is a fragment of SEQ ID NO: 33, 35, 36, 37, 38, 39, 40, 41, 42, or 43, that has DNA methyltransferase activity.

In another embodiment, the fragment of the DNA methyltransferase described herein and used in the method of the present invention has one or more amino acids deleted from the amino and/or carboxyl terminus of SEQ ID NO: 33, 35, 36, 37, 38, 39, 40, 41, 42, or 43, wherein the fragment methylates DNA within the recognition sequence GCNGC resulting in a DNA containing 5-methylcytosine within the recognition sequence GCNGC and comprises less than 35 amino acid residues between amino acid residue 72 and amino acid residue 106 according to the numbering of SEQ ID NO: 33. In another embodiment, the fragment of the DNA methyltransferase described herein and used in the method of the present invention has 1, 2, 3, 4, 5, 6, 7, 8, 9, 10, 11, 12, 13, 14, 15, 16, 17, 18, 19, or 20 amino acids deleted from the amino and/or carboxyl terminus and/or truncations of loop regions in-between. In one embodiment, a fragment of SEQ ID NO: 33, 35, 36, 37, 38, 39, 40, 41, 42, or 43 contains at least 300 amino acid residues.

The DNA methyltransferase described herein and used in the methods of the present invention is in one embodiment encoded by a polynucleotide having at least 70%, at least 75%, at least 80%, at least 85%, at least 90%, at least 91%, at least 92%, at least 93%, at least 94%, at least 95%, at least 96%, at least 97%, at least 98%, at least 99% or even 100% sequence identity with SEQ ID NO: 18, 19, 20, 21, 24, 25, 26, 27, 28, 29, 30, 31, or 32, wherein the DNA methyltransferase methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33.

In another embodiment, the DNA methyltransferase is encoded by a polynucleotide that hybridizes with (i) a polynucleotide comprising SEQ ID NO: 19, 24, 25 or 27, or (ii) the full-length complement of (i). In one embodiment, the DNA methyltransferase is encoded by a polynucleotide that hybridizes under high stringent conditions with (i) a polynucleotide comprising SEQ ID NO: 19, 24, 25 or 27, or (ii) the full-length complement of (i). In another embodiment, the stringency conditions are as described above.

In another embodiment, the DNA methyltransferase is encoded by a polynucleotide that differs from SEQ ID NO: 19, 24, 25 or 27 due to the degeneracy of the genetic code. In one embodiment, the DNA methyltransferase is encoded by a polynucleotide that differs from SEQ ID NO: 19 only due to the degeneracy of the genetic code.

Host Cells

In one embodiment, the present invention is directed to a host cell comprising the nucleic acid construct described herein. In one embodiment, the nucleic acid construct described herein is comprised in the host cell in an expression vector as described herein.

The introduction of nucleic acid into a host cell may, for instance, but not limited thereto, be effected by protoplast transformation (see, e.g., Chang and Cohen, 1979, Molecular General Genetics 168: 111-115), by using competent cells (see, e.g., Young and Spizizen, 1961, Journal of Bacteriology 81: 823-829, or Dubnau and Davidoff-Abelson, 1971, Journal of Molecular Biology 56: 209-221), by electroporation (see, e.g., Shigekawa and Dower, 1988, Biotechniques 6: 742-751), or by conjugation (see, e.g., Koehler and Thorne, 1987, Journal of Bacteriology 169: 5271-5278). Specific transformation protocols are known in the art for various types of host cells (see, e.g., for *E. coli* protoplast transformation see Hanahan, 1983, J. Mol. Biol. 166: 557-580).

Various host cells can be used for expressing the nucleic acid construct described herein. Host cells comprising the genetic constructs described herein can be obtained by one of the methods described herein for introducing the polynucleotides into such host cells.

In one embodiment, the host cell is a prokaryote or a eukaryote. In another embodiment, the host cell is a bacteria, an archaea, a fungal cell, a yeast cell or a eukaryotic cell. In another embodiment, the host cell is a non-human host cell.

In one embodiment, the host cell is a bacterial cell. The bacterial host cell may be any gram-positive bacterium or a gram-negative bacterium. Gram-positive bacteria include, but are not limited to, *Bacillus, Brevibacterium, Corynebacterium, Streptococcus, Streptomyces, Staphylococcus, Enterococcus, Lactobacillus, Lactococcus, Clostridium, Geobacillus,* and *Oceanobacillus.* Gram-negative bacteria include, but are not limited to, *Escherichia, Pseudomonas, Salmonella, Campylobacter, Helicobacter, Acetobacter, Flavobacterium, Fusobacterium, Gluconobacter.* In a specific embodiment, the bacterial host cell is a *Escherichia coli* cell. In one embodiment, the host cell is a bacterial cell. In a specific embodiment the host cell is of the genus *Escherichia* or *Bacillus.*

In the methods of the present invention, the bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus methylotrophicus, Bacillus cereus Bacillus para licheniformis, Bacillus subtilis,* and *Bacillus thuringiensis* cells. In one embodiment, the bacterial host cell is a *Bacillus amyloliquefaciens, Bacillus lentus, Bacillus* licheniformis, *Bacillus stearothermophilus* or *Bacillus subtilis* cell. In another embodiment, the bacterial host cell is a *Bacillus licheniformis* cell or a *Bacillus subtilis* cell, in a specific embodiment a *Bacillus licheniformis* cell. Preferably, the bacterial host cell is a *Bacillus licheniformis* cell. More preferred, the host cell is a *Bacillus licheniformis* ATCC 53926 cell.

In the methods of the present invention, the bacterial host cell may be *Lactobacillus acidophilus, Lactobacillus plantarum, Lactobacillus gasseri, Lactobacillus bulgaricus, Lactobacillus reuteri, Escherichia coli, Staphylococcus aureus,*

*Corynebacterium glutamicum, Corynebacterium acetoglutamicum, Corynebacterium acetoacidophilum, Corynebacterium callunae, Corynebacterium ammoniagenes, Corynebacterium thermoaminogenes, Corynebacterium melassecola, Corynebacterium effiziens, Corynebacterium efficiens, Corynebacterium deserti, Brevibacterium flavum, Brevibacterium lactofermentum, Brevibacterium divarecatum, Pseudomonas putida, Pseudomonas syringae, Streptomyces coelicolor, Streptomyces lividans, Streptomyces albus, Streptomyces avermitilis, Gluconobacter oxydans, Gluconobacter morbifer, Gluconobacter thailandicus, Acetobacter aceti, Clostridium acetobutylicum, Clostridium saccharobutylicum, Clostridium beijerinckii, Streptococcus equisimilis, Streptococcus pyogenes, Streptococcus uberis, Streptococcus equi* subsp., *Zooepidemicus* or *Basfia succiniciproducens*.

In one embodiment, the host cell does not naturally express the protein of interest. Thus, in one embodiment, the nucleic acid construct described herein is heterologous for the host cell.

In another embodiment, the bacterial host cell may additionally contain modifications, e.g., deletions or disruptions, of other genes that may be detrimental to the production, recovery or application of a polypeptide of interest. In one embodiment, a bacterial host cell is a protease-deficient cell. In another embodiment, the bacterial host cell, e.g., *Bacillus* cell, comprises a disruption or deletion of extracellular protease genes including but not limited to aprE, mpr, vpr, bpr, and/or epr. In one embodiment, the bacterial host cell does not produce spores. In another embodiment, the bacterial host cell, e.g., *Bacillus* cell, comprises a disruption or deletion of spoIIAC, sigE, and/or sigG. In one embodiment, the bacterial host cell, e.g., *Bacillus* cell, comprises a disruption or deletion of one of the genes involved in the biosynthesis of surfactin, e.g., srfA, srfB, srfC, and/or srfD. See, for example, U.S. Pat. No. 5,958,728. In another embodiment, the bacterial host cell comprises a disruption or deletion of one of the genes involved in the biosynthesis of polyglutamic acid. Other genes, including but not limited to the amyE gene, which are detrimental to the production, recovery or application of a polypeptide of interest may also be disrupted or deleted.

In another embodiment, the bacterial host cell is an *E. coli* host cell defective in the EcoKI restriction-modification systems, some in addition defective in the methylation-dependent restrictases mcrA, mcrB, mcrC, mrr, some in addition defective in dam and dcm DNA-methyltransferases. In one embodiment the *Escherichia coli* host cell that is dam- and/or dcm-methylation deficient. In another embodiment, the *Escherichia coli* host cell is recA positive.

In another embodiment the *Escherichia coli* host cell is dam- and/or dcm-methylation deficient and is recA positive.

In another embodiment, the bacterial host cell is a standard *E. coli* cloning host cell, including but not limited to DH5alpha (Invitrogen), DH10B, (Invitrogen), Omnimax (Invitrogen), INV110 (Invitrogen), TOP10 (Invitrogen), HB101 (Promega), SURE (Stratagene), XL1-Blue (Stratagen), TG1 (Lucigen), and JM109 (NEB). In another embodiment, the bacterial host cell is a standard *Bacillus subtilis* cloning host cell, including but not limited to *B. subtilis* carrying a defective hsd(RI)R-M-locus such as *B. subtilis* IG-20 (BGSC 1A436) or a defective hsdRM1 mutation such as *B. subtilis*1012 WT (Mobitec).

In one embodiment, the nucleic acid construct and/or the expression vector can be part of the chromosomal DNA or can be an extra-chromosomal DNA of the host cell. In one embodiment, the nucleic acid construct and/or the expression vector is in the host cell as a plasmid DNA, viral DNA or linear DNA.

Methods of the Invention

In another embodiment, the present invention is directed to a method of expressing a polynucleotide, comprising the steps of
(a) providing a host cell comprising a heterologous nucleic acid construct comprising a polynucleotide by introducing the nucleic acid construct comprising the polynucleotide into the host cell;
(b) cultivating the recombinant host cell of step (a) under conditions conductive for the expression of the polynucleotide; and
(c) optionally, recovering a protein of interest encoded by the polynucleotide, wherein the polynucleotide of the nucleic acid construct is operably linked to one or more control sequence that directs the expression of the polynucleotide in the host cell, wherein at least one control sequence comprises a promoter sequence of an operon comprising a secA gene or a functional fragment or functional variant thereof as described herein and wherein said promoter sequence is heterologous to the polynucleotide as described herein.

In a preferred embodiment, the promoter sequence used in the method has at least 70%, at least 75%, at least 80%, at least 85%, at least 90%, at least 92%, at least 95%, at least 98%, at least 99%, or even 100% sequence identity with SEQ ID NO: 9 and wherein the promoter sequence is preferably from a *Bacillus* species, in a specific embodiment preferably from *Bacillus licheniformis*. Preferably, the promoter sequence used in the method has at least 70% or 95% sequence identity with SEQ ID NO: 9 and wherein the promoter sequence is from a *Bacillus* species.

Preferably, the polynucleotide does not comprise a reporter gene as described herein. Preferably, the protein of interest is tolerated by the host cell only in limited quantities as described herein. Preferably, the protein of interest is selected from the group consisting of a DNA or RNA modifying enzyme as described herein.

In another embodiment, the present invention is directed to a method of expressing a polynucleotide, comprising the steps of
(a) providing a host cell comprising a heterologous nucleic acid construct comprising a polynucleotide by introducing the nucleic acid construct comprising the polynucleotide into the host cell, wherein the polynucleotide encodes for a protein of interest, wherein the protein of interest is not a reporter protein, preferably wherein the protein of interest is a DNA or RNA modifying enzyme;
(b) cultivating the recombinant host cell of step (a) under conditions conductive for the expression of the polynucleotide; and wherein the polynucleotide of the nucleic acid construct is operably linked to one or more control sequence that directs the expression of the polynucleotide in the host cell, wherein at least one control sequence comprises a promoter sequence of an operon comprising a secA gene or a functional fragment or functional variant thereof as described herein and wherein said promoter sequence is heterologous to the polynucleotide as described herein.

In another embodiment, the present invention is directed to a method of expressing a polynucleotide, comprising the steps of
(a) providing a host cell comprising a heterologous nucleic acid construct comprising a polynucleotide by introducing the nucleic acid construct comprising the polynucleotide into the host cell, wherein the polynucleotide encodes for a DNA or RNA modifying enzyme;
(b) cultivating the recombinant host cell of step (a) under conditions conductive for the expression of the polynucleotide; and wherein the polynucleotide of the nucleic acid construct is operably linked to one or more control sequence that directs the expression of the polynucleotide in the host cell, wherein at least one control sequence comprises a promoter sequence of an operon comprising a secA gene or a functional fragment or functional variant thereof as described herein and wherein said promoter sequence is heterologous to the polynucleotide as described herein.

In another embodiment, the present invention is directed to a method of expressing a polynucleotide, comprising the steps of
(a) providing a host cell comprising a heterologous nucleic acid construct comprising a polynucleotide by introducing the nucleic acid construct comprising the polynucleotide into the host cell, wherein the polynucleotide encodes for a DNA or RNA modifying enzyme;
(b) cultivating the recombinant host cell of step (a) under conditions conductive for the expression of the polynucleotide; and wherein the polynucleotide of the nucleic acid construct is operably linked to one or more control sequence that directs the expression of the polynucleotide in the host cell, wherein at least one control sequence comprises a promoter sequence of an operon comprising a secA gene and wherein said promoter sequence is heterologous to the polynucleotide as described herein.

The present invention can also be used for improving the transformation of a host cell with a second heterologous nucleic acid construct or for improving or facilitating the cultivation of a host cell that has been transformed with a second nucleic acid construct.

In another embodiment, the present invention is directed to a method of expressing a polynucleotide, comprising the steps of
(a) introducing into a host cell a first heterologous nucleic acid construct comprising a polynucleotide by introducing the first nucleic acid construct comprising the polynucleotide into the host cell, wherein the polynucleotide of the first nucleic acid construct is operably linked to one or more control sequence that directs the expression of the polynucleotide in the host cell, wherein at least one control sequence comprises a promoter sequence of an secA operon comprising a secA gene or a functional fragment or functional variant thereof as described herein and wherein said promoter sequence is heterologous to the polynucleotide as described herein;
(b) optionally, cultivating the recombinant host cell of step (a) under conditions conductive for the expression of the polynucleotide of the first nucleic acid construct; and
(c) introducing into the host cell a second heterologous nucleic acid construct comprising a polynucleotide encoding for a second protein of interest by introducing the second nucleic acid construct into the host cell, and
(d) cultivating the recombinant host cell of step (c) under conditions conductive for the expression of the polynucleotide of the first and second nucleic acid construct; and
(e) optionally, recovering a protein of interest encoded by the polynucleotide of the second nucleic acid construct.

In one embodiment, the expression of the polynucleotide of the first nucleic acid construct improves the introduction of the second nucleic acid construct into the host cell or improves or facilitates the cultivation of the host cell after transformation with the second nucleic acid construct.

In one embodiment, the polynucleotide of the first nucleic acid construct encodes for a protein of interest is tolerated by the host cell only in limited quantities as described herein. Preferably, the protein of interest is selected from the group consisting of a DNA or RNA modifying enzyme as described herein.

In one embodiment, the polynucleotide of the second nucleic acid construct encodes for a commercially relevant protein of interest, preferably, selected from the group consisting of amylase, protease, lipase, mannanase, phytase, and cellulase.

In another embodiment, the present invention is directed to a method of producing a protein of interest comprising the steps of
(a) providing a host cell comprising a heterologous nucleic acid construct comprising a polynucleotide encoding the protein of interest, wherein the polynucleotide is operably linked to one or more control sequence that directs the expression of the polynucleotide in the host cell, wherein at least one control sequence comprises a promoter sequence of an operon comprising a secA gene or a functional fragment or functional variant thereof as described herein and wherein said promoter sequence is heterologous to the polynucleotide as described herein by introducing the nucleic acid construct into the host cell;
(b) cultivating the recombinant host cell of step (a) under conditions conductive for the production of the protein of interest; and
(c) optionally, recovering a protein of interest.

In a preferred embodiment, the promoter sequence used in the methods described herein has at least 70%, at least 75%, at least 80%, at least 85%, at least 90%, at least 92%, at least 95%, at least 98%, at least 99%, or even 100% sequence identity with SEQ ID NO: 9 and wherein the promoter sequence is preferably from a *Bacillus* species, in a specific embodiment from *Bacillus licheniformis*. Preferably, the promoter sequence used in the method has at least 70% or 95% sequence identity with SEQ ID NO: 9 and wherein the promoter sequence is from a *Bacillus* species.

The host cell comprising the nucleic acid construct described herein can be obtained without being limited thereto by any of the methods for obtaining transgenic host cells described herein.

In another embodiment, the present invention is directed to a method of providing a moderate expression level of a polynucleotide, in a specific embodiment a polynucleotide encoding a protein of interest, in a host cell comprising the steps of
(a) providing a host cell comprising a heterologous nucleic acid construct comprising a polynucleotide encoding the protein of interest, wherein the polynucleotide is operably linked to one or more control sequence that directs the expression of the polynucleotide in the host cell, wherein at least one control sequence comprises a promoter sequence of an operon comprising a secA gene or a functional fragment or functional variant thereof as described herein and wherein said promoter sequence is heterologous to the polynucleotide as described herein by introducing the nucleic acid construct into the host cell;

(b) cultivating the recombinant host cell of step (a) under conditions conductive for the expression of the polynucleotide with a moderate expression level.

In another embodiment, the present invention is directed to the use of a secA promoter of an operon comprising a secA gene or a functional fragment or functional variant of the promoter as described herein for providing a moderate expression level of a polynucleotide, in a specific embodiment a polynucleotide encoding a protein of interest, in a host cell.

In another embodiment, the present invention is directed to the use of a secA promoter or a functional fragment or functional variant thereof as described herein for providing a moderate expression level of a polynucleotide, in a specific embodiment a polynucleotide encoding a protein of interest, in a host cell comprising the steps of (a) providing a host cell comprising a heterologous nucleic acid construct comprising a polynucleotide encoding the protein of interest, wherein the polynucleotide is operably linked to one or more control sequence that directs the expression of the polynucleotide in the host cell, wherein at least one control sequence comprises a promoter sequence of an operon comprising a secA gene or a functional fragment or functional variant thereof as described herein and wherein said promoter sequence is heterologous to the polynucleotide as described herein;

(b) cultivating the recombinant host cell of step (a) under conditions conductive for the expression of the polynucleotide with a moderate expression level.

In one embodiment, the protein of interest is a methyltransferase. Thus, a further embodiment is a method of producing a DNA methyltransferase, comprising the steps of (a) providing a host cell comprising a heterologous polynucleotide encoding a DNA methyltransferase wherein the DNA methyltransferase methylates DNA resulting in a DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33 as described herein;

(b) cultivating the recombinant host cell of step (a) under conditions conductive for the production of the DNA methyltransferase; and (c) optionally, recovering the DNA methyltransferase.

Cultivation of the recombinant host cell and recovering the protein of interest can be accomplished by standard prior art methods, which are further described herein.

In one embodiment, the nucleic acid construct and/or the expression vector and the host cell are as described above.

The host cells are cultivated in a nutrient medium supportive for the growth of the host cell. In one embodiment, the host cells are cultivated in a nutrient medium supportive for the growth of the host cell and for a time and under conditions suitable for expressing the polynucleotide using methods known in the art. For example, the cell may be cultivated by shake flask cultivation, small-scale or largescale fermentation (including continuous, batch, fedbatch, or solid state fermentations) in laboratory or industrial fermenters performed in a suitable medium and under conditions allowing expression of the polynucleotide. In one embodiment, the cultivation of the host cell is by fermentation in industrial scale. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

The protein of interest encoded by the polynucleotide can accumulate in the cell or can be secreted outside of the cell. The secreted polypeptide of interest can be recovered directly from the medium. The expression of the polynucleotide may be detected using methods known in the art that are specific for the polynucleotide. These detection methods may include use of PCR-based methods, hybridization based methods, specific antibodies to the encoded protein, high performance liquid chromatography, capillary chromatography, formation of an enzyme product, disappearance of an enzyme substrate, or SDS-PAGE. For example, an enzyme assay may be used to determine the activity of the enzyme. Procedures for determining enzyme activity are known in the art for many enzymes (see, for example, D. Schomburg and M. Salzmann (eds.), Enzyme Handbook, Springer-Verlag, New York, 1990). Assays for determining activity of a restriction endonuclease or DNA methyltransferase are described herein.

A protein of interest encoded by the polynucleotide may be isolated by methods known in the art. For example, a protein of interest may be isolated from the fermentation broth by conventional procedures including, but not limited to, centrifugation, filtration, extraction, spray-drying, evaporation, or precipitation. Depending on the expression construct used, the protein of interest can be secreted into the fermentation broth or can remain inside the host cell. In case of the latter, the protein of interest can be recovered from the fermentation broth by applying a step where the cells are lysed. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). The purified polypeptide may then be concentrated by procedures known in the art including, but not limited to, ultrafiltration and evaporation, in particular, thin film evaporation. In another embodiment, the protein of interest is not purified from the fermentation broth. In a specific embodiment, the protein of interest is not secreted in the fermentation broth and not recovered from the fermentation broth.

EXAMPLES

The following examples only serve to illustrate the invention. The numerous possible variations that are obvious to a person skilled in the art also fall within the scope of the invention.

Unless otherwise stated the following experiments have been performed by applying standard equipment, methods, chemicals, and biochemicals as used in genetic engineering and fermentative production of chemical compounds by cultivation of microorganisms. See also Sambrook et al. (Sambrook, J. and Russell, D. W. Molecular cloning. A laboratory manual, 3rd ed, Cold Spring Harbor Laboratory Press, Cold Spring Harbor, N Y. 2001) and Chmiel et al. (Bioprocesstechnik 1. Einführung in die Bioverfahrenstechnik, Gustav Fischer Verlag, Stuttgart, 1991).

Electrocompetent *Bacillus licheniformis* cells and electroporation

Transformation of DNA into *B. licheniformis* ATCC 53926 s performed via electroporation. Preparation of electrocompetent *B. licheniformis* ATCC 53926 cells and transformation of DNA is performed as essentially described by Brigidi et al (Brigidi, P., Mateuzzi, D. (1991). Biotechnol. Techniques 5, 5) with the following modification: Upon transformation of DNA, cells are recovered in 1 ml LBSPG buffer and incubated for 60 min at 37° C. (Vehmaanpers J., 1989, FEMS Microbio. Lett., 61: 165-170) following plating on selective LB-agar plates. If not stated differently, DNA foreign to DNA from *B. licheniformis* ATCC 53926, is in vitro methylated according to the method as described in patent DE4005025.

Plasmid Isolation

Plasmid DNA was isolated from *Bacillus* and *E. coli* cells by standard molecular biology methods described in (Sambrook, J. and Russell, D. W. Molecular cloning. A laboratory manual, 3rd ed, Cold Spring Harbor Laboratory Press, Cold Spring Harbor, N Y. 2001) or the alkaline lysis method (Birnboim, H. C., Doly, J. (1979). Nucleic Acids Res 7(6): 1513-1523). *Bacillus* cells were in comparison to *E. coli* treated with 10 mg/ml lysozyme for 30 min at 37° C. prior to cell lysis.

Plasmids

Plasmid pUK56 and pUK56S: Protease Expression Plasmid

The protease expression cassette of plasmid pCB56C (U.S. Pat. No. 5,352,604) was PCR-amplified with oligonucleotides SEQ ID NO: 1 and SEQ ID NO: 2 and the pUB110 plasmid backbone comprising repU and the kanamycin resistance gene was PCR-amplified with oligonucleotides SEQ ID NO: 3 and SEQ ID NO: 4. The PCR fragments were cut with restriction enzymes SacI and SnabI, ligated with T4-DNA ligase (NEB) following transformation into *Bacillus subtilis* 168 competent cells according to the protocol of Spizizen (Anagnostopoulos, C. and Spizizen, J. (1961). J. Bacteriol. 81, 741-746.) Correct clones of final plasmid pUK56 were analyzed be restriction enzyme digest and sequencing. The plasmid pUK56 was cut with SnaBI and the fragment of pBR322 was PCR-amplified with oligonucleotides SEQ ID NO: 5 and SEQ ID NO: 6 cut with SnabI/EcoRV (accession number pBR322 J01749.1), and cloned into pUK56 following transformation into *E. coli* XL1-Blue competent cells (Stratagene). The *E. coli/Bacillus* shuttle plasmid pUK56S with a functional SnaBI RE sites was recovered.

Plasmid pLCS3: Expression Plasmid

The low-copy origin of replication pSC101 from plasmid pZS4-Int-1 (Lutz, R. and Bujard, H. (1997); Nucleic Acids Res. 25, 1203-1210; accession number U66308) was recovered by digestion with restriction endonucleases XbaI and ScaI and cloned into pZA3PLtetO-1 luc (accession number U66309) cut with restriction endonucleases ScaI and AvrII to replace the replication origin yielding plasmid pLCS3.

Plasmid pLCS31: Expression Plasmid with Lac Repressor

The *E. coli* lac repressor gene fragment was PCR-amplified from pZS4-int1 (Lutz, R. and Bujard, H. (1997); Nucleic Acids Res. 25, 1203-1210; accession number U66308) with oligonucleotides SEQ ID NO: 7 and SEQ ID NO: 8. The PCR fragment were cut with restriction enzymes KpnI and XbaI and cloned into pLCS3 digested with KpnI and XbaI to create plasmid pLCS31.

Plasmid pLCS4: Expression Plasmid

The kanamycin resistance gene fragment (SacI/XhoI) from pZE2 PLtetO-1 MCS2 (Lutz,R. and Bujard, H. (1997); Nucleic Acids Res. 25, 1203-1210; gene accession number U66312) was cloned into pLCS3 cut with restriction endonucleases SacI/XhoI to replace the chloramphenicol resistance gene yielding plasmid pLCS4.

Plasmid pEDS3: Expression Plasmid

The synthetic DNA fragment comprising a fragment of the control region of the secA gene from *B. licheniformis* (SEQ ID NO: 9), T0 lambda terminator (Stueber, D. and Bujard, H. (1982), EMBO J. 1, 1399-1404) comprising two BsaI RE sites, flanked by XhoI and XbaI (SEQ ID NO: 10) restriction sites was cloned into pLCS3 plasmid cut with XhoI and XbaI yielding plasmid pEDS3.

Plasmid pEDT31: Expression Plasmid

The synthetic DNA fragment comprising the T5/lac promoter (SEQ ID NO: 11) from pDS56 (Stueber, D., Garotta, G. (1990), Immunological Methods, vol. IV, Academic Press, New York, pp. 121-152), T0 lambda terminator (Stueber, D. and Bujard, H. (1982), EMBO J. 1, 1399-1404) comprising two BsaI RE sites, flanked by XhoI and KpnI (SEQ ID NO: 12) restriction sites was cloned into pLCS31 plasmid cut with XhoI and KpnI yielding plasmid pEDT31.

Plasmid pMDS001-006, pMDT002-003: DNA-Methyltransferase Gene Expression Constructs The genes for the DNA-Methyltransferases were ordered as synthetic gene fragments comprising the 5'UTR/RBS of the secA gene from *B. licheniformis* (SEQ ID NO: 13), the coding sequence (cds) for the MTase gene (see sequence listing), flanked by BsaI restriction sites with compatible overhangs upon restriction for subsequent cloning into plasmid pEDS3 and pEDT31. Internal BsaI restriction sites were removed by variation of the codon-triplet.

TABLE 1

DNA-Methyltransferase expression constructs

| MTase polynucleotide (SEQ ID NO:) | Destination plasmid | MTase plasmid |
| --- | --- | --- |
| SEQ ID NO: 22 | pEDS3 | pMDS001 |
| SEQ ID NO: 23 | pEDS3 | pMDS002 |
| SEQ ID NO: 19 | pEDS3 | pMDS003 |
| SEQ ID NO: 25 | pEDS3 | pMDS004 |
| SEQ ID NO: 27 | pEDS3 | pMDS005 |
| SEQ ID NO: 24 | pEDS3 | pMDS006 |
| SEQ ID NO: 19 | pEDT31 | pMDT002 |
| SEQ ID NO: 21 | pEDT31 | pMDT003 |

Plasmid pBIL009: *Bacillus subtilis* Integration Plasmid

The plasmid pBS1C amyE integration plasmid (Radeck, J. et al. (2013). J. Biol. Eng 7, 29.) for *B. subtilis* was amplified by PCR with oligonucleotides SEQ ID NO: 14 and SEQ ID NO: 15 restricted with BsaI following cloning into the pLCS4 plasmid backbone comprising pSC101 replication origin and the kanamycin resistance gene recovered as XbaI/XhoI restriction digest fragment. The ligation mixture was transformed into *E. coli* XL1-Blue cells (Stratagene) and clones recovered on LB-agar plates containing 20 μg/ml Kanamycin. Positive clones yielding plasmid pBIL009 were analyzed by restriction digest and functional chloramphenicol resistance gene.

Plasmid pMIS012: DNA-Methyltransferase—*B. subtilis* Gene Expression Construct

The DNA-methyltransferase expression construct of pMDS003 was PCR-amplified with oligonucleotides SEQ ID NO: 16 and SEQ ID NO: 17 restricted with BamHI/XbaI following cloning into the pBIL009 plasmid backbone recovered as BamHI/XbaI restriction digest fragment. The ligation mixture was transformed into *E. coli* XL1-Blue cells (Stratagene) and clones recovered on LB-agar plates containing 20 µg/ml Kanamycin. Positive clones yielding plasmid pMIS012 were analyzed by restriction digest and functional chloramphenicol resistance gene.

Structure Prediction

Structures for the methyltransferases were predicted using the homology modelling toolkit SWISS-MODEL (Biasini M., Bienert S., Waterhouse A., Arnold K., Studer G., Schmidt T., Kiefer F., Cassarino T. G., Bertoni M., Bordoli L., Schwede T. (2014). SWISS-MODEL: modelling protein tertiary and quaternary structure using evolutionary information Nucleic Acids Research 2014 (1 Jul. 2014) 42 (W1): W252-W258) using default parameters and the following structural templates from the RCSB PDB database (Berman H. M., Westbrook J., Feng Z., Gilliland G., Bhat T. N., Weissig H., Shindyalov I. N., Bourne P. E. (2000) The Protein Data Bank Nucleic Acids Research, 28: 235-242): 2uyc_A (used for SEQ ID NO: 33 (M_Fnu4HI), SEQ ID NO: 34 (M_RBH3250), SEQ ID NO: 41 (M_CocII)), 2i9k_C (used for SEQ ID NO: 36 (M_Bsp6I), SEQ ID NO: 43 (M_LlaDII)), 3swr_A (used for SEQ ID NO: 37 (M_Cdi13307II), SEQ ID NO: 38 (M_Cdi630IV)), 1mht_C (used for SEQ ID NO: 39 (M_Ckr1771II)), 2z6u_A (used for SEQ ID NO: 40 (M_CmaLM2II)) and 9mht_C (used for SEQ ID NO: 42 (M_Fsp4HI)).

Structural Alignment

Predicted structures were structurally aligned to the predicted structure of SEQ ID NO: 33 (M_Fnu4HI) with TMalign, version 20160521 (Y. Zhang, J. Skolnick (2005), TM-align: A protein structure alignment algorithm based on TM-score, Nucleic Acids Research, 33: 2302-2309) using the default parameters.

Structure-Based Multiple Sequence Alignment

Pairwise structural alignments were combined into a multiple sequence alignment using MAFFT, version 7.221 (Katoh, S. (2013) MAFFT multiple sequence alignment software version 7: improvements in performance and usability. Molecular Biology and Evolution 30:772-780) using default parameters of the merge mode. Secondary structure annotation was added to the figure as a consensus of structural predictions.

Sequence Selection

All DNA (cytosine-5)-methyltransferases with a recognition sequence of GCNGC and that were experimentally verified with a state-of-the-art technique (determined by having 'PacBio' in their comments field) were extracted from REBASE (Roberts R J, Vincze T, Posfai J, Macelis D (2015) REBASE-a database for DNA restriction and modification: enzymes, genes and genomes. Nucleic Acids Research 43: D298-D299). To this set of methyltransferases, sequences were added for which in-house data (M.Fnu4HI and M.RBH03250) or data from literature (M.Fsp4HI (Chmuzh, E. V. and Degtiarev, S. K., 2007, Mol. Biol. (Mosk) 41, 43-50), M.Bsp6I (Lubys et al., 1995, Gene 157: 25-29), M.LlaDII (Madsen et al., 1995, Applied and Environmental Microbiology, 64(7): 2424-2431)) confirm the recognition sequences.

Example 1

Generation of Methylated DNA In Vivo in *E. coli* Cells

Competent *E. coli* INV110 cells (Invitrogen/Life technologies) were transformed with plasmid pUK65S and selected on LB-plates with 20 µg/ml Kanamycin yielding *E. coli* strain Ec #082. *E. coli* strain Ec #082 was made competent according to the method of Chung (Chung, C. T., Niemela, S. L., and Miller, R. H. (1989). One-step preparation of competent *Escherichia coli*: transformation and storage of bacterial cells in the same solution. Proc. Natl. Acad. Sci. U.S.A 86, 2172-2175) and transformed with DNA-methyltransferase encoding expression plasmids (Table 1) following selection on LB-agar plates containing 20 µg/ml kanamycin and 30 µg/ml chloramphenicol. MTase expression plasmids using the secA promoter were constructed as described above (Table 1). *Ecoli* strain name, Plasmid names and MTase genes are indicated.

TABLE 2

| E. coli Name | Plasmids | MTase polynucleotide (SEQ ID NO) | Promoter |
|---|---|---|---|
| Ec#082 | pUK56S | — | — |
| Ec#083 | pUK56S, pMDS001 | 22 | secA |
| Ec#084 | pUK56S, pMDS002 | 23 | secA |
| Ec#085 | pUK56S, pMDS003 | 19 | secA |
| Ec#086 | pUK56S, pMDS004 | 25 | secA |
| Ec#087 | pUK56S, pMDS005 | 27 | secA |
| Ec#088 | pUK56S, pMDS006 | 24 | secA |

Total plasmid DNA was isolated from the different *E. coli* strains according to standard methods in molecular biology (Sambrook, J. and Russell, D. W. Molecular cloning. A laboratory manual, 3rd ed, Cold Spring Harbor Laboratory Press, Cold Spring Harbor, N Y. 2001.) and the efficiency of in vivo methylation determined by restriction of 1 µg of total plasmid DNA with SatI (ThermoFisher Scientific) which is inhibited from cleavage by 5-methylcytosine within the recognition sequence GCNGC. Restriction reactions were analyzed by agarose gel electrophoresis with ethidium bromide staining for visualization. The Generuler 1 kb DNA Ladder (ThermoFisher Scientific) was used for estimation of DNA fragment size (FIG. 2). Plasmid DNA isolated from *E. coli* strains with GCNGC specific 5-methylcytosine DNA methylation is protected from restriction by SatI, whereas pUK56S from *E. coli* strain Ec #082 is not.

Example 2

Transformation of Methylated DNA from *E. coli* Cells into *Bacillus licheniformis*.

Plasmid DNA was isolated from *E. coli* cells Ec #082-Ec #088 as described in Example 1 and 1 µg plasmid DNA transformed into *B. licheniformis* ATCC 53926 electrocompetent cells as essentially described by Brigidi et al (Brigidi, P., Mateuzzi, D. (1991). Biotechnol. Techniques 5, 5) with the following modification: Upon transformation of DNA, cells are recovered in 1 ml LBSPG-buffer and incubated for 60 min at 37° C. (Vehmaanpers J., 1989, FEMS Microbio. Lett., 61: 165-170) following plating on LB-agar plates containing 20 µg/ml Kanamycin. LB-agar plates are incubated overnight at 37° C. and the transformation efficiency as colony-forming-units (cfu) determined. The transformation efficiencies of plasmid DNA from different *E. coli* strains were normalized against *E. coli* strain Ec #083 which was set to 100%. Note, the *E. coli* strain Ec #083 carries the *B. licheniformis* ATCC 53926 DNA methyltransferase. The *E. coli* strain Ec #084 carries a codon-optimized variant of the *B. licheniformis* ATCC 53926 DNA methyltransferase and serves as control for gene expression. Plasmid DNA pUK56S from *E. coli* Ec #082 which was not methylated by a GCNGC specific DNA methyltransferase did not recover any transformants. Surprisingly, plasmid DNA isolated from *E. coli* strains carrying MTases (Ec #85-87) heterologous to *B. licheniformis* ATCC 53926 transformed into *B. licheniformis* ATCC 53926 resulted in significantly increased transformation efficiencies (FIG. 3). Moreover, plasmid DNA isolated from the *E. coli* strain carrying the homologous MTase (Ec #88) of *B. licheniformis* ATCC 53926 with a deletion of amino acids 103-108 from SEQ ID NO: 34 (6 amino acids were truncated in total, resulting in SEQ ID NO: 35) also resulted in a significantly increased transformation efficiency compared to Ec #83.

Example 3

In Vivo Methylation in *B.Subtilis*.

The MTase expression plasmid pMIS012 for integration into the amyE gene of *B. subtilis* was linearized with restriction enzyme SacI following transformation of 2 µg of linearized plasmid DNA into *B. subtilis* 168 cells made competent according to the method of Spizizen (Anagnostopoulos, C. and Spizizen, J. (1961). J. Bacteriol. 81, 741-746.). Cells were spread and incubated overnight at 37° C. on LB-agar plates containing 10 µg/ml chloramphenicol. Grown colonies were picked and stroke on both LB-agar plates containing 10 µg/ml chloramphenicol and LB-agar plates containing 10 µg/ml chloramphenicol and 0.5% soluble starch (Sigma) following incubation overnight at 37° C. The starch plates were covered with iodine containing Lugols solution and positive integration clones identified with negative amylase activity. Genomic DNA of positive clones was isolated by standard phenol/chlorform extraction methods after 30 min treatment with lysozyme (10 mg/ml) at 37° C., following analysis of correct integration of the MTase expression cassette by PCR. The resulting *B. subtilis* strain is named Bs #053.

Plasmid pUK56 was transformed into *B. subtilis* 168 and *B. subtilis* Bs #053 cells made competent according to the method of Spizizen (Anagnostopoulos, C. and Spizizen, J. (1961). J. Bacteriol. 81, 741-746). The plasmid DNA pUK56 was in vitro methylated as described in patent DE4005025 following transformation into *B. licheniformis* ATCC 53926 electrocompetent cells as described in Example 2. Transformants were spread and incubated overnight at 37° C. on LB-agar plates containing 20 µg/ml kanamycin and 1% skim milk generating *B. subtilis* strains Bs #54 and Bs #55 and *B. licheniformis* strain Bli #112 respectively.

Plasmid DNA pUK56 was isolated from *B. subtilis* strains Bs #54 and Bs #55 and *B. licheniformis* strain Bli #112 as described in Example 1 after 30 min treatment with lysozyme (10 mg/ml) at 37° C. 1 µg plasmid DNA each was transformed into *B. licheniformis* ATCC 53926 electrocompetent cells as described in Example 2. The transformation efficiencies of plasmid pUK56 from *B. subtilis* Bs #54 and Bs #55 were normalized against the transformation efficiency of plasmid pUK56 isolated from *B. licheniformis* Bli #112 which was set to 100%. Surprisingly, plasmid DNA pUK56 isolated from *B. subtilis* Bs #55, carrying a MTase heterologous to *B. licheniformis* ATCC 53926, in comparison to plasmid DNA pUK56 isolated from *B. licheniformis* Bli #112, carrying the native *B. licheniformis* ATCC 53926 DNA methylation pattern, resulted in a significantly increased transformation efficiency (FIG. 4). In contrast, almost no colonies were recovered after transformation of plasmid pUK56 from *B. subtilis* Bs #54, which served as control.

Example 4

Promoter Studies for Expression of Heterologous MTases

DNA methyltransferases SEQ ID NO:19 and SEQ ID NO:21 were ordered as synthetic gene fragments comprising the 5'UTR/RBS region of SEQ ID NO:13 and flanking BsaI restriction sites following cloning into pEDT31 vector restricted with BsaI restriction endonuclease (NEB) and transformation into *E. coli* XL1-Blue competent cells (Stratagene), yielding the MTase expression plasmids pMDT002 and pMDT003 comprising genes encoding the methyltransferases under the control of the T5 promoter. Competent *E. coli* strain Ec #082 (Example 1) were transformed with DNA-methyltransferase encoding expression plasmids following selection on LB-agar plates containing 20 µg/ml kanamycin and 30 µg/ml chloramphenicol. The resulting *E. coli* strains are listed in the following Table 3.

TABLE 3

| E. coli Name | Plasmids | MTase (SEQ ID NO) | Promoter |
|---|---|---|---|
| Ec#089 | pUK56S, pMDT002 | 19 | T5 |
| Ec#090 | pUK56S, pMDT003 | 21 | T5 |

For plasmid preparation from *E. coli* cells Ec #089 and Ec #090 with the MTase gene under control of the commonly used T5 promoter (SEQ ID NO:11), cells were grown overnight in LB-media and MTase expression was induced with 100 µM IPTG 5 h prior to cell harvest.

For comparing the T5 promoter with the secA promoter plasmid DNA was isolated from *E. coli* Ec #082 cells expressing no methyltransferase, from *E. coli* cells expression methyltransferase under the secA promoter (Ec #085) and from *E. coli* cells expression methyltransferase under the T5 promoter (Ec #089 and Ec #090) as described in Example 1 and 1 µg total plasmid DNA transformed into *B. licheniformis* ATCC 53926 electrocompetent cells as described in Example 2. The transformation efficiencies of plasmid DNA from indicated *E. coli* strains were normalized against the pUK56S plasmid isolated from *E. coli* strain Ec #085 which was set to 100%. Plasmid DNA pUK56S from *E. coli* strain Ec #082 did not recover any transformants. Plasmid DNA pUK56S from *E. coli* strains Ec #089 and Ec #090 in comparison to Ec #085 resulted in a relative transformation efficiency of 6% and 2% respectively (FIG. 5).

These results demonstrate that compared to a well-known inducible promoter for gene expression in *E. coli*, like the T5 promoter, the use of the secA promoter for heterologous expression of a methyltransferase resulted surprisingly in an expression level not impairing with the viability of the cells and allowed continues cultivation of the cells with a methyltransferase expression level beneficial for DNA methylation and subsequently transformation efficiency.

Example 5

Extraction of *Bacillus* Species Promoters and Consensus Construction

A translated blast search using tblastn 2.5.0+(Camacho C., Coulouris G., Avagyan V., Ma N., Papadopoulos J., Bealer K., & Madden T. L. (2008) "BLAST+: architecture and applications." BMC Bioinformatics 10:421) was performed using SecA protein sequence from *Bacillus licheniformis* (protein ID WP_071583862) as a query against Genbank and Genbank WGS (Whole Genome Shotgun) databases, with options: -evalue 1e-20, -db_gencode 11, -max_target_seqs 60000. Full GenBank records were retrieved for BLAST hits above minimal protein identity 60%.

Using BLAST hit location information from the blast search results, upstream sequences of secA-coding genes were extracted, subject to the following conditions:
1. Upstream extraction size was 160 nucleotides. If there was an upstream gene/CDS annotation closer than 160 nucleotides, then a shorter fragment was extracted. If fragment length was less than 100 nucleotides, such a fragment was not extracted.
2. Extracted upstream sequences were grouped by BLAST hit bitscore, and sorted in descending order by the same bitscore. To avoid bias, identical upstream sequences from the same bitscore group were deduplicated.
3. For each of by-bitscore upstream sequence groups, a cumulative multiple alignment was performed (and saved separately) using mafft version 7.307 (Katoh, Standley. "MAFFT multiple sequence alignment software version 7: improvements in performance and usability", Molecular Biology and Evolution 30:772-780, 2013), with the keeplength option. Generated multiple nucleotide alignments were visualized as sequence logos and examined to identify the bitscore threshold at which upstream regulatory sequences conservation is the most apparent: conserved fragments still have high information content, while non-conserved fragments have low information content.
4. Based on the identified threshold, all the upstream sequences with bitscore above the threshold were multiple-aligned using mafft. Alignment was further manually refined, and consensus sequence was constructed from the alignment.
5. For *Bacillus* species, important promoter components were identified with the help of ("Compilation and analysis of *Bacillus subtilis* sigma-A-dependent promoter sequences: evidence for extended contact between RNA polymerase and upstream promoter DNA", John D. Helmann, Nucleic Acids Research, 1995, Vol. 23, No. 13 2351-2360) and ("Temporal Expression of the *Bacillus subtilis* secA Gene, Encoding a Central Component of the Preprotein Translocase", Markus Herbort, Michael Klein, Erik H. Manting, Arnold J. M. Driessen, Roland Freudl, Journal of Bacteriology, January 1999, Vol. 181, No. 2, p. 493-500).

Extraction of Enterobacteriaceae Species Promoters and Consensus Construction

For Enterobacteriaceae, the process was the same as for *Bacillus* (see above), with the following differences:
1. In *Escherichia coli*, secA gene is a part of the secM-secA operon, with a common promoter upstream of secM (secretion monitor protein). Thus, SecM protein SECM_ECOLI was used as a query for the translated BLAST search.
2. Upstream extraction size was set to 350, minimal extracted upstream length set to 50.
3. For Enterobacteriaceae species, important promoter components were identified with the help of ("Promoter element spacing controls basal expression and light inducibility of the cyanobacterial secA gene", K. Mazouni, S. Bulteau, C. Cassier-Chauvat, F. Chauvat, Molecular Microbiology, 1998, Vol. 30, No. 5, p. 1113-1122).

The invention claimed is:

1. A recombinant nucleic acid construct comprising a polynucleotide operably linked to one or more control sequence that directs the expression of the polynucleotide in a host cell, wherein at least one control sequence comprises a Bacillus secA promoter sequence and wherein said promoter sequence is heterologous to the polynucleotide, wherein the polynucleotide does not comprise a reporter gene and the polynucleotide does not comprise a secA gene, and wherein the polynucleotide encodes for a protein of interest, wherein the protein of interest is a methyltransferase.

2. The nucleic acid construct of claim 1, wherein the promoter sequence has 100% sequence identity with SEQ ID NO: 9.

3. The nucleic acid construct of claim 1, wherein the promoter sequence is from a Bacillus species.

4. The nucleic acid construct of claim 1, wherein the one or more control sequence comprises a 5'UTR sequence comprising a ribosome-binding site.

5. The nucleic acid construct of claim 1, wherein the promoter sequence is from an operon comprising a secA gene from Bacillus licheniformis.

6. The nucleic acid construct of claim 1, wherein the host cell is a Bacillus or an Escherichia cell.

7. A recombinant expression vector comprising the nucleic acid construct of claim 1.

8. A host cell comprising the nucleic acid construct of claim 1.

9. The recombinant nucleic acid construct of claim 1, wherein the methyltransferase is encoded by a polynucleotide of SEQ ID NO: 18, 19, 20, 21, 24, 25, 26, 27, 28, 29, 30, 31, or 32 or a polynucleotide differing therefrom due to the degeneracy of the genetic code.

* * * * *

SEQUENCE LISTING

<160> NUMBER OF SEQ ID NOS: 118

<210> SEQ ID NO 1
<211> LENGTH: 27
<212> TYPE: DNA
<213> ORGANISM: Artificial Sequence
<220> FEATURE:
<223> OTHER INFORMATION: PCR-amplification of fragment of pCB56C

<400> SEQUENCE: 1
aggaagagct cggtacccga cgatcat                              27

<210> SEQ ID NO 2
<211> LENGTH: 37
<212> TYPE: DNA
<213> ORGANISM: Artificial Sequence
<220> FEATURE:
<223> OTHER INFORMATION: PCR-amplification of fragment of pCB56C

<400> SEQUENCE: 2
gaggagtacg taaaatcttt ttgttccatt aaagggc                   37

<210> SEQ ID NO 3
<211> LENGTH: 30
<212> TYPE: DNA
<213> ORGANISM: Artificial Sequence
<220> FEATURE:
<223> OTHER INFORMATION: PCR-amplification of fragment of pUB110

<400> SEQUENCE: 3
gacctctacg taaccaacat gattaacaat                           30

```
<210> SEQ ID NO 4
<211> LENGTH: 30
<212> TYPE: DNA
<213> ORGANISM: Artificial Sequence
<220> FEATURE:
<223> OTHER INFORMATION: PCR-amplification of fragment of pUB110

<400> SEQUENCE: 4
ggatcgagct cccaagaaaa acacgattta                                    30

<210> SEQ ID NO 5
<211> LENGTH: 33
<212> TYPE: DNA
<213> ORGANISM: Artificial Sequence
<220> FEATURE:
<223> OTHER INFORMATION: PCR-amplification of fragment of pBR322

<400> SEQUENCE: 5
ccatgtacgt agtggcactt ttcggggaaa tgt                                33

<210> SEQ ID NO 6
<211> LENGTH: 30
<212> TYPE: DNA
<213> ORGANISM: Artificial Sequence
<220> FEATURE:
<223> OTHER INFORMATION: PCR-amplification of fragment of pBR322

<400> SEQUENCE: 6
ccaggatatc tgagcaaaag gccagcaaaa                                    30

<210> SEQ ID NO 7
<211> LENGTH: 37
<212> TYPE: DNA
<213> ORGANISM: Artificial Sequence
<220> FEATURE:
<223> OTHER INFORMATION: PCR-amplification of fragment of lacI from
      pZS4-int1

<400> SEQUENCE: 7
aggccggtac ctataaaaat aggcgtatca cgaggcc                            37

<210> SEQ ID NO 8
<211> LENGTH: 33
<212> TYPE: DNA
<213> ORGANISM: Artificial Sequence
<220> FEATURE:
<223> OTHER INFORMATION: PCR-amplification of fragment of lacI from
      pZS4-int1

<400> SEQUENCE: 8
aactcctcta gattaattgc gttgcgctca ctg                                33

<210> SEQ ID NO 9
<211> LENGTH: 41
<212> TYPE: DNA
<213> ORGANISM: Bacilllus licheniformis

<400> SEQUENCE: 9
aattgtttgg aaatgacaaa aggtatgata tgatattgca t                       41

<210> SEQ ID NO 10
<211> LENGTH: 249
<212> TYPE: DNA
<213> ORGANISM: Artificial Sequence
<220> FEATURE:
<223> OTHER INFORMATION: Synthetic DNA fragment comprising the
      B.licheniformis promoter of secA gene followed by cloning site and
```

-continued terminator

<400> SEQUENCE: 10

```
ctcgagaatt gtttggaaat gacaaaaggt atgatatgat attgcatata tcgagaccat      60
tttctccagc ctgctttcc atgcgggctg ccgcttatcg tggtctcaag cttagtgact       120
gagcttggac tcctgttgat agatccagta atgacctcag aactccatct ggatttgttc     180
agaacgctcg gttgccgccg ggcgtttttt attggtgaga atccaagcta ggttggcgag     240
atttctaga                                                             249
```

<210> SEQ ID NO 11
<211> LENGTH: 81
<212> TYPE: DNA
<213> ORGANISM: Artificial Sequence
<220> FEATURE:
<223> OTHER INFORMATION: T5-promoter with lac-operator sites

<400> SEQUENCE: 11

```
aaatcataaa aaatttattt gctttgtgag cggataacaa ttataataga ttcaattgtg     60
agcggataac aatttcacac a                                               81
```

<210> SEQ ID NO 12
<211> LENGTH: 289
<212> TYPE: DNA
<213> ORGANISM: Artificial Sequence
<220> FEATURE:
<223> OTHER INFORMATION: Synthetic DNA fragment comprising the
      T5-promoter with lac-operator sites followed by cloning site and
      terminator

<400> SEQUENCE: 12

```
ctcgagaaat cataaaaaat ttatttgctt tgtgagcgga taacaattat aatagattca     60
attgtgagcg gataacaatt tcacacaata tcgagaccat tttctccagc ctgctttcc     120 atgcgggctg ccgcttatcg tggtctcaag cttagtgact gagcttggac tcctgttgat    180
agatccagta atgacctcag aactccatct ggatttgttc agaacgctcg gttgccgccg    240
ggcgtttttt attggtgaga atccaagcta ggttggcgag attggtacc                289
```

<210> SEQ ID NO 13
<211> LENGTH: 59
<212> TYPE: DNA
<213> ORGANISM: Bacillus licheniformis

<400> SEQUENCE: 13

```
atataaaaat tactgtttac tcatgcttaa acaaggaaat taaagaggag cgttattct      59
```

<210> SEQ ID NO 14
<211> LENGTH: 39
<212> TYPE: DNA
<213> ORGANISM: Artificial Sequence
<220> FEATURE:
<223> OTHER INFORMATION: PCR-amplification of fragment of pBS1C

<400> SEQUENCE: 14

```
aggccggtct ccctagtaag gagtgtcaag aatgtttgc                            39
```

<210> SEQ ID NO 15
<211> LENGTH: 33
<212> TYPE: DNA
<213> ORGANISM: Artificial Sequence
<220> FEATURE:
<223> OTHER INFORMATION: PCR-amplification of fragment of pBS1C

<400> SEQUENCE: 15
aggccgtctc gtcgaccgtc tagccttgcc ctc					33

<210> SEQ ID NO 16
<211> LENGTH: 32
<212> TYPE: DNA
<213> ORGANISM: Artificial Sequence
<220> FEATURE:
<223> OTHER INFORMATION: PCR-amplification of fragment of pMDS003

<400> SEQUENCE: 16
aagggatccc tcgagaattg tttggaaatg ac					32

<210> SEQ ID NO 17
<211> LENGTH: 29
<212> TYPE: DNA
<213> ORGANISM: Artificial Sequence
<220> FEATURE:
<223> OTHER INFORMATION: PCR-amplification of fragment of pMDS003

<400> SEQUENCE: 17
tcctctagag ccaacctagc ttggattct						29

<210> SEQ ID NO 18
<211> LENGTH: 1053
<212> TYPE: DNA
<213> ORGANISM: Fusobacterium nucleatum 4HI

<400> SEQUENCE: 18
atgtataaag tagcaagtct ttttgcaggt gtaggtggta tagatttggg ttttgaacaa		60 acaggtcatt ttaaaacagt atgggcaaat gaatatgatg ataaagctag ggaaacattt		120 agatgtaatt tttctaataa attaaatgaa atgatataa gagaagtaga tgtacaagaa		180 attcctgata tagacatatt gttatcagga tttccttgta cttcatttag tgtagcaggt		240 tatagaaaag gctttgaaga tgaaaataca ggagattat ttttgaaac tttaagaatt		300 atagttgcaa acaacctaa agtaattttt ttagaaaatg ttaaaaattt acttggtcat		360 gataagggaa agacttttaa gataataaaa gaagctttag aaaaaaataa ttataaaata		420 aagtatcaag tattaaatgc aaaagactat ggaaatatac cacaaaatag ggaagaatc		480 tatattgttg gttttaagaa tgaagaacat tttaaaaatt ttgaatttcc tttcccatta		540 gaattaacta gaaatattga agatatgctt gaaaaaaata atatagatga aaaatattat		600 tattcaaaag aaaaaaataa attttatgat accttagaaa agaaataac taatgaaaac		660 acaatatatc agtggcgaag aagatatgta agagaaaata aagtaatgt gtgtccaaca		720 ttaactgcaa atatgggaac aggagggcat aatgtcccctt taataagagt taagaaaga		780 ataagaaaac taacaccaag agaatgtttt aattttcaag gatatcccaa ggattttaag		840 ctcccagatt tagctccttc tcacttatat aaacaagcag gaaattcagt tgtagtgcca		900 gttataaaaa gaattgcaga gaatattttc aaagcattgg aagaatttaa tgtaagttt		960 gaaataaaag taataaatta tttaaaagt aaaatatta atacatatga tgaatttta		1020 aattttattg aagaaagca aatgaagttg ttt					1053

<210> SEQ ID NO 19
<211> LENGTH: 1053
<212> TYPE: DNA
<213> ORGANISM: Artificial Sequence
<220> FEATURE:

<223> OTHER INFORMATION: Codon-variant of MTase gene of Fusobacterium
nucleatum 4HI

<400> SEQUENCE: 19

```
atgtataaag tggcatctct gtttgccggt gtaggcggta ttgaccttgg ttttgaacag      60
acaggtcatt ttaaaactgt ctgggcgaat gagtacgatg acaaagcccg cgaaactttt     120
agatgcaact tcagtaacaa actgaatgaa aacgatattc gtgaagtgga tgtccaagaa     180
attccggaca ttgatatctt gctatccggg ttcccgtgta ccagctttc tgtcgcaggc      240
taccgcaagg gctttgaaga tgaaaacacg ggagatctgt ttttcgaaac cttacggatc     300
attgttgcga acagccaaa agttatattc cttgaaaacg tgaagaacct gttaggtcat      360
gataaaggga aaaccttcaa gattatcaag gaagccttgg agaaaaataa ctataagata     420
aaataccaag tgctgaacgc gaaagactac ggcaatatcc ctcaaaatcg tgagcgcatc     480
tatatcgtgg gtttcaagaa tgaagagcac ttcaaaaatt ttgagttccc tttcccgctg     540
gagctgaccc ggaacattga agatatgctc gaaaagaaca atattgacga aaaatattac     600
tatagcaaag aaaaaaacaa attttatgat acgcttgaaa agagattac caacgaaaac      660
acgatctacc agtggcgtcg ccgttatgta cgtgaaaaca aaagtaacgt gtgtcccaca     720
ctgactgcca acatgggcac cggcggacat aatgtgccgc tgatccgtgt taagagcga      780
attcgcaaac tgacgccacg cgaatgcttt aattttcagg ggtatccgaa agattttaaa     840
ctccccgact tagcaccgtc gcacttatat aaacaggcgg gcaacagcgt agtcgtgccg     900
gttatcaaac gtattgctga aatatctttt aaagcgctcg aagagttcaa tgtttccttt     960
gagattaaag tgatcaatta cttgaagtcg aaaaacatca ataccatga tgaattcctg    1020
aacttcattg aagagaaaca gatgaagctg ttc                                 1053
```

<210> SEQ ID NO 20
<211> LENGTH: 1053
<212> TYPE: DNA
<213> ORGANISM: Artificial Sequence
<220> FEATURE:
<223> OTHER INFORMATION: Codon-variant of MTase gene of Fusobacterium
nucleatum 4HI

<400> SEQUENCE: 20

```
atgtataaag tcgcgagtct gttcgcggga gtcggcggaa ttgatcttgg ttttgagcag     60
accggccatt tcaaaactgt atgggcgaat gaatatgatg acaaagcccg cgagacgttc    120
cgttgtaatt tcagcaacaa gctgaacgaa aacgatattc gtgaagttga cgtccaggaa    180
atcccggaca ttgatatatt gctttcgggt ttcccatgca catctttcag cgttgcaggt    240
taccgcaaag ggttcgaaga tgagaacaca ggggacttat ttttcgagac tctgcgtatt    300
atcgttgcca agcagcccaa agtgatcttt ctggagaatg tgaaaaacct gttaggccac    360
gataaaggga aactttttaa aattatcaaa gaagctctgg aaaaaaacaa ttataaaatc    420
aagtaccaag ttctgaacgc gaaagactac ggtaacatcc cgcagaatcg tgaacgaatt    480
tatatcgtag gctttaaaaa tgaagagcac tttaaaaact ttgagtttcc ttttccttg     540
gagttaaccc ggaacataga ggacatgctc gaaaaaata acattgatga aaatactat     600
tactccaaag aaaaaaacaa attttatgac actctggaga agaaattac caatgaaaat     660
acgatttatc agtggcgccg cgcgctatgt gcgcgaaaaca agtctaatgt atgcccaacc    720
ctgacggcca acatgggcac gggtggccat aacgtgcccc tcatccgtgt gaagaaga     780
atccgcaaac tgaccccgcg cgaatgtttt aacttccaag gctatccgaa ggattttaaa    840
```

```
ttaccggatc ttgccccgag tcatctctac aaacaagcag gcaattccgt ggtcgtgccg      900
gtgattaagc gtattgcgga aaatatcttt aaggcactgg aggaattcaa cgtgtcgttt      960
gagatcaaag ttatcaatta cctaaagagc aagaacatta atacctacga tgaattttg     1020 aacttcatcg aggaaaaaca gatgaaactg ttc                                  1053
```

<210> SEQ ID NO 21
<211> LENGTH: 1053
<212> TYPE: DNA
<213> ORGANISM: Artificial Sequence
<220> FEATURE:
<223> OTHER INFORMATION: Codon-variant of MTase gene of Fusobacterium nucleatum 4HI

<400> SEQUENCE: 21

```
atgtataaag tggcgagctt gtttgcgggt gtgggtggta ttgatttagg ttttgaacag       60
accggtcatt ttaaaaccgt gtgggcgaac gaatatgatg ataaagcccg tgaaaccttt      120
cgctgcaact ttagtaacaa actgaacgaa acgatattc gcgaagtgga tgtgcaggaa      180
atcccagata ttgacatttt actgtcgggc tttccatgca cgtcgtttag cgtggcgggt      240
tatcgcaaag ggtttgaaga tgaaaacacc ggcgatctgt tttttgaaac gctgcgcatc      300
attgttgcga aacagccaaa agtgatcttt ctggaaaacg ttaaaaacct gttgggtcat      360
gataagggca gacgtttaa gattattaaa gaagccctgg aaaaaaacaa ctataaaatt      420
aagtatcagg tgctgaacgc gaaagactat ggcaacattc gcagaaccg tgaacgcata      480 tatatcgttg gttttaagaa cgaagaacat tttaaaaact ttgaatttcc attcccgctg      540
gaactgacgc gcaacatcga agatatgttg gaaaaaaaca acattgatga aaaatattat      600
tattcgaaag aaaaaaacaa attttatgat actctggaaa agaaattac gaacgaaaat      660 accatttatc aatggcggcg ccgctatgtg cgcgaaaaca aaagcaacgt ctgcccgacc      720
ctgacggcga acatgggcac cggcggacat aacgtaccac tgattcgcgt taagaacgc       780 attcgcaaac ttaccccgcg cgaatgcttt aactttcagg gctatcctaa ggattttaag      840
ctcccggatc tggccccaag tcacctgtat aaacaggcgg gcaactcggt tgtggtcccg      900
gttattaaac gcatcgcgga gaacatcttc aaagcgttag aagaatttaa cgtgagcttt      960
gaaattaaag tgattaacta tctgaaaagc aaaaacatca cacctatga tgaatttctg     1020 aactttatcg aagaaaagca gatgaagtta ttt                                  1053
```

<210> SEQ ID NO 22
<211> LENGTH: 1011
<212> TYPE: DNA
<213> ORGANISM: Bacillus licheniformis

<400> SEQUENCE: 22

```
atgacttatc gagtaggtag tatgtttgct gggataggtg gaacttgttt agggtttatc       60
caagctggcg ctaggattgt ctgggcaaat gaaatagaca aaaatgcttg tattacttat      120
agaaattatt ttggggatgc ttacttacaa gagggtgaca ttaacctaat agataaaaac      180
tccatacctg aactggacat tttgattgga ggttttcctt gccaagcctt ctctatagct      240
ggctatcgta aagggtttga agatgaaagg ggaaacgtgt tctttcaaat attgagggta      300
ttggaagcac aaagaaatgt ttatggacac ttaccccaag caataatgct tgagaatgta      360
aagaacttat ttcacacatga tagaggtaat acgtacagga taataaaga ggctttggaa      420 gcctttggtt ataccgtaaa agctgaggtt cttaattcaa tggaatacgg taacgtgcca      480
```

| caaaacagag agcggattta tattgtaggt tttcaagatg agagccaagc tgaaaggttt | 540 |
| agctttccag acccaattcc tttaacaaat caacttaatg atgtaattga ccgaactcgg | 600 |
| agagttgata aaagatatta ttatgatgaa acctctcaat attatgatat gttgcgagaa | 660 |
| gccatggaca gtacagatac aacttatcaa ataagacgta tatatgttcg agaaaataga | 720 |
| agcaatgttt gtcctacact gacagcgaat atgggaactg agggcataa tgttcctatt | 780 |
| gtattagact ttgaaaataa tataagaaaa ctaacaccag aagaatgctt actattgcaa | 840 |
| ggtttcccag ctgactatca ttttccagaa ggcatggcaa acactcacaa atataaacaa | 900 |
| gctggtaact ctgttacggt gccagttata agaagaattg ccactaatat tattagcgta | 960 |
| ttgaacattg aatgaatat aaatcaagaa catgaatatg caatagctga a | 1011 |

<210> SEQ ID NO 23
<211> LENGTH: 1011
<212> TYPE: DNA
<213> ORGANISM: Artificial Sequence
<220> FEATURE:
<223> OTHER INFORMATION: Codon-variant of MTase gene of Bacillus
      licheniformis

<400> SEQUENCE: 23

| atgacttatc gagtaggtag tatgtttgcc ggtattggtg gcacctgtct gggtttatt | 60 |
| caggcaggcg cacgtattgt ttgggccaat gaaattgata aaaatgcctg cattacctat | 120 |
| cgcaattatt ttggtgatgc ctatctgcaa gaaggtgata ttaatctgat tgataagaat | 180 |
| agcattccgg aactggatat tctgattggt ggttttccgt gtcaggcatt tagcattgcc | 240 |
| ggttatcgta aaggctttga agatgaacgt ggcaatgtgt tttttcagat tctggaagtg | 300 |
| ctggaagcac agcgtaatgt ttatggtcat ctgccgcagg caattatgct ggaaaatgtg | 360 |
| aaaaacctgt ttacccatga tcgtggtaat acctatcgcg tgattaaaga agcactggaa | 420 |
| gcctttggtt ataccgttaa agccgaagtt ctgaatagca tggaatatgg taatgttccg | 480 |
| cagaatcgcg aacgtattta tattgtgggc tttcaggatg aaagccaggc agaacgtttt | 540 |
| agctttccag atccgattcc gctgaccaat cagctgaatg atgtgattga tcgtacccgt | 600 |
| cgtgtggata acgctatta ttatgatgaa accagccagt attatgatat gctgcgtgaa | 660 |
| gcaatggata gcaccgatac cacctatcag attcgtcgta tttatgtgcg tgaaaatcgt | 720 |
| agcaatgttt gtccgacccct gaccgcaaat atgggcaccg tggtcataa tgttccgatt | 780 |
| gtgctggatt ttgaaaataa tattcgcaaa ctgacaccgg aagaatgtct gctgctgcaa | 840 |
| ggttttccgg cagattatca ttttccggaa ggtatggcca tacccataa atacaaacag | 900 |
| gcaggcaata cgttaccgt tccggttatt cgtcgcattg ccaccaatat tatttccgtg | 960 |
| ctgaatattg gcatgaatat taatcaggaa catgaatacg ccatcgccga a | 1011 |

<210> SEQ ID NO 24
<211> LENGTH: 993
<212> TYPE: DNA
<213> ORGANISM: Artificial Sequence
<220> FEATURE:
<223> OTHER INFORMATION: Truncated variant of Bacillus licheniformis
      Mtase with deletion of 6 amino acids

<400> SEQUENCE: 24

| atgacttatc gagtaggtag tatgtttgct gggataggtg gaacttgttt agggtttatc | 60 |
| caagctggcg ctaggattgt ctgggcaaat gaaatagaca aaaatgcttg tattacttat | 120 |

| | |
|---|---|
| agaaattatt ttggggatgc ttacttacaa gagggtgaca ttaacctaat agataaaaac | 180 |
| tccatacctg aactggacat tttgattgga ggttttcctt gccaagcctt ctctatagct | 240 |
| ggctatcgta aagggtttga agatgaaagg ggaaacgtgt tctttcaaat attagaggta | 300 |
| ttggaaggac acttaccccca agcaataatg cttgagaatg taaagaactt atttacacat | 360 |
| gatagaggta atacgtacag agtaataaaa gaggctttgg aagcctttgg ttataccgta | 420 |
| aaagctgagg ttcttaattc aatggaatac ggtaacgtgc cacaaaacag agagcggatt | 480 |
| tatattgtag gttttcaaga tgagagccaa gctgaaaggt ttagctttcc agacccaatt | 540 |
| cctttaacaa atcaacttaa tgatgtaatt gaccgaactc ggagagttga taaaagatat | 600 |
| tattatgatg aaacctctca atattatgat atgttgcgag aagccatgga cagtacagat | 660 |
| acaacttatc aaataagacg tatatatgtt cgagaaaata aagcaatgt ttgtcctaca | 720 |
| ctgacagcga atatgggaac tggagggcat aatgttccta ttgtattaga ctttgaaaat | 780 |
| aatataagaa aactaacacc agaagaatgc ttactattgc aaggtttccc agctgactat | 840 |
| cattttccag aaggcatggc aaacactcac aaatataaac aagctggtaa ctctgttacg | 900 |
| gtgccagtta taagaagaat tgccactaat attattagcg tattgaacat tggaatgaat | 960 |
| ataaatcaag aacatgaata tgcaatagct gaa | 993 |

<210> SEQ ID NO 25
<211> LENGTH: 945
<212> TYPE: DNA
<213> ORGANISM: Bacillus sp. RFL6

<400> SEQUENCE: 25

| | |
|---|---|
| atgttacaaa tagcaagttt attcgcaggt gtaggtggaa ttgatttagg atttgaacaa | 60 |
| actggatatt ttgaaacggt ttgggcaaat gaatatgata aaaatgcagc tattacctat | 120 |
| caatcaaatt ttaaaaacaa attaattata gatgatattc gaaatatcaa agtagaagat | 180 |
| gttcctgatt ttgatgtttt attatcagga tttccttgta cttcttttag cgtggctgga | 240 |
| tatagaaaag gctttgaaga tgaaaaaagc ggagatttat ttttgaaac tttacgcttg | 300 |
| attgtagcta aaaaaccaca agttatattt ttagaaaatg ttaaaaatct tgtgggtcat | 360 |
| gacaacggaa ataccttaa agtcatttat gaagcgttag aaagcaacgg atatcatata | 420 |
| aaataccaag ttctaaacgc aaaagatttt gggaatatac ctcaaaatag agagcgtatc | 480 |
| tatattgtag gttttaggaa tattgaacac tataaaaatt ttaattttcc gatgccacaa | 540 |
| ccacttacat taacaataaa agatatgata aatcttttcag ataaactaga tgatagattt | 600 |
| tattatacag aggataaatg ttcttttttat tcacctttac aagaacaaat gacttcagat | 660 |
| gaaacaatat atcaatggcg tagaaaatat gtgagagaaa acaaaagtaa tgtatgccct | 720 |
| acgttaactg cgaacatggg aactggagga cataatgttc cattagttaa aacaaaacat | 780 |
| ggaattagaa agttgactcc tagagagtgt ttcaattttc aaggttatcc tgaagatttc | 840 |
| attttacccg aattggctcc tacgcatctt tataagcaag ctggaaattc tgttgttgtt | 900 |
| cctgtcataa gacgcatagc agaaaatatt tataaatcta tgttg | 945 |

<210> SEQ ID NO 26
<211> LENGTH: 1224
<212> TYPE: DNA
<213> ORGANISM: Flavobacterium sp. 4H

<400> SEQUENCE: 26

| | |
|---|---|
| atgagtttaa aacagacaat aagtattaat gaatttgacg gcaaaagcta tcaaattaga | 60 |

```
cttgttgaag gtattgaaga caaagccgtt ttaacacatt atcttcataa ctatagaaat      120
ggtgtaaaaa agcattacga aaaagatgct atttcaactc taaaaaattt cgtagaatat      180
aaacaagagg aaactgaatt acctattgtt gcagaagatg ctttgcaaca acttttattt      240
gaagttgaaa acgtaccttt tccaactcca gaaaattata gctttaaatt cattgattta      300
tttgcaggaa ttggaggatt tagattagcg ttacaaaatg ttggcggaaa gtgtgttttt      360
acaagcgaat ggaataatga agctcaaaaa acttatcgag aaaattttgg agaagttccg      420
tttggcgaca taacaaaaga gcgaaataaa aattatattc ctgaaaaatt tgacatttta      480
tgtgcaggtt ttccttgcca agcatttttca attgctggtt atcagaaagg ttttgctgac      540
```
cttgttgaag gtattgaaga caaagccgtt ttaacacatt atcttcataa ctatagaaat      120
ggtgtaaaaa agcattacga aaaagatgct atttcaactc taaaaaattt cgtagaatat      180
aaacaagagg aaactgaatt acctattgtt gcagaagatg ctttgcaaca acttttattt      240
gaagttgaaa acgtaccttt tccaactcca gaaaattata gctttaaatt cattgattta      300
tttgcaggaa ttggaggatt tagattagcg ttacaaaatg ttggcggaaa gtgtgttttt      360
acaagcgaat ggaataatga agctcaaaaa acttatcgag aaaattttgg agaagttccg      420
tttggcgaca taacaaaaga gcgaaataaa aattatattc ctgaaaaatt tgacatttta      480
tgtgcaggtt ttccttgcca agcatttttca attgctggtt atcagaaagg ttttgctgac      540
acaagaggaa ctttattttt tgacattgag caaattgtag aaaaacataa acccaaggtt      600
gtatttttag aaaatgtaaa aaaccttgtt tctcacgaca atggaaatac atttaaaaca      660
attattgaaa cacttgaact aaaattgggt tataaaacat ttgcaaaagt tttaaattca      720
gcaactcacg caaatgttcc gcaaaatcgt gagcgaattt ttattgttgc atttgaccca      780
aaacaagtga aaaattattc aaaattcgag tttcctaaac caatcaaatt aacaaaaaca      840
attcacgact ttttggataa agaaaagcaa gatgatattt tttattacaa aaaagaccat      900
caatattatc ctgaacttgt aaaaacaatg atttcaaaag atacggttta tcaatggaga      960
agagtttatg caagagaaaa caaaagtaac ctttgcccta ctctaacggc aaatatgggt     1020
tctggcggac ataatgtacc attgattata gacgattttg gaattagaaa actaactcca     1080
aaagaatgtt ttgcgttcca aggttatcca atcgaaaaat atattattcc aaaacttgca     1140
aatagtaaac tttatatgca agctggaaat tctgtaacga caaatttaat tgaaagaatt     1200
gcaaatcaaa taattgaagt ttta                                            1224

<210> SEQ ID NO 27
<211> LENGTH: 951
<212> TYPE: DNA
<213> ORGANISM: Lactococcus lactis W39

<400> SEQUENCE: 27
atgttgaaaa ttgcttcttt tttcgccgga gttggcggaa ttgatttagg ttttgaaaat       60
gcaggtttca aaacaatata tgctaatgaa tttgataatt atgctgctga tacttttgaa      120
atgaactttg acgttaaggt agaccgacgt gatataaatg atgtacaagc tgatgaaata      180
ccagattttg atattatgtt agcaggtttt ccttgccaag cctttttctat tgctggttat      240 cgtcaaggct ttaacgatga acaaggtcga ggtaatcttt tttttgaact tgttcgtatt      300
ttagaaacaa aaaaacctcg tgttgcattc tttgaaaatg ttaaaaatct tgtttctcac      360
gatagcggga acacatttag agttatttgt tctgagttag aaagactagg gtacaagtat      420 cttttttcaag tgtttaatgc ttctgaatat ggaaatatac ctcaaaatag agaacgtatc      480
tatattgttg ctttcaaaaa taaaaaagat tatgcaaatt ttgaactacc aaaatctata      540
cctttaaaaa caacgattca cgatgttatt gattttttcta aaaacaagac gataagttc      600 tactatacct ctgaaaagaa taaattttttt gatgagttaa agaaaaatat gactaatcac      660
gacactacat atcagtggcg tagagtttat gtaagagaaa acaaaagtaa tttagtacca      720
acactaacgg ctaatatggg aacaggtggg cataatgtgc ctataatcct tacatatagc      780
ggagatattc gtaaattaac accaagagaa tgctttaacg ttcaaggttt cccaaaagaa      840
tataaacttc caaaccaaag taatgggaga ttatataaac aagcaggaaa cagtgttgta      900

```
gtaccagtta tagaaagaat tgcaaaaaat cttgcagata ctatagtcga a          951

<210> SEQ ID NO 28
<211> LENGTH: 1623
<212> TYPE: DNA
<213> ORGANISM: Clostridium difficile

<400> SEQUENCE: 28
atgtataatg ttatagatct ttttgcaggt gcaggtggtt tgagcttagg atttgaaatg     60
actaaaaaat ttaatatggt ggcttttgta gaaaaaaatg ataacgcagc aaaaacatac    120
cttgaaaatc atccgagtgt taagcgttat tgtgatatta aagattaga ttttcaagat     180 atattaaaca gtgtcgataa gatagatgtt gttataggag gaccgccatg tcaaggtttt    240
tctaatgcta atagacaaaa aagaaaaatt ataaatggaa ataatgaatt agttaagcta    300
tatgttgatg ctattgataa attaaagcca aatgtatttg taatggaaaa tgtcaaaact    360
atatcttcaa ataagcattc atttatttg actaaaaaag ataaaaatca tataataaat     420
aatttaaaat taaatattta taataaagat agtgttttat atgatagaac tgagtatata    480
aatgaattat ttaatattat tagtatagaa gatattgaat catatattat atcaaatata    540
gacttaaaaa atttgaaaat aattattaag aaaaaaaagg atatatgtga ttatttaaat    600
aaaatatcta attataagaa agtaaaatct accatagaaa aattggaaac aaggggaaaa    660
atgccaaaat ggtatttaga attaataaat aaagtaaaaa atattattaga aaatatgtta    720 tataatagaa atttatcaga tgaacaaata ttttatttga acttattctt ggatattcaa    780
aatttatttt taggaatata tgagttaaaa tctgaatctg taattttcga aaatacactt    840
gatgataata aaattatagc taaaatggat acttacatta taatagatta tataaatgca    900
tcctttgagt atctaggata tgtattaaat ggaagtgcac taaattcaat tgattatgga    960
gtacctcaaa atagagaaag atttgtattg ataggagcaa aaaagactt cttaaaaaat    1020 aaaagatag aaactcctaa gcctatagtt ggagaaaatt atgttacagt aagagatgca    1080
ataggcgatt tagctgaata tgaggcttct aaaggtagta tggattattg ttttgaaaaa    1140
aatagtaata atattgaaaa agatttttat agaaagataa tattggatag caataaaata    1200
tacaatcatg tatgtacaga tacaagaaat atcgcactaa aaagatttga atatataaat    1260
caaggaaata atttcatc tttgccagat gagttaaaag aacttatgc tgatccagaa       1320 agaactcaaa atactattta taaaagacta gtatatgata agccatcaga tactgttgta    1380
aatgtaagaa atctatgtg gatacatcct attaaaaaca gagctgttag cgcaagagag    1440
gcggctagat tgcagtcatt ccctgatagt tataagtttt taggtacaaa agattctgta    1500
tatcaacaga taggaaatgc agtaccacct ttattaggtc gagtagtagc agaaaagata    1560
ttaaatttat ttaatgatga accaaatgag tatcttagag atgtgtttga agcactagat    1620
gga                                                                1623

<210> SEQ ID NO 29
<211> LENGTH: 1623
<212> TYPE: DNA
<213> ORGANISM: Clostridium difficile 630

<400> SEQUENCE: 29
atgtataatg ttatagatct ttttgcaggt gcaggtggtt tgagcttagg atttgaaatg     60
actaaaaaat ttaatatggt ggcttttgta gaaaaaaatg ataacgcagc aaaaacatac    120
cttgaaaatc atccgagtgt taagcgttat tgtgatatta aagattaga ttttcaagat     180
```

```
atattaaaca gtgtcgataa gatagatgtt gttataggag gaccgccatg tcaaggtttt    240
tctaatgcta atagacaaaa aagaaaaatt ataaatggaa ataatgaatt agttaagcta    300
tatgttgatg ctattgataa attaaagcca aatgtatttg taatggaaaa tgtcaaaact    360
atatcttcaa ataagcattc attttatttg actaaaaaag ataaaaatca tataataaat    420
aatttaaaat taaatattta taataaagat agtgttttat atgatagaac tgagtatata    480
aatgaattat ttaatattat tagtatagaa gatattgaat catatattat atcaaatata    540
gacttaaaaa atttgaaaat aattattaag aaaaaaaagg atatatgtga ttatttaaat    600
aaaatatcta attataagaa agtaaaatct accatagaaa aattggaaac aaggggaaaa    660
atgccaaaat ggtatttaga attaataaat aaagtaaaaa atatattaga aaatatgtta    720
tataatagaa atttatcaga tgaacaaata ttttatttga acttattctt ggatattcaa    780
aatttatttt taggaatata tgagttaaaa tctgaatctg taattttcga aaatacactt    840
gatgataata aaattatagc taaaatggat acttacatta aatagatta tataaatgca    900 tcctttgagt atctaggata tgtattaaat ggaagtgcac taaattcaat tgattatgga    960
gtacctcaaa atagagaaag atttgtattg ataggagcaa aaaagactt cttaaaaaat   1020 aaaaagatag aaactcctaa gcctatagtt ggagaaaatt atgttacagt aagagatgca   1080
ataggcgatt tagctgaata tgaggcttct aaaggtagta tggattattg ttttgaaaaa   1140
aatagtaata atattgaaaa agattttat agaaagataa tattggatag caataaaata   1200
tacaatcatg tatgtacaga tacaagaaat atcgcactaa aaagatttga atatataaat   1260
caaggaaata atttcattc tttgccagat gagttaaaag gaacttatgc tgatccagaa   1320
agaactcaaa atactattta taaaagacta gtatatgata agccatcaga tactgttgta   1380
aatgtaagaa aatctatgtg gatacatcct attaaaaaca gagctgttag cgcaagagag   1440
gcggctagat tgcagtcatt ccctgatagt tataagtttt taggtacaaa agattctgta   1500
tatcaacaga taggaaatgc agtaccacct ttattaggtc gagtagtagc agaaaagata   1560
ttaaatttat ttaatgatga accaaatgag tatcttagag atgtgtttga agcactagat   1620
gga                                                                 1623

<210> SEQ ID NO 30
<211> LENGTH: 957
<212> TYPE: DNA
<213> ORGANISM: Caldicellulosiruptor kristjanssonii 177R1B

<400> SEQUENCE: 30
gtgattaaaa taagagtagt aagtttgttt tctggagttg gtggtatttg cttagctttc     60
aaacaagcag gatttgatgt gatttgggca aatgatattg ataagtatgc ttgtataaca    120
tatagatcta atttcccaac agtagagctt gttgaaggtg atatacaaag tattgattcc    180
aataatatac ctgaatgtga tatcattaca gcaggatttc cttgccaacc ttttttctatt   240 gcaggttatc agagaggtct caatgaccct cgtggaagac tattttatga aattgttcgt    300
atcgttcatg ataaaaagcc aaaaattatt tttctcgaaa atgtaaaaaa tcttgtttca    360
cataacaacg ggattacctt taaaaatatt ttaaatgctc tggaaaatga gggatactat    420
ttaaagtatg ctgtgcttaa ttctttagaa tacggtaatg taccctcaaaa tagggaaagg    480 gtttatatag taggtttttt agataaatca atgtatgaag catttaagtt tccagaacca    540
gtatcactaa cagttactat tcacgatatt attaagccat gggagaaaaa agacgaaaag    600
```

```
tattactaca gagaagggaa gtattatgaa cttctcaaac aaaatgtaga tgaccctaat    660
acagtttatc agataaggcg tatatatgtc agaaaaaata gaagggtgt atgtcctact     720 ttaactgcaa acatgggtga aggtggtcat aatgttccta tcgtaatgga taactatgga   780
tttagaaaat tgaccccacg agaatgtttc atactacaag gcttcccaga agattttgta   840
ctaccttcag gtttagcaga ttctaagttg tataaacaag caggtaatgc cgttactgta   900
acagttgtaa agcgtattgc agataaaata ttggaaactt gtcttgtaaa atcaata      957
```

<210> SEQ ID NO 31
<211> LENGTH: 1218
<212> TYPE: DNA
<213> ORGANISM: Clostridium mangenotii LM2

<400> SEQUENCE: 31

```
atgactaaaa acaatgatgc tgtaagtacc aaaaactata ctgtagcaag tttttttcggt    60 ggagttggcg gtattgactt aggatttgaa caagctaaga agttcagtac ggtttacatt    120
aatgaattcg ataaaaatgc acaggagaca atatctataa atttccctag ggttagtcta    180
gatagacgag atatacatga agtaagggta gatgaagtgc caagtactga tatagttgcc    240
gggggatttc catgtcaagc tttctcgata gcagggtata gaaaaggatt tgaagatgaa    300
agaggagacc tgttttttga acttttaagg attataaaac atcataagcc aaaagttata   360
ttcatagaga atgtaaaaaa tatggttaca catgatcatg aaatacatt taaggtaata    420 agagaagctt taactttaaa tggatactat ataaaatgga agtcataaa tggaaaagat   480 tatggtgata ttcctcaaaa tagagaacgt atatatataa ctggattttt agataaaaat   540
gcttttgatg aatttgaatt tccgaataaa atagaactga ctaatggatt agatacagta   600
atagatttta aagctaaggt agaggataag tactactata gacaaggtat ccaaccattt   660
tatgataagc tagaagaaac tataacatct caaaattcag tttatcaatg gagaaggcaa   720
tatgttagag agaacaaaag tggagtagta ccaactctaa ctgctaacat gggaactgga   780
gggcataatg taccccttat tctatcatac tatggaataa gaaaattgac tccaagggaa   840
acttttaata ttcaaggatt tccaacggat tttaaattac ctgaaatttc aaatgctcag   900
ttatataaac aagcagggaa tagtgttgta gtaccagtta ttaaacgtat agcagaaaat   960
atagctaatg cattagaaga agcagagaat aagaatgaaa tatataatac tgtagaagaa  1020
aataataaaa atatacttat atatgtagat atgaaaagca ggtttgaagg agagagcttt  1080
gtgcaagcct actttgatga agttgtgaa gctaacgact ttgcaattat aacagaaatt    1140 ccaatttat cagatgaaga atatctaaag cttgtaaaaa gaaatgtatc aaagcgtttt  1200
tattcattac aaactaag                                                1218
```

<210> SEQ ID NO 32
<211> LENGTH: 954
<212> TYPE: DNA
<213> ORGANISM: Capnocytophaga ochracea DSM 7271

<400> SEQUENCE: 32

```
atgggaaaaa gcgttaaatt catagattta tttgcagggg tagggggctt ccgctatgct     60
ttgcagaata taggggctga atgtgtcttt tcgtcagaat gggacaagtt cgctcagcaa    120
acctataagc taaactatgg agaagttcct tttggcgata ttactttaca agaaacgaaa    180
gataatattc ctaatgaatt tgatatactt tgcgcaggat ttccttgtca agcatttttct   240 atagctggat atcaaaaagg ttttgaagat attaggggaa cactttttttt tgagatagaa   300
```

-continued

```
gaaatagtaa ggaagcatcg tcctaaggtt attttttag aaaatgtaaa gaacttagtg    360
agtcacgata agggtaaaac atttaaggta ataacgaata tcttagaaga gaaattaggt    420
tacaagatat tttataaagt cctcaataca atggaatatg ctaatattcc acaaaataga    480
gagcgtattt ttatagtagc ttttgatcct aaacaagttc ctaattataa agagttccaa    540
tttcctgaaa aaattaaact tactaaaacg attcatagct ttttagagaa aggaaaacag    600
aatgattatt tttattatca gctatctcac aaatacagtc cagaacttat taaaatagta    660
acacgtaaag atactattta tcaatggagg cgtgtgtatg ttcgagaaaa taagaacaat    720
gtttgtccta ctttaacagc taatatgggt acaggggggac ataatgtacc gattattaaa    780
gataattttg gtattaggaa gttaaccccca cgagaatgtt ttaattttca aggttatcca    840
aaaggcttta ctttctaa agaaatagct atatcaaaat tatatatgca ggcagggaac     900
tctgtgacaa tgcctttaat tcaaagagta agtgaacaaa ttttgaaagt gtta         954
```

<210> SEQ ID NO 33
<211> LENGTH: 351
<212> TYPE: PRT
<213> ORGANISM: Fusobacterium nucleatum 4HI

<400> SEQUENCE: 33

```
Met Tyr Lys Val Ala Ser Leu Phe Ala Gly Val Gly Gly Ile Asp Leu
1               5                   10                  15

Gly Phe Glu Gln Thr Gly His Phe Lys Thr Val Trp Ala Asn Glu Tyr
            20                  25                  30

Asp Asp Lys Ala Arg Glu Thr Phe Arg Cys Asn Phe Ser Asn Lys Leu
        35                  40                  45

Asn Glu Asn Asp Ile Arg Glu Val Asp Val Gln Glu Ile Pro Asp Ile
    50                  55                  60

Asp Ile Leu Leu Ser Gly Phe Pro Cys Thr Ser Phe Ser Val Ala Gly
65                  70                  75                  80

Tyr Arg Lys Gly Phe Glu Asp Glu Asn Thr Gly Asp Leu Phe Phe Glu
                85                  90                  95

Thr Leu Arg Ile Ile Val Ala Lys Gln Pro Lys Val Ile Phe Leu Glu
            100                 105                 110

Asn Val Lys Asn Leu Leu Gly His Asp Lys Gly Lys Thr Phe Lys Ile
        115                 120                 125

Ile Lys Glu Ala Leu Glu Lys Asn Asn Tyr Lys Ile Lys Tyr Gln Val
    130                 135                 140

Leu Asn Ala Lys Asp Tyr Gly Asn Ile Pro Gln Asn Arg Glu Arg Ile
145                 150                 155                 160

Tyr Ile Val Gly Phe Lys Asn Glu Glu His Phe Lys Asn Phe Glu Phe
                165                 170                 175

Pro Phe Pro Leu Glu Leu Thr Arg Asn Ile Glu Asp Met Leu Glu Lys
            180                 185                 190

Asn Asn Ile Asp Glu Lys Tyr Tyr Ser Lys Glu Lys Asn Lys Phe
        195                 200                 205

Tyr Asp Thr Leu Glu Lys Glu Ile Thr Asn Glu Asn Thr Ile Tyr Gln
    210                 215                 220

Trp Arg Arg Arg Tyr Val Arg Glu Asn Lys Ser Asn Val Cys Pro Thr
225                 230                 235                 240

Leu Thr Ala Asn Met Gly Thr Gly Gly His Asn Val Pro Leu Ile Arg
                245                 250                 255
```

```
Val Lys Glu Arg Ile Arg Lys Leu Thr Pro Arg Glu Cys Phe Asn Phe
            260                 265                 270

Gln Gly Tyr Pro Lys Asp Phe Lys Leu Pro Asp Leu Ala Pro Ser His
        275                 280                 285

Leu Tyr Lys Gln Ala Gly Asn Ser Val Val Pro Val Ile Lys Arg
    290                 295                 300

Ile Ala Glu Asn Ile Phe Lys Ala Leu Glu Glu Phe Asn Val Ser Phe
305                 310                 315                 320

Glu Ile Lys Val Ile Asn Tyr Leu Lys Ser Lys Asn Ile Asn Thr Tyr
                325                 330                 335

Asp Glu Phe Leu Asn Phe Ile Glu Glu Lys Gln Met Lys Leu Phe
        340                 345                 350

<210> SEQ ID NO 34
<211> LENGTH: 337
<212> TYPE: PRT
<213> ORGANISM: Bacillus licheniformis

<400> SEQUENCE: 34

Met Thr Tyr Arg Val Gly Ser Met Phe Ala Gly Ile Gly Gly Thr Cys
1               5                   10                  15

Leu Gly Phe Ile Gln Ala Gly Ala Arg Ile Val Trp Ala Asn Glu Ile
                20                  25                  30

Asp Lys Asn Ala Cys Ile Thr Tyr Arg Asn Tyr Phe Gly Asp Ala Tyr
            35                  40                  45

Leu Gln Glu Gly Asp Ile Asn Leu Ile Asp Lys Asn Ser Ile Pro Glu
        50                  55                  60

Leu Asp Ile Leu Ile Gly Gly Phe Pro Cys Gln Ala Phe Ser Ile Ala
65                  70                  75                  80

Gly Tyr Arg Lys Gly Phe Glu Asp Glu Arg Gly Asn Val Phe Phe Gln
                85                  90                  95

Ile Leu Glu Val Leu Glu Ala Gln Arg Asn Val Tyr Gly His Leu Pro
            100                 105                 110

Gln Ala Ile Met Leu Glu Asn Val Lys Asn Leu Phe Thr His Asp Arg
        115                 120                 125

Gly Asn Thr Tyr Arg Val Ile Lys Glu Ala Leu Glu Ala Phe Gly Tyr
    130                 135                 140

Thr Val Lys Ala Glu Val Leu Asn Ser Met Glu Tyr Gly Asn Val Pro
145                 150                 155                 160

Gln Asn Arg Glu Arg Ile Tyr Ile Val Gly Phe Gln Asp Glu Ser Gln
                165                 170                 175

Ala Glu Arg Phe Ser Phe Pro Asp Pro Ile Pro Leu Thr Asn Gln Leu
            180                 185                 190

Asn Asp Val Ile Asp Arg Thr Arg Arg Val Asp Lys Tyr Tyr Tyr
        195                 200                 205

Asp Glu Thr Ser Gln Tyr Tyr Asp Met Leu Arg Glu Ala Met Asp Ser
    210                 215                 220

Thr Asp Thr Thr Tyr Gln Ile Arg Arg Ile Tyr Val Arg Glu Asn Arg
225                 230                 235                 240

Ser Asn Val Cys Pro Thr Leu Thr Ala Asn Met Gly Thr Gly Gly His
                245                 250                 255

Asn Val Pro Ile Val Leu Asp Phe Glu Asn Asn Ile Arg Lys Leu Thr
            260                 265                 270

Pro Glu Glu Cys Leu Leu Leu Gln Gly Phe Pro Ala Asp Tyr His Phe
        275                 280                 285
```

```
Pro Glu Gly Met Ala Asn Thr His Lys Tyr Lys Gln Ala Gly Asn Ser
    290                 295                 300

Val Thr Val Pro Val

Arg Arg Ile Ala Thr Asn Ile Ser Val Leu Asn Ile Gly Met Asn
305                 310                 315                 320

Ile Asn Gln Glu His Glu Tyr Ala Ile Ala Glu
                325                 330

<210> SEQ ID NO 36
<211> LENGTH: 315
<212> TYPE: PRT
<213> ORGANISM: Bacillus sp. RFL6

<400> SEQUENCE: 36

Met Leu Gln Ile Ala Ser Leu Phe Ala Gly Val Gly Gly Ile Asp Leu
1               5                   10                  15

Gly Phe Glu Gln Thr Gly Tyr Phe Glu Thr Val Trp Ala Asn Glu Tyr
                20                  25                  30

Asp Lys Asn Ala Ala Ile Thr Tyr Gln Ser Asn Phe Lys Asn Lys Leu
            35                  40                  45

Ile Ile Asp Asp Ile Arg Asn Ile Lys Val Glu Asp Val Pro Asp Phe
50                  55                  60

Asp Val Leu Leu Ser Gly Phe Pro Cys Thr Ser Phe Ser Val Ala Gly
65                  70                  75                  80

Tyr Arg Lys Gly Phe Glu Asp Glu Lys Ser Gly Asp Leu Phe Phe Glu
                85                  90                  95

Thr Leu Arg Leu Ile Val Ala Lys Lys Pro Gln Val Ile Phe Leu Glu
                100                 105                 110

Asn Val Lys Asn Leu Val Gly His Asp Asn Gly Asn Thr Phe Lys Val
            115                 120                 125

Ile Tyr Glu Ala Leu Glu Ser Asn Gly Tyr His Ile Lys Tyr Gln Val
130                 135                 140

Leu Asn Ala Lys Asp Phe Gly Asn Ile Pro Gln Asn Arg Glu Arg Ile
145                 150                 155                 160

Tyr Ile Val Gly Phe Arg Asn Ile Glu His Tyr Lys Asn Phe Asn Phe
                165                 170                 175

Pro Met Pro Gln Pro Leu Thr Leu Thr Ile Lys Asp Met Ile Asn Leu
            180                 185                 190

Ser Asp Lys Leu Asp Asp Arg Phe Tyr Tyr Thr Glu Asp Lys Cys Ser
        195                 200                 205

Phe Tyr Ser Pro Leu Gln Glu Gln Met Thr Ser Asp Glu Thr Ile Tyr
210                 215                 220

Gln Trp Arg Arg Lys Tyr Val Arg Glu Asn Lys Ser Asn Val Cys Pro
225                 230                 235                 240

Thr Leu Thr Ala Asn Met Gly Thr Gly Gly His Asn Val Pro Leu Val
                245                 250                 255

Lys Thr Lys His Gly Ile Arg Lys Leu Thr Pro Arg Glu Cys Phe Asn
            260                 265                 270

Phe Gln Gly Tyr Pro Glu Asp Phe Ile Leu Pro Glu Leu Ala Pro Thr
        275                 280                 285

His Leu Tyr Lys Gln Ala Gly Asn Ser Val Val Val Pro Val Ile Arg
290                 295                 300

Arg Ile Ala Glu Asn Ile Tyr Lys Ser Met Leu
305                 310                 315

<210> SEQ ID NO 37
<211> LENGTH: 541
<212> TYPE: PRT

<213> ORGANISM: Clostridium difficile

<400> SEQUENCE: 37

Met Tyr Asn Val Ile Asp Leu Phe Ala Gly Ala Gly Gly Leu Ser Leu
1               5                   10                  15

Gly Phe Glu Met Thr Lys Lys Phe Asn Met Val Ala Phe Val Glu Lys
                20                  25                  30

Asn Asp Asn Ala Ala Lys Thr Tyr Leu Glu Asn His Pro Ser Val Lys
            35                  40                  45

Arg Tyr Cys Asp Ile Lys Arg Leu Asp Phe Gln Asp Ile Leu Asn Ser
    50                  55                  60

Val Asp Lys Ile Asp Val Val Ile Gly Gly Pro Pro Cys Gln Gly Phe
65                  70                  75                  80

Ser Asn Ala Asn Arg Gln Lys Arg Lys Ile Ile Asn Gly Asn Asn Glu
                85                  90                  95

Leu Val Lys Leu Tyr Val Asp Ala Ile Asp Lys Leu Lys Pro Asn Val
            100                 105                 110

Phe Val Met Glu Asn Val Lys Thr Ile Ser Ser Asn Lys His Ser Phe
        115                 120                 125

Tyr Leu Thr Lys Lys Asp Lys Asn His Ile Ile Asn Asn Leu Lys Leu
130                 135                 140

Asn Ile Tyr Asn Lys Asp Ser Val Leu Tyr Asp Arg Thr Glu Tyr Ile
145                 150                 155                 160

Asn Glu Leu Phe Asn Ile Ile Ser Ile Glu Asp Ile Glu Ser Tyr Ile
                165                 170                 175

Ile Ser Asn Ile Asp Leu Lys Asn Leu Lys Ile Ile Lys Lys Lys
            180                 185                 190

Lys Asp Ile Cys Asp Tyr Leu Asn Lys Ile Ser Asn Tyr Lys Lys Val
        195                 200                 205

Lys Ser Thr Ile Glu Lys Leu Glu Thr Arg Gly Lys Met Pro Lys Trp
    210                 215                 220

Tyr Leu Glu Leu Ile Asn Lys Val Lys Asn Ile Leu Glu Asn Met Leu
225                 230                 235                 240

Tyr Asn Arg Asn Leu Ser Asp Glu Gln Ile Phe Tyr Leu Asn Leu Phe
                245                 250                 255

Leu Asp Ile Gln Asn Leu Phe Leu Gly Ile Tyr Glu Leu Lys Ser Glu
            260                 265                 270

Ser Val Ile Phe Glu Asn Thr Leu Asp Asp Asn Lys Ile Ile Ala Lys
        275                 280                 285

Met Asp Thr Tyr Ile Ile Ile Asp Tyr Ile Asn Ala Ser Phe Glu Tyr
    290                 295                 300

Leu Gly Tyr Val Leu Asn Gly Ser Ala Leu Asn Ser Ile Asp Tyr Gly
305                 310                 315                 320

Val Pro Gln Asn Arg Glu Arg Phe Val Leu Ile Gly Ala Lys Lys Asp
                325                 330                 335

Phe Leu Lys Asn Lys Lys Ile Glu Thr Pro Lys Pro Ile Val Gly Glu
            340                 345                 350

Asn Tyr Val Thr Val Arg Asp Ala Ile Gly Asp Leu Ala Glu Tyr Glu
        355                 360                 365

Ala Ser Lys Gly Ser Met Asp Tyr Cys Phe Glu Lys Asn Ser Asn Asn
    370                 375                 380

Ile Glu Lys Asp Phe Tyr Arg Lys Ile Ile Leu Asp Ser Asn Lys Ile
385                 390                 395                 400

```
Tyr Asn His Val Cys Thr Asp Thr Arg Asn Ile Ala Leu Lys Arg Phe
                405                 410                 415

Glu Tyr Ile Asn Gln Gly Asn Asn Phe His Ser Leu Pro Asp Glu Leu
            420                 425                 430

Lys Gly Thr Tyr Ala Asp Pro Glu Arg Thr Gln Asn Thr Ile Tyr Lys
        435                 440                 445

Arg Leu Val Tyr Asp Lys Pro Ser Asp Thr Val Val Asn Val Arg Lys
    450                 455                 460

Ser Met Trp Ile His Pro Ile Lys Asn Arg Ala Val Ser Ala Arg Glu
465                 470                 475                 480

Ala Ala Arg Leu Gln Ser Phe Pro Asp Ser Tyr Lys Phe Leu Gly Thr
                485                 490                 495

Lys Asp Ser Val Tyr Gln Gln Ile Gly Asn Ala Val Pro Pro Leu Leu
            500                 505                 510

Gly Arg Val Val Ala Glu Lys Ile Leu Asn Leu Phe Asn Asp Glu Pro
        515                 520                 525

Asn Glu Tyr Leu Arg Asp Val Phe Glu Ala Leu Asp Gly
    530                 535                 540

<210> SEQ ID NO 38
<211> LENGTH: 541
<212> TYPE: PRT
<213> ORGANISM: Clostridium difficile 630

<400> SEQUENCE: 38

Met Tyr Asn Val Ile Asp Leu Phe Ala Gly Ala Gly Gly Leu Ser Leu
1               5                   10                  15

Gly Phe Glu Met Thr Lys Lys Phe Asn Met Val Ala Phe Val Glu Lys
            20                  25                  30

Asn Asp Asn Ala Ala Lys Thr Tyr Leu Glu Asn His Pro Ser Val Lys
        35                  40                  45

Arg Tyr Cys Asp Ile Lys Arg Leu Asp Phe Gln Asp Ile Leu Asn Ser
    50                  55                  60

Val Asp Lys Ile Asp Val Val Ile Gly Gly Pro Pro Cys Gln Gly Phe
65                  70                  75                  80

Ser Asn Ala Asn Arg Gln Lys Arg Lys Ile Ile Asn Gly Asn Asn Glu
                85                  90                  95

Leu Val Lys Leu Tyr Val Asp Ala Ile Asp Lys Leu Lys Pro Asn Val
            100                 105                 110

Phe Val Met Glu Asn Val Lys Thr Ile Ser Ser Asn Lys His Ser Phe
        115                 120                 125

Tyr Leu Thr Lys Lys Asp Lys Asn His Ile Ile Asn Asn Leu Lys Leu
    130                 135                 140

Asn Ile Tyr Asn Lys Asp Ser Val Leu Tyr Asp Arg Thr Glu Tyr Ile
145                 150                 155                 160

Asn Glu Leu Phe Asn Ile Ile Ser Ile Glu Asp Ile Glu Ser Tyr Ile
                165                 170                 175

Ile Ser Asn Ile Asp Leu Lys Asn Leu Lys Ile Ile Lys Lys Lys
            180                 185                 190

Lys Asp Ile Cys Asp Tyr Leu Asn Lys Ile Ser Asn Tyr Lys Lys Val
        195                 200                 205

Lys Ser Thr Ile Glu Lys Leu Glu Thr Arg Gly Lys Met Pro Lys Trp
    210                 215                 220

Tyr Leu Glu Leu Ile Asn Lys Val Lys Asn Ile Leu Glu Asn Met Leu
225                 230                 235                 240
```

```
Tyr Asn Arg Asn Leu Ser Asp Glu Gln Ile Phe Tyr Leu Asn Leu Phe
                245                 250                 255

Leu Asp Ile Gln Asn Leu Phe Leu Gly Ile Tyr Glu Leu Lys Ser Glu
            260                 265                 270

Ser Val Ile Phe Glu Asn Thr Leu Asp Asp Asn Lys Ile Ile Ala Lys
        275                 280                 285

Met Asp Thr Tyr Ile Ile Ile Asp Tyr Ile Asn Ala Ser Phe Glu Tyr
    290                 295                 300

Leu Gly Tyr Val Leu Asn Gly Ser Ala Leu Asn Ser Ile Asp Tyr Gly
305                 310                 315                 320

Val Pro Gln Asn Arg Glu Arg Phe Val Leu Ile Gly Ala Lys Lys Asp
                325                 330                 335

Phe Leu Lys Asn Lys Lys Ile Glu Thr Pro Lys Pro Ile Val Gly Glu
            340                 345                 350

Asn Tyr Val Thr Val Arg Asp Ala Ile Gly Asp Leu Ala Glu Tyr Glu
        355                 360                 365

Ala Ser Lys Gly Ser Met Asp Tyr Cys Phe Glu Lys Asn Ser Asn Asn
    370                 375                 380

Ile Glu Lys Asp Phe Tyr Arg Lys Ile Ile Leu Asp Ser Asn Lys Ile
385                 390                 395                 400

Tyr Asn His Val Cys Thr Asp Thr Arg Asn Ile Ala Leu Lys Arg Phe
                405                 410                 415

Glu Tyr Ile Asn Gln Gly Asn Asn Phe His Ser Leu Pro Asp Glu Leu
            420                 425                 430

Lys Gly Thr Tyr Ala Asp Pro Glu Arg Thr Gln Asn Thr Ile Tyr Lys
        435                 440                 445

Arg Leu Val Tyr Asp Lys Pro Ser Asp Thr Val Val Asn Val Arg Lys
    450                 455                 460

Ser Met Trp Ile His Pro Ile Lys Asn Arg Ala Val Ser Ala Arg Glu
465                 470                 475                 480

Ala Ala Arg Leu Gln Ser Phe Pro Asp Ser Tyr Lys Phe Leu Gly Thr
                485                 490                 495

Lys Asp Ser Val Tyr Gln Gln Ile Gly Asn Ala Val Pro Pro Leu Leu
            500                 505                 510

Gly Arg Val Val Ala Glu Lys Ile Leu Asn Leu Phe Asn Asp Glu Pro
        515                 520                 525

Asn Glu Tyr Leu Arg Asp Val Phe Glu Ala Leu Asp Gly
    530                 535                 540

<210> SEQ ID NO 39
<211> LENGTH: 319
<212> TYPE: PRT
<213> ORGANISM: Caldicellulosiruptor kristjanssonii 177R1B

<400> SEQUENCE: 39

Met Ile Lys Ile Arg Val Val Ser Leu Phe Ser Gly Val Gly Gly Ile
1               5                   10                  15

Cys Leu Ala Phe Lys Gln Ala Gly Phe Asp Val Ile Trp Ala Asn Asp
            20                  25                  30

Ile Asp Lys Tyr Ala Cys Ile Thr Tyr Arg Ser Asn Pro Thr Val
        35                  40                  45

Glu Leu Val Glu Gly Asp Ile Gln Ser Ile Asp Ser Asn Asn Ile Pro
    50                  55                  60

Glu Cys Asp Ile Ile Thr Ala Gly Phe Pro Cys Gln Pro Phe Ser Ile
```

```
                65                  70                  75                  80
Ala Gly Tyr Gln Arg Gly Leu Asn Asp Pro Arg Gly Arg Leu Phe Tyr
                        85                  90                  95

Glu Ile Val Arg Ile Val His Asp Lys Lys Pro Lys Ile Ile Phe Leu
                    100                 105                 110

Glu Asn Val Lys Asn Leu Val Ser His Asn Asn Gly Ile Thr Phe Lys
                    115                 120                 125

Asn Ile Leu Asn Ala Leu Glu Asn Gly Tyr Tyr Leu Lys Tyr Ala
            130                 135                 140

Val Leu Asn Ser Leu Glu Tyr Gly Asn Val Pro Gln Asn Arg Glu Arg
145                 150                 155                 160

Val Tyr Ile Val Gly Phe Leu Asp Lys Ser Met Tyr Glu Ala Phe Lys
                    165                 170                 175

Phe Pro Glu Pro Val Ser Leu Thr Val Thr Ile His Asp Ile Ile Lys
                    180                 185                 190

Pro Trp Glu Lys Lys Asp Glu Lys Tyr Tyr Arg Glu Gly Lys Tyr
            195                 200                 205

Tyr Glu Leu Leu Lys Gln Asn Val Asp Asp Pro Asn Thr Val Tyr Gln
            210                 215                 220

Ile Arg Arg Ile Tyr Val Arg Lys Asn Lys Lys Gly Val Cys Pro Thr
225                 230                 235                 240

Leu Thr Ala Asn Met Gly Glu Gly Gly His Asn Val Pro Ile Val Met
                    245                 250                 255

Asp Asn Tyr Gly Phe Arg Lys Leu Thr Pro Arg Glu Cys Phe Ile Leu
                    260                 265                 270

Gln Gly Phe Pro Glu Asp Phe Val Leu Pro Ser Gly Leu Ala Asp Ser
                    275                 280                 285

Lys Leu Tyr Lys Gln Ala Gly Asn Ala Val Thr Val Thr Val Val Lys
            290                 295                 300

Arg Ile Ala Asp Lys Ile Leu Glu Thr Cys Leu Val Lys Ser Ile
305                 310                 315

<210> SEQ ID NO 40
<211> LENGTH: 406
<212> TYPE: PRT
<213> ORGANISM: Clostridium mangenotii LM2

<400> SEQUENCE: 40

Met Thr Lys Asn Asn Asp Ala Val Ser Thr Lys Asn Tyr Thr Val Ala
1               5                   10                  15

Ser Phe Phe Gly Gly Val Gly Gly Ile Asp Leu Gly Phe Glu Gln Ala
                    20                  25                  30

Lys Lys Phe Ser Thr Val Tyr Ile Asn Glu Phe Asp Lys Asn Ala Gln
            35                  40                  45

Glu Thr Ile Ser Ile Asn Phe Pro Arg Val Ser Leu Asp Arg Arg Asp
50                  55                  60

Ile His Glu Val Arg Val Asp Glu Val Pro Ser Thr Asp Ile Val Ala
65                  70                  75                  80

Gly Gly Phe Pro Cys Gln Ala Phe Ser Ile Ala Gly Tyr Arg Lys Gly
                    85                  90                  95

Phe Glu Asp Glu Arg Gly Asp Leu Phe Phe Glu Leu Leu Arg Ile Ile
                    100                 105                 110

Lys His His Lys Pro Lys Val Ile Phe Ile Glu Asn Val Lys Asn Met
            115                 120                 125
```

```
Val Thr His Asp His Gly Asn Thr Phe Lys Val Ile Arg Glu Ala Leu
    130                 135                 140

Thr Leu Asn Gly Tyr Tyr Ile Lys Trp Lys Val Ile Asn Gly Lys Asp
145                 150                 155                 160

Tyr Gly Asp Ile Pro Gln Asn Arg Glu Arg Ile Tyr Ile Thr Gly Phe
                165                 170                 175

Leu Asp Lys Asn Ala Phe Asp Glu Phe Glu Phe Pro Asn Lys Ile Glu
            180                 185                 190

Leu Thr Asn Gly Leu Asp Thr Val Ile Asp Phe Lys Ala Lys Val Glu
        195                 200                 205

Asp Lys Tyr Tyr Arg Gln Gly Ile Gln Pro Phe Tyr Asp Lys Leu
    210                 215                 220

Glu Glu Thr Ile Thr Ser Gln Asn Ser Val Tyr Gln Trp Arg Arg Gln
225                 230                 235                 240

Tyr Val Arg Glu Asn Lys Ser Gly Val Val Pro Thr Leu Thr Ala Asn
                245                 250                 255

Met Gly Thr Gly Gly His Asn Val Pro Leu Ile Leu Ser Tyr Tyr Gly
            260                 265                 270

Ile Arg Lys Leu Thr Pro Arg Glu Thr Phe Asn Ile Gln Gly Phe Pro
        275                 280                 285

Thr Asp Phe Lys Leu Pro Glu Ile Ser Asn Ala Gln Leu Tyr Lys Gln
    290                 295                 300

Ala Gly Asn Ser Val Val Pro Val Ile Lys Arg Ile Ala Glu Asn
305                 310                 315                 320

Ile Ala Asn Ala Leu Glu Glu Ala Glu Asn Lys Asn Glu Ile Tyr Asn
                325                 330                 335

Thr Val Glu Glu Asn Asn Lys Asn Ile Leu Ile Tyr Val Asp Met Lys
            340                 345                 350

Ser Arg Phe Glu Gly Glu Ser Phe Val Gln Ala Tyr Phe Asp Glu Val
        355                 360                 365

Cys Glu Ala Asn Asp Phe Ala Ile Ile Thr Glu Ile Pro Ile Leu Ser
    370                 375                 380

Asp Glu Glu Tyr Leu Lys Leu Val Lys Arg Asn Val Ser Lys Arg Phe
385                 390                 395                 400

Tyr Ser Leu Gln Thr Lys
                405

<210> SEQ ID NO 41
<211> LENGTH: 318
<212> TYPE: PRT
<213> ORGANISM: Capnocytophaga ochracea DSM 7271

<400> SEQUENCE: 41

Met Gly Lys Ser Val Lys Phe Ile Asp Leu Phe Ala Gly Val Gly Gly
1               5                   10                  15

Phe Arg Tyr Ala Leu Gln Asn Ile Gly Ala Glu Cys Val Phe Ser Ser
            20                  25                  30

Glu Trp Asp Lys Phe Ala Gln Gln Thr Tyr Lys Leu Asn Tyr Gly Glu
        35                  40                  45

Val Pro Phe Gly Asp Ile Thr Leu Gln Glu Thr Lys Asp Asn Ile Pro
    50                  55                  60

Asn Glu Phe Asp Ile Leu Cys Ala Gly Phe Pro Cys Gln Ala Phe Ser
65                  70                  75                  80

Ile Ala Gly Tyr Gln Lys Gly Phe Glu Asp Ile Arg Gly Thr Leu Phe
                85                  90                  95
```

```
Phe Glu Ile Glu Glu Ile Val Arg Lys His Arg Pro Lys Val Ile Phe
                100                 105                 110

Leu Glu Asn Val Lys Asn Leu Val Ser His Asp Lys Gly Lys Thr Phe
            115                 120                 125

Lys Val Ile Thr Asn Ile Leu Glu Glu Lys Leu Gly Tyr Lys Ile Phe
        130                 135                 140

Tyr Lys Val Leu Asn Thr Met Glu Tyr Ala Asn Ile Pro Gln Asn Arg
145                 150                 155                 160

Glu Arg Ile Phe Ile Val Ala Phe Asp Pro Lys Gln Val Pro Asn Tyr
                165                 170                 175

Lys Glu Phe Gln Phe Pro Glu Lys Ile Lys Leu Thr Lys Thr Ile His
            180                 185                 190

Ser Phe Leu Glu Lys Gly Lys Gln Asn Asp Tyr Phe Tyr Gln Leu
        195                 200                 205

Ser His Lys Tyr Ser Pro Glu Leu Ile Lys Ile Val Thr Arg Lys Asp
    210                 215                 220

Thr Ile Tyr Gln Trp Arg Arg Val Tyr Val Arg Glu Asn Lys Asn Asn
225                 230                 235                 240

Val Cys Pro Thr Leu Thr Ala Asn Met Gly Thr Gly Gly His Asn Val
                245                 250                 255

Pro Ile Ile Lys Asp Asn Phe Gly Ile Arg Lys Leu Thr Pro Arg Glu
            260                 265                 270

Cys Phe Asn Phe Gln Gly Tyr Pro Lys Gly Phe Ile Leu Ser Lys Glu
        275                 280                 285

Ile Ala Ile Ser Lys Leu Tyr Met Gln Ala Gly Asn Ser Val Thr Met
290                 295                 300

Pro Leu Ile Gln Arg Val Ser Glu Gln Ile Leu Lys Val Leu
305                 310                 315

<210> SEQ ID NO 42
<211> LENGTH: 408
<212> TYPE: PRT
<213> ORGANISM: Flavobacterium sp. 4H

<400> SEQUENCE: 42

Met Ser Leu Lys Gln Thr Ile Ser Ile Asn Glu Phe Asp Gly Lys Ser
1               5                   10                  15

Tyr Gln Ile Arg Leu Val Glu Gly Ile Glu Asp Lys Ala Val Leu Thr
                20                  25                  30

His Tyr Leu His Asn Tyr Arg Asn Gly Val Lys Lys His Tyr Glu Lys
            35                  40                  45

Asp Ala Ile Ser Thr Leu Lys Asn Phe Val Glu Tyr Lys Gln Glu Glu
        50                  55                  60

Thr Glu Leu Pro Ile Val Ala Glu Asp Ala Leu Gln Gln Leu Leu Phe
65                  70                  75                  80

Glu Val Glu Asn Val Pro Phe Pro Thr Pro Gly Asn Tyr Ser Phe Lys
                85                  90                  95

Phe Ile Asp Leu Phe Ala Gly Ile Gly Gly Phe Arg Leu Ala Leu Gln
            100                 105                 110

Asn Val Gly Gly Lys Cys Val Phe Thr Ser Glu Trp Asn Asn Glu Ala
        115                 120                 125

Gln Lys Thr Tyr Arg Glu Asn Phe Gly Glu Val Pro Phe Gly Asp Ile
    130                 135                 140

Thr Lys Glu Arg Asn Lys Asn Tyr Ile Pro Glu Lys Phe Asp Ile Leu
```

```
                145                 150                 155                 160

Cys Ala Gly Phe Pro Cys Gln Ala Phe Ser Ile Ala Gly Tyr Gln Lys
                        165                 170                 175

Gly Phe Ala Asp Thr Arg Gly Thr Leu Phe Asp Ile Glu Gln Ile
                180                 185                 190

Val Glu Lys His Lys Pro Lys Val Phe Leu Glu Asn Val Lys Asn
                    195                 200                 205

Leu Val Ser His Asp Asn Gly Asn Thr Phe Lys Thr Ile Ile Glu Thr
        210                 215                 220

Leu Glu Leu Lys Leu Gly Tyr Lys Thr Phe Ala Lys Val Leu Asn Ser
        225                 230                 235                 240

Ala Thr His Ala Asn Val Pro Gln Asn Arg Glu Arg Ile Phe Ile Val
                        245                 250                 255

Ala Phe Asp Pro Lys Gln Val Lys Asn Tyr Ser Lys Phe Glu Phe Pro
                    260                 265                 270

Lys Pro Ile Lys Leu Thr Lys Thr Ile His Asp Phe Leu Asp Lys Glu
                275                 280                 285

Lys Gln Asp Asp Ile Phe Tyr Tyr Lys Lys Asp His Gln Tyr Tyr Pro
            290                 295                 300

Glu Leu Val Lys Thr Met Ile Ser Lys Asp Thr Val Tyr Gln Trp Arg
        305                 310                 315                 320

Arg Val Tyr Ala Arg Glu Asn Lys Ser Asn Leu Cys Pro Thr Leu Thr
                        325                 330                 335

Ala Asn Met Gly Ser Gly Gly His Asn Val Pro Leu Ile Ile Asp Asp
                    340                 345                 350

Phe Gly Ile Arg Lys Leu Thr Pro Lys Glu Cys Phe Ala Phe Gln Gly
                355                 360                 365

Tyr Pro Ile Glu Lys Tyr Ile Ile Pro Lys Leu Ala Asn Ser Lys Leu
            370                 375                 380

Tyr Met Gln Ala Gly Asn Ser Val Thr Thr Asn Leu Ile Glu Arg Ile
        385                 390                 395                 400

Ala Asn Gln Ile Ile Glu Val Leu
                        405

<210> SEQ ID NO 43
<211> LENGTH: 317
<212> TYPE: PRT
<213> ORGANISM: Lactococcus lactis W39

<400> SEQUENCE: 43

Met Leu Lys Ile Ala Ser Phe Phe Ala Gly Val Gly Gly Ile Asp Leu
        1               5                   10                  15

Gly Phe Glu Asn Ala Gly Phe Lys Thr Ile Tyr Ala Asn Glu Phe Asp
                        20                  25                  30

Asn Tyr Ala Ala Asp Thr Phe Glu Met Asn Phe Asp Val Lys Val Asp
                    35                  40                  45

Arg Arg Asp Ile Asn Asp Val Gln Ala Asp Glu Ile Pro Asp Phe Asp
                50                  55                  60

Ile Met Leu Ala Gly Phe Pro Cys Gln Ala Phe Ser Ile Ala Gly Tyr
        65                  70                  75                  80

Arg Gln Gly Phe Asn Asp Glu Gln Gly Arg Gly Asn Leu Phe Phe Glu
                        85                  90                  95

Leu Val Arg Ile Leu Glu Thr Lys Lys Pro Arg Val Ala Phe Phe Glu
                    100                 105                 110
```

```
Asn Val Lys Asn Leu Val Ser His Asp Ser Gly Asn Thr Phe Arg Val
            115                 120                 125

Ile Cys Ser Glu Leu Glu Arg Leu Gly Tyr Lys Tyr Leu Phe Gln Val
        130                 135                 140

Phe Asn Ala Ser Glu Tyr Gly Asn Ile Pro Gln Asn Arg Glu Arg Ile
145                 150                 155                 160

Tyr Ile Val Ala Phe Lys Asn Lys Asp Tyr Ala Asn Phe Glu Leu
                165                 170                 175

Pro Lys Ser Ile Pro Leu Lys Thr Thr Ile His Asp Val Ile Asp Phe
            180                 185                 190

Ser Lys Lys Gln Asp Asp Lys Phe Tyr Tyr Thr Ser Glu Lys Asn Lys
        195                 200                 205

Phe Phe Asp Glu Leu Lys Glu Asn Met Thr Asn His Asp Thr Thr Tyr
210                 215                 220

Gln Trp Arg Arg Val Tyr Val Arg Glu Asn Lys Ser Asn Leu Val Pro
225                 230                 235                 240

Thr Leu Thr Ala Asn Met Gly Thr Gly Gly His Asn Val Pro Ile Ile
                245                 250                 255

Leu Thr Tyr Ser Gly Asp Ile Arg Lys Leu Thr Pro Arg Glu Cys Phe
            260                 265                 270

Asn Val Gln Gly Phe Pro Lys Glu Tyr Lys Leu Pro Asn Gln Ser Asn
        275                 280                 285

Gly Arg Leu Tyr Lys Gln Ala Gly Asn Ser Val Val Pro Val Ile
                295                 300
            290

Glu Arg Ile Ala Lys Asn Leu Ala Asp Thr Ile Val Glu
305                 310                 315

<210> SEQ ID NO 44
<211> LENGTH: 841
<212> TYPE: PRT
<213> ORGANISM: Bacillus licheniformis DSM 13

<400> SEQUENCE: 44

Met Leu Gly Ile Leu Asn Lys Val Phe Asp Pro Thr Lys Arg Thr Leu
1               5                   10                  15

Ser Arg Tyr Glu Lys Lys Ala Asn Glu Ile Asp Ala Leu Lys Ala Asp
            20                  25                  30

Ile Glu Lys Leu Ser Asp Glu Ala Leu Lys Gln Lys Thr Ile Glu Phe
        35                  40                  45

Lys Glu Arg Leu Glu Lys Gly Glu Thr Val Asp Asp Leu Leu Val Glu
50                  55                  60

Ala Phe Ala Val Val Arg Glu Ala Ser Arg Arg Val Thr Gly Met Phe
65                  70                  75                  80

Pro Phe Lys Val Gln Leu Met Gly Gly Val Ala Leu His Glu Gly Asn
                85                  90                  95

Ile Ala Glu Met Lys Thr Gly Glu Gly Lys Thr Leu Thr Ser Thr Met
            100                 105                 110

Pro Val Tyr Leu Asn Ala Leu Ser Gly Lys Gly Val His Val Val Thr
        115                 120                 125

Val Asn Glu Tyr Leu Ala Ser Arg Asp Ala Glu Met Gly Lys Ile
130                 135                 140

Phe Glu Phe Leu Gly Leu Thr Val Gly Leu Asn Leu Asn Ser Leu Ser
145                 150                 155                 160

Lys Asp Glu Lys Arg Glu Ala Tyr Ala Ala Asp Ile Thr Tyr Ser Thr
                165                 170                 175
```

-continued

```
Asn Asn Glu Leu Gly Phe Asp Tyr Leu Arg Asp Asn Met Val Leu Tyr
            180                 185                 190

Lys Glu Gln Met Val Gln Arg Pro Leu His Phe Ala Val Ile Asp Glu
            195                 200                 205

Val Asp Ser Ile Leu Ile Asp Glu Ala Arg Thr Pro Leu Ile Ile Ser
210                 215                 220

Gly Gln Ala Ala Lys Ser Thr Lys Leu Tyr Val Gln Ala Asn Ala Phe
225                 230                 235                 240

Val Arg Thr Leu Lys Ala Asp Gln Asp Tyr Thr Tyr Asp Val Lys Thr
                245                 250                 255

Lys Gly Val Gln Leu Thr Glu Glu Gly Met Thr Lys Ala Glu Lys Ala
            260                 265                 270

Phe Gly Ile Glu Asn Leu Phe Asp Val Arg His Val Ala Leu Asn His
            275                 280                 285

His Ile Ala Gln Ala Leu Lys Ala His Ala Ala Met His Lys Asp Val
        290                 295                 300

Asp Tyr Val Val Glu Asp Gly Gln Val Val Ile Val Asp Ser Phe Thr
305                 310                 315                 320

Gly Arg Leu Met Lys Gly Arg Arg Tyr Ser Asp Gly Leu His Gln Ala
                325                 330                 335

Ile Glu Ala Lys Glu Gly Leu Glu Ile Gln Asn Glu Ser Met Thr Leu
            340                 345                 350

Ala Thr Ile Thr Phe Gln Asn Tyr Phe Arg Met Tyr Glu Lys Leu Ala
        355                 360                 365

Gly Met Thr Gly Thr Ala Lys Thr Glu Glu Glu Phe Arg Asn Ile
            370                 375                 380

Tyr Asn Met Gln Val Val Thr Ile Pro Thr Asn Lys Pro Ile Ala Arg
385                 390                 395                 400

Asp Asp Arg Pro Asp Leu Ile Tyr Arg Thr Met Glu Gly Lys Phe Lys
                405                 410                 415

Ala Val Ala Glu Asp Val Ala Gln Arg Tyr Met Val Gly Gln Pro Val
            420                 425                 430

Leu Val Gly Thr Val Ala Val Glu Thr Ser Glu Leu Ile Ser Arg Leu
        435                 440                 445

Leu Lys Asn Lys Gly Ile Pro His Gln Val Leu Asn Ala Lys Asn His
450                 455                 460

Glu Arg Glu Ala Gln Ile Ile Glu Asp Ala Gly Gln Lys Gly Ala Val
465                 470                 475                 480

Thr Ile Ala Thr Asn Met Ala Gly Arg Gly Thr Asp Ile Lys Leu Gly
                485                 490                 495

Glu Gly Val Lys Glu Leu Gly Gly Leu Ala Val Ile Gly Thr Glu Arg
            500                 505                 510

His Glu Ser Arg Arg Ile Asp Asn Gln Leu Arg Gly Arg Ser Gly Arg
        515                 520                 525

Gln Gly Asp Pro Gly Ile Thr Gln Phe Tyr Leu Ser Met Glu Asp Glu
            530                 535                 540

Leu Met Lys Arg Phe Gly Ala Glu Arg Thr Met Ala Met Leu Asp Arg
545                 550                 555                 560

Phe Gly Met Asp Asp Ser Thr Pro Ile Gln Ser Lys Met Val Ser Arg
                565                 570                 575

Ala Val Glu Ser Ser Gln Lys Arg Val Glu Gly Asn Asn Phe Asp Ala
            580                 585                 590
```

-continued

```
Arg Lys Gln Leu Leu Gln Tyr Asp Val Leu Arg Gln Arg Glu
            595                 600                 605

Val Ile Tyr Lys Gln Arg Phe Glu Val Ile Asp Ser Asp Asn Leu Arg
610                 615                 620

Ser Ile Val Glu Asn Met Ile Lys Ala Ser Leu Glu Arg Ala Val Ala
625                 630                 635                 640

Ser Tyr Thr Pro Lys Glu Asp Leu Pro Glu Glu Trp Asn Leu Asp Gly
                645                 650                 655

Leu Val Glu Leu Val Asn Ala Asn Phe Leu Asp Glu Gly Gly Val Glu
            660                 665                 670

Lys Ser Asp Ile Phe Gly Lys Glu Pro Glu Glu Ile Thr Glu Leu Ile
        675                 680                 685

Tyr Asp Arg Ile Lys Thr Lys Tyr Asp Glu Lys Glu Arg Tyr Gly
    690                 695                 700

Ser Glu Gln Met Arg Glu Phe Glu Lys Val Ile Val Leu Arg Glu Val
705                 710                 715                 720

Asp Thr Lys Trp Met Asp His Ile Asp Ala Met Asp Gln Leu Arg Gln
                725                 730                 735

Gly Ile His Leu Arg Ala Tyr Ala Gln Thr Asn Pro Leu Arg Glu Tyr
            740                 745                 750

Gln Met Glu Gly Phe Ala Met Phe Glu Asn Met Ile Ala Ala Ile Glu
        755                 760                 765

Asp Asp Val Ala Lys Phe Val Met Lys Ala Glu Ile Glu Asn Asn Leu
    770                 775                 780

Glu Arg Glu Glu Val Ile Gln Gly Gln Thr Thr Ala His Gln Pro Lys
785                 790                 795                 800

Glu Gly Asp Glu Glu Lys Gln Ala Lys Lys Pro Val Arg Lys Ala
                805                 810                 815

Val Asp Ile Gly Arg Asn Asp Pro Cys Tyr Cys Gly Ser Gly Lys Lys
            820                 825                 830

Tyr Lys Asn Cys Cys Gly Arg Thr Glu
        835                 840
```

<210> SEQ ID NO 45
<211> LENGTH: 901
<212> TYPE: PRT
<213> ORGANISM: Escherichia coli K12

<400> SEQUENCE: 45

```
Met Leu Ile Lys Leu Leu Thr Lys Val Phe Gly Ser Arg Asn Asp Arg
1               5                   10                  15

Thr Leu Arg Arg Met Arg Lys Val Val Asn Ile Ile Asn Ala Met Glu
            20                  25                  30

Pro Glu Met Glu Lys Leu Ser Asp Glu Glu Leu Lys Gly Lys Thr Ala
        35                  40                  45

Glu Phe Arg Ala Arg Leu Glu Lys Gly Glu Val Leu Glu Asn Leu Ile
    50                  55                  60

Pro Glu Ala Phe Ala Val Val Arg Glu Ala Ser Lys Arg Val Phe Gly
65                  70                  75                  80

Met Arg His Phe Asp Val Gln Leu Leu Gly Gly Met Val Leu Asn Glu
                85                  90                  95

Arg Cys Ile Ala Glu Met Arg Thr Gly Glu Gly Lys Thr Leu Thr Ala
            100                 105                 110

Thr Leu Pro Ala Tyr Leu Asn Ala Leu Thr Gly Lys Gly Val His Val
        115                 120                 125
```

```
Val Thr Val Asn Asp Tyr Leu Ala Gln Arg Asp Ala Glu Asn Asn Arg
    130                 135                 140

Pro Leu Phe Glu Phe Leu Gly Leu Thr Val Gly Ile Asn Leu Pro Gly
145                 150                 155                 160

Met Pro Ala Pro Ala Lys Arg Glu Ala Tyr Ala Ala Asp Ile Thr Tyr
                165                 170                 175

Gly Thr Asn Asn Glu Tyr Gly Phe Asp Tyr Leu Arg Asp Asn Met Ala
                180                 185                 190

Phe Ser Pro Glu Glu Arg Val Gln Arg Lys Leu His Tyr Ala Leu Val
            195                 200                 205

Asp Glu Val Asp Ser Ile Leu Ile Asp Glu Ala Arg Thr Pro Leu Ile
    210                 215                 220

Ile Ser Gly Pro Ala Glu Asp Ser Ser Glu Met Tyr Lys Arg Val Asn
225                 230                 235                 240

Lys Ile Ile Pro His Leu Ile Arg Gln Glu Lys Glu Asp Ser Glu Thr
                245                 250                 255

Phe Gln Gly Glu Gly His Phe Ser Val Asp Glu Lys Ser Arg Gln Val
                260                 265                 270

Asn Leu Thr Glu Arg Gly Leu Val Leu Ile Glu Glu Leu Leu Val Lys
            275                 280                 285

Glu Gly Ile Met Asp Glu Gly Glu Ser Leu Tyr Ser Pro Ala Asn Ile
    290                 295                 300

Met Leu Met His His Val Thr Ala Ala Leu Arg Ala His Ala Leu Phe
305                 310                 315                 320

Thr Arg Asp Val Asp Tyr Ile Val Lys Asp Gly Glu Val Ile Ile Val
                325                 330                 335

Asp Glu His Thr Gly Arg Thr Met Gln Gly Arg Arg Trp Ser Asp Gly
                340                 345                 350

Leu His Gln Ala Val Glu Ala Lys Glu Gly Val Gln Ile Gln Asn Glu
            355                 360                 365

Asn Gln Thr Leu Ala Ser Ile Thr Phe Gln Asn Tyr Phe Arg Leu Tyr
    370                 375                 380

Glu Lys Leu Ala Gly Met Thr Gly Thr Ala Asp Thr Glu Ala Phe Glu
385                 390                 395                 400

Phe Ser Ser Ile Tyr Lys Leu Asp Thr Val Val Pro Thr Asn Arg
                405                 410                 415

Pro Met Ile Arg Lys Asp Leu Pro Asp Leu Val Tyr Met Thr Glu Ala
                420                 425                 430

Glu Lys Ile Gln Ala Ile Ile Glu Asp Ile Lys Glu Arg Thr Ala Lys
            435                 440                 445

Gly Gln Pro Val Leu Val Gly Thr Ile Ser Ile Glu Lys Ser Glu Leu
    450                 455                 460

Val Ser Asn Glu Leu Thr Lys Ala Gly Ile Lys His Asn Val Leu Asn
465                 470                 475                 480

Ala Lys Phe His Ala Asn Glu Ala Ala Ile Val Ala Gln Ala Gly Tyr
                485                 490                 495

Pro Ala Ala Val Thr Ile Ala Thr Asn Met Ala Gly Arg Gly Thr Asp
                500                 505                 510

Ile Val Leu Gly Gly Ser Trp Gln Ala Glu Val Ala Ala Leu Glu Asn
            515                 520                 525

Pro Thr Ala Glu Gln Ile Glu Lys Ile Lys Ala Asp Trp Gln Val Arg
    530                 535                 540
```

-continued

His Asp Ala Val Leu Glu Ala Gly Gly Leu His Ile Ile Gly Thr Glu
545                 550                 555                 560

Arg His Glu Ser Arg Arg Ile Asp Asn Gln Leu Arg Gly Arg Ser Gly
            565                 570                 575

Arg Gln Gly Asp Ala Gly Ser Ser Arg Phe Tyr Leu Ser Met Glu Asp
        580                 585                 590

Ala Leu Met Arg Ile Phe Ala Ser Asp Arg Val Ser Gly Met Met Arg
    595                 600                 605

Lys Leu Gly Met Lys Pro Gly Glu Ala Ile Glu His Pro Trp Val Thr
610                 615                 620

Lys Ala Ile Ala Asn Ala Gln Arg Lys Val Glu Ser Arg Asn Phe Asp
625                 630                 635                 640

Ile Arg Lys Gln Leu Leu Glu Tyr Asp Val Ala Asn Asp Gln Arg
            645                 650                 655

Arg Ala Ile Tyr Ser Gln Arg Asn Glu Leu Leu Asp Val Ser Asp Val
        660                 665                 670

Ser Glu Thr Ile Asn Ser Ile Arg Glu Asp Val Phe Lys Ala Thr Ile
    675                 680                 685

Asp Ala Tyr Ile Pro Pro Gln Ser Leu Glu Glu Met Trp Asp Ile Pro
690                 695                 700

Gly Leu Gln Glu Arg Leu Lys Asn Asp Phe Asp Leu Asp Leu Pro Ile
705                 710                 715                 720

Ala Glu Trp Leu Asp Lys Glu Pro Glu Leu His Glu Glu Thr Leu Arg
            725                 730                 735

Glu Arg Ile Leu Ala Gln Ser Ile Glu Val Tyr Gln Arg Lys Glu Glu
        740                 745                 750

Val Val Gly Ala Glu Met Met Arg His Phe Glu Lys Gly Val Met Leu
    755                 760                 765

Gln Thr Leu Asp Ser Leu Trp Lys Glu His Leu Ala Ala Met Asp Tyr
770                 775                 780

Leu Arg Gln Gly Ile His Leu Arg Gly Tyr Ala Gln Lys Asp Pro Lys
785                 790                 795                 800

Gln Glu Tyr Lys Arg Glu Ser Phe Ser Met Phe Ala Ala Met Leu Glu
            805                 810                 815

Ser Leu Lys Tyr Glu Val Ile Ser Thr Leu Ser Lys Val Gln Val Arg
        820                 825                 830

Met Pro Glu Glu Val Glu Leu Glu Gln Gln Arg Met Glu Ala
    835                 840                 845

Glu Arg Leu Ala Gln Met Gln Gln Leu Ser His Gln Asp Asp Ser
850                 855                 860

Ala Ala Ala Ala Leu Ala Ala Gln Thr Gly Glu Arg Lys Val Gly
865                 870                 875                 880

Arg Asn Asp Pro Cys Pro Cys Gly Ser Gly Lys Lys Tyr Lys Gln Cys
            885                 890                 895

His Gly Arg Leu Gln
            900

<210> SEQ ID NO 46
<211> LENGTH: 799
<212> TYPE: PRT
<213> ORGANISM: Lactobacillus acidophilus NCFM

<400> SEQUENCE: 46

Met Ala Asn Ile Leu Lys Lys Leu Tyr Asn Thr Asp Lys Arg Glu Leu
1               5                   10                  15

```
Lys Lys Phe Glu Lys Tyr Ala Thr Lys Val Glu His Ala Asp Glu
             20                  25              30

Met Ser Lys Leu Ser Asp Glu Gln Leu Gln Ala Lys Thr Pro Glu Phe
         35                  40                  45

Arg Glu Arg Ile Lys Asn Gly Glu Ser Leu Asp Leu Leu Pro Glu
     50                  55                  60

Ala Phe Ala Val Ala Arg Glu Gly Ala Lys Arg Val Leu Gly Leu Tyr
 65              70                  75                      80

Pro Phe His Val Gln Ile Leu Gly Gly Ile Ala Leu His Phe Gly Asn
                 85                  90                  95

Ile Ala Glu Met Met Thr Gly Glu Gly Lys Thr Leu Thr Ala Thr Met
                100                 105                 110

Pro Val Tyr Leu Asn Ala Leu Glu Gly Lys Gly Val His Val Val Thr
             115                 120                 125

Val Asn Glu Tyr Leu Ser Ser Arg Asp Glu Glu Met Gly Gln Leu
 130                 135                 140

Tyr Arg Trp Leu Gly Leu Thr Val Gly Leu Asn Ile Asn Ser Met Ser
145                 150                 155                 160

Pro Asp Glu Lys Arg Glu Ala Tyr Asn Cys Asp Val Tyr Ser Thr
                 165                 170             175

Asn Ser Glu Leu Gly Phe Asp Tyr Leu Arg Asp Asn Met Val Val Tyr
             180                 185                 190

Lys Glu Gln Met Val Gln Arg Pro Leu Asn Tyr Ala Ile Ile Asp Glu
             195                 200                 205

Val Asp Ser Ile Leu Ile Asp Glu Ala Arg Thr Pro Leu Ile Ile Ser
 210                 215                 220

Gly Glu Ala Glu Gln Ala Asn Ser Asp Tyr Ile Arg Ala Asp Arg Phe
225                 230                 235                 240

Val Lys Thr Leu Thr Glu Asp Lys Ser Asp Asp Ala Asp Asp Asp
                 245                 250                 255

Glu Asp His Gly Asp Tyr Lys Ile Asp Trp Pro Thr Lys Thr Ile Ser
                 260                 265                 270

Leu Thr Arg Thr Gly Ile Glu Lys Ala Cys Glu His Phe Gly Leu Lys
     275                 280                 285

Asn Leu Tyr Asp Val Glu Asn Gln Lys Leu Val His His Ile Asp Gln
 290                 295                 300

Ala Leu Arg Ala Asn Tyr Ile Met Leu Lys Asp Ile Asp Tyr Val Val
305                 310                 315                 320

Gln Asp Gly Glu Val Leu Ile Val Asp Ser Phe Thr Gly Arg Val Met
                 325                 330                 335

Glu Gly Arg Arg Tyr Ser Asp Gly Leu His Gln Ala Ile Glu Ala Lys
             340                 345                 350

Glu Gly Val Lys Ile Gln Glu Glu Ser Arg Thr Gln Ala Thr Ile Thr
             355                 360                 365

Tyr Gln Asn Phe Phe Arg Met Tyr Lys Lys Leu Ser Gly Met Thr Gly
     370                 375                 380

Thr Gly Lys Thr Glu Glu Glu Glu Phe Arg Glu Ile Tyr Asn Met Gln
385                 390                 395                 400

Val Ile Thr Ile Pro Thr Asn Arg Pro Ile Ala Arg Lys Asp Met Pro
                 405                 410                 415

Asp Ile Leu Tyr Pro Thr Leu Asp Ser Lys Phe His Ala Val Ile Glu
             420                 425                 430
```

```
Glu Ile Lys Lys Arg His Ala Lys Gly Gln Pro Val Leu Val Gly Thr
            435                 440                 445

Val Ala Ile Glu Ser Ser Glu Arg Leu Ser His Leu Leu Asp Glu Ala
    450                 455                 460

Asn Ile Pro His Ala Val Leu Asn Ala Lys Asn His Ala Lys Glu Ala
465                 470                 475                 480

Gln Ile Ile Met Asn Ala Gly Gln Arg Gly Ala Val Thr Ile Ala Thr
                485                 490                 495

Asn Met Ala Gly Arg Gly Thr Asp Ile Lys Leu Gly Pro Gly Val Lys
                500                 505                 510

Glu Leu Gly Gly Leu Ala Val Ile Gly Thr Glu Arg His Glu Ser Arg
        515                 520                 525

Arg Ile Asp Asn Gln Leu Arg Gly Arg Ser Gly Arg Gln Gly Asp Pro
    530                 535                 540

Gly Tyr Thr Arg Phe Tyr Leu Ser Leu Glu Asp Asp Leu Met Lys Arg
545                 550                 555                 560

Phe Gly Gly Asp Arg Val Lys Asp Phe Leu Asp Arg Leu Ser Asp Asn
                565                 570                 575

Asp Asp Glu Lys Val Ile Glu Ser Arg Leu Ile Thr Arg Gln Val Glu
                580                 585                 590

Ser Ala Gln Lys Arg Val Glu Gly Asn Asn Tyr Asp Thr Arg Lys Gln
        595                 600                 605

Thr Leu Gln Tyr Asp Asp Val Met Arg Ile Gln Arg Glu Ile Ile Tyr
    610                 615                 620

Gly Glu Arg Met Gln Val Ile Glu Ala Asp Lys Ser Leu Lys Asn Val
625                 630                 635                 640

Leu Ile Pro Met Ile His Arg Thr Ile Asn Ser Gln Val Asp Met Phe
                645                 650                 655

Thr Gln Gly Asp Arg Ser Gln Trp Arg Leu Asp Ser Leu Arg Asp Phe
                660                 665                 670

Ile Ser Ser Ser Leu Ala Ser Glu Gln Val Thr Asp Ser Ile Asp Phe
        675                 680                 685

Lys Thr Ile Ser Val Glu Asp Leu Lys Lys Leu Tyr Asp Ile Val
    690                 695                 700

Glu Lys Asn Phe Glu Asp Lys Glu Lys Ala Leu Gly Asp Pro Ser Gln
705                 710                 715                 720

Met Leu Glu Phe Glu Lys Val Val Ile Leu Arg Val Val Asp Asp Arg
                725                 730                 735

Trp Thr Asp His Ile Asp Ala Met Asp Gln Leu Arg Gln Ser Ile Gly
                740                 745                 750

Leu Arg Gly Tyr Gly Gln Leu Asn Pro Leu Val Glu Tyr Gln Asp Ser
        755                 760                 765

Gly Tyr Arg Met Phe Glu Glu Met Ile Ser Asn Ile Glu Phe Asp Val
    770                 775                 780

Thr Arg Leu Phe Met Lys Ala Glu Ile Arg Gln Asn Leu Ser Arg
785                 790                 795

<210> SEQ ID NO 47
<211> LENGTH: 843
<212> TYPE: PRT
<213> ORGANISM: Staphylococcus aureus MW2

<400> SEQUENCE: 47

Met Gly Phe Leu Ser Lys Ile Leu Asp Gly Asn Asn Lys Glu Ile Lys
1               5                   10                  15
```

-continued

Gln Leu Gly Lys Leu Ala Asp Lys Val Ile Ala Leu Glu Glu Lys Thr
             20                  25                  30

Ala Ile Leu Thr Asp Glu Glu Ile Arg Asn Lys Thr Lys Gln Phe Gln
         35                  40                  45

Thr Glu Leu Ala Asp Ile Asp Asn Val Lys Lys Gln Asn Asp Tyr Leu
 50                  55                  60

Asp Lys Ile Leu Pro Glu Ala Tyr Ala Leu Val Arg Glu Gly Ser Lys
 65                  70                  75                  80

Arg Val Phe Asn Met Thr Pro Tyr Lys Val Gln Ile Met Gly Gly Ile
                 85                  90                  95

Ala Ile His Lys Gly Asp Ile Ala Glu Met Arg Thr Gly Glu Gly Lys
            100                 105                 110

Thr Leu Thr Ala Thr Met Pro Thr Tyr Leu Asn Ala Leu Ala Gly Arg
            115                 120                 125

Gly Val His Val Ile Thr Val Asn Glu Tyr Leu Ser Ser Val Gln Ser
130                 135                 140

Glu Glu Met Ala Glu Leu Tyr Asn Phe Leu Gly Leu Thr Val Gly Leu
145                 150                 155                 160

Asn Leu Asn Ser Lys Thr Thr Glu Glu Lys Arg Glu Ala Tyr Ala Gln
                165                 170                 175

Asp Ile Thr Tyr Ser Thr Asn Asn Glu Leu Gly Phe Asp Tyr Leu Arg
            180                 185                 190

Asp Asn Met Val Asn Tyr Ser Glu Asp Arg Val Met Arg Pro Leu His
        195                 200                 205

Phe Ala Ile Ile Asp Glu Val Asp Ser Ile Leu Ile Asp Glu Ala Arg
210                 215                 220

Thr Pro Leu Ile Ile Ser Gly Glu Ala Glu Lys Ser Thr Ser Leu Tyr
225                 230                 235                 240

Thr Gln Ala Asn Val Phe Ala Lys Met Leu Lys Gln Asp Glu Asp Tyr
                245                 250                 255

Lys Tyr Asp Glu Lys Thr Lys Ala Val His Leu Thr Glu Gln Gly Ala
            260                 265                 270

Asp Lys Ala Glu Arg Met Phe Lys Val Glu Asn Leu Tyr Asp Val Gln
        275                 280                 285

Asn Val Asp Val Ile Ser His Ile Asn Thr Ala Leu Arg Ala His Val
290                 295                 300

Thr Leu Gln Arg Asp Val Asp Tyr Met Val Val Asp Gly Glu Val Leu
305                 310                 315                 320

Ile Val Asp Gln Phe Thr Gly Arg Thr Met Pro Gly Arg Arg Phe Ser
                325                 330                 335

Glu Gly Leu His Gln Ala Ile Glu Ala Lys Glu Gly Val Gln Ile Gln
            340                 345                 350

Asn Glu Ser Lys Thr Met Ala Ser Ile Thr Phe Gln Asn Tyr Phe Arg
        355                 360                 365

Met Tyr Asn Lys Leu Ala Gly Met Thr Gly Thr Ala Lys Thr Glu Glu
370                 375                 380

Glu Glu Phe Arg Asn Ile Tyr Asn Met Thr Val Thr Gln Ile Pro Thr
385                 390                 395                 400

Asn Lys Pro Val Gln Arg Asn Asp Lys Ser Asp Leu Ile Tyr Ile Ser
                405                 410                 415

Gln Lys Gly Lys Phe Asp Ala Val Val Glu Asp Val Val Glu Lys His
            420                 425                 430

```
Lys Ala Gly Gln Pro Val Leu Leu Gly Thr Val Ala Val Glu Thr Ser
            435                 440                 445
Glu Tyr Ile Ser Asn Leu Leu Lys Lys Arg Gly Ile Arg His Asp Val
        450                 455                 460
Leu Asn Ala Lys Asn His Glu Arg Glu Ala Glu Ile Val Ala Gly Ala
465                 470                 475                 480
Gly Gln Lys Gly Ala Val Thr Ile Ala Thr Asn Met Ala Gly Arg Gly
                485                 490                 495
Thr Asp Ile Lys Leu Gly Glu Gly Val Glu Glu Leu Gly Gly Leu Ala
            500                 505                 510
Val Ile Gly Thr Glu Arg His Glu Ser Arg Arg Ile Asp Asp Gln Leu
        515                 520                 525
Arg Gly Arg Ser Gly Arg Gln Gly Asp Lys Gly Asp Ser Arg Phe Tyr
    530                 535                 540
Leu Ser Leu Gln Asp Glu Leu Met Ile Arg Phe Gly Ser Glu Arg Leu
545                 550                 555                 560
Gln Lys Met Met Ser Arg Leu Gly Leu Asp Asp Ser Thr Pro Ile Glu
                565                 570                 575
Ser Lys Met Val Ser Arg Ala Val Glu Ser Ala Gln Lys Arg Val Glu
            580                 585                 590
Gly Asn Asn Phe Asp Ala Arg Lys Arg Ile Leu Glu Tyr Asp Glu Val
        595                 600                 605
Leu Arg Lys Gln Arg Glu Ile Ile Tyr Asn Glu Arg Asn Ser Ile Ile
    610                 615                 620
Asp Glu Glu Asp Ser Ser Gln Val Val Asp Ala Met Leu Arg Ser Thr
625                 630                 635                 640
Leu Gln Arg Ser Ile Asn Tyr Tyr Ile Asn Thr Ala Asp Asp Glu Pro
                645                 650                 655
Glu Tyr Gln Pro Phe Ile Asp Tyr Ile Asn Asp Ile Phe Leu Gln Glu
            660                 665                 670
Gly Asp Ile Thr Glu Asp Ile Lys Gly Lys Asp Ala Glu Asp Ile
        675                 680                 685
Phe Glu Val Val Trp Ala Lys Ile Glu Ala Ala Tyr Gln Ser Gln Lys
    690                 695                 700
Asp Ile Leu Glu Glu Gln Met Asn Glu Phe Glu Arg Met Ile Leu Leu
705                 710                 715                 720
Arg Ser Ile Asp Ser His Trp Thr Asp His Ile Asp Thr Met Asp Gln
                725                 730                 735
Leu Arg Gln Gly Ile His Leu Arg Ser Tyr Ala Gln Gln Asn Pro Leu
            740                 745                 750
Arg Asp Tyr Gln Asn Glu Gly His Glu Leu Phe Asp Ile Met Met Gln
        755                 760                 765
Asn Ile Glu Glu Asp Thr Cys Lys Phe Ile Leu Lys Ser Val Val Gln
    770                 775                 780
Val Glu Asp Asn Ile Glu Arg Glu Lys Thr Thr Glu Phe Gly Glu Ala
785                 790                 795                 800
Lys His Val Ser Ala Glu Asp Gly Lys Glu Lys Val Lys Pro Lys Pro
                805                 810                 815
Ile Val Lys Gly Asp Gln Val Gly Arg Asn Asp Asp Cys Pro Cys Gly
            820                 825                 830
Ser Gly Lys Lys Phe Lys Asn Cys His Gly Lys
    835                 840
```

```
<210> SEQ ID NO 48
<211> LENGTH: 845
<212> TYPE: PRT
<213> ORGANISM: Corynebacterium glutamicum DSM 20300

<400> SEQUENCE: 48

Met Phe Gly Leu Ser Lys Val Leu Arg Val Gly Glu Gly Arg Ala Val
1               5                   10                  15

Lys Arg Leu His Lys Ile Ala Asp Gln Val Ile Ala Leu Glu Asp Lys
            20                  25                  30

Phe Ala Asn Leu Thr Asp Glu Glu Leu Lys Ala Lys Thr Ala Glu Phe
        35                  40                  45

Lys Glu Arg Ile Ala Gly Gly Glu Gly Leu Asp Glu Ile Phe Leu Glu
    50                  55                  60

Ala Phe Ala Thr Ala Arg Glu Ala Ala Trp Arg Val Leu Gly Gln Lys
65                  70                  75                  80

His Tyr His Val Gln Ile Met Gly Gly Ala Leu His Phe Gly Asn
                85                  90                  95

Val Ala Glu Met Arg Thr Gly Glu Gly Lys Thr Leu Thr Cys Val Leu
            100                 105                 110

Pro Ala Tyr Leu Asn Ala Leu Glu Gly Lys Gly Val His Val Val Thr
        115                 120                 125

Val Asn Asp Tyr Leu Ala Lys Arg Asp Ala Glu Met Met Gly Arg Val
    130                 135                 140

His Arg Tyr Leu Gly Leu Glu Val Gly Val Ile Leu Ser Asp Met Arg
145                 150                 155                 160

Pro Asp Glu Arg Arg Glu Ala Tyr Ala Ala Asp Ile Thr Tyr Gly Thr
                165                 170                 175

Asn Asn Glu Leu Gly Phe Asp Tyr Leu Arg Asp Asn Met Ala Arg Ser
            180                 185                 190

Leu Ser Asp Leu Val Gln Arg Gly His Asn Tyr Ala Ile Val Asp Glu
        195                 200                 205

Val Asp Ser Ile Leu Ile Asp Glu Ala Arg Thr Pro Leu Ile Ile Ser
    210                 215                 220

Gly Pro Val Asp Gly Thr Ser Gln Phe Tyr Asn Val Phe Ala Gln Ile
225                 230                 235                 240

Val Pro Arg Met Thr Lys Asp Val His Tyr Glu Val Asp Glu Arg Lys
                245                 250                 255

Lys Thr Val Gly Val Lys Glu Glu Gly Val Glu Tyr Val Glu Asp Gln
            260                 265                 270

Leu Gly Ile Asp Asn Leu Tyr Ala Pro Glu His Ser Gln Leu Val Ser
        275                 280                 285

Tyr Leu Asn Asn Ala Ile Lys Ala Gln Glu Leu Phe Thr Arg Asp Lys
    290                 295                 300

Asp Tyr Ile Val Arg Asn Gly Glu Val Met Ile Val Asp Gly Phe Thr
305                 310                 315                 320

Gly Arg Val Leu Ala Gly Arg Arg Tyr Asn Glu Gly Met His Gln Ala
                325                 330                 335

Ile Glu Ala Lys Glu Arg Val Glu Ile Lys Asn Glu Asn Gln Thr Leu
            340                 345                 350

Ala Thr Val Thr Leu Gln Asn Tyr Phe Arg Leu Tyr Thr Lys Leu Ala
        355                 360                 365

Gly Met Thr Gly Thr Ala Glu Thr Glu Ala Ala Glu Leu Asn Gln Ile
    370                 375                 380
```

```
Tyr Lys Leu Asp Val Ile Ala Ile Pro Thr Asn Arg Pro Asn Gln Arg
385                 390                 395                 400

Glu Asp Leu Thr Asp Leu Val Tyr Lys Thr Gln Glu Ala Lys Phe Ala
                405                 410                 415

Ala Val Val Asp Asp Ile Ala Glu Arg Thr Lys Gly Gln Pro Val
            420                 425                 430

Leu Val Gly Thr Val Ser Val Glu Arg Ser Glu Tyr Leu Ser Gln Leu
            435                 440                 445

Leu Thr Lys Arg Gly Ile Lys His Asn Val Leu Asn Ala Lys His His
    450                 455                 460

Glu Gln Glu Ala Gln Ile Val Ala Gln Ala Gly Leu Pro Gly Ala Val
465                 470                 475                 480

Thr Val Ala Thr Asn Met Ala Gly Arg Gly Thr Asp Ile Val Leu Gly
                485                 490                 495

Gly Asn Pro Glu Ile Leu Leu Asp Ile Lys Leu Arg Glu Arg Gly Leu
            500                 505                 510

Asp Pro Phe Glu Asp Glu Glu Ser Tyr Gln Glu Ala Trp Asp Ala Glu
            515                 520                 525

Leu Pro Ala Met Lys Gln Arg Cys Glu Glu Arg Gly Asp Lys Val Arg
530                 535                 540

Glu Ala Gly Gly Leu Tyr Val Leu Gly Thr Glu Arg His Glu Ser Arg
545                 550                 555                 560

Arg Ile Asp Asn Gln Leu Arg Gly Arg Ser Ala Arg Gln Gly Asp Pro
                565                 570                 575

Gly Ser Thr Arg Phe Tyr Leu Ser Met Arg Asp Asp Leu Met Val Arg
            580                 585                 590

Phe Val Gly Pro Thr Met Glu Asn Met Met Asn Arg Leu Asn Val Pro
            595                 600                 605

Asp Asp Val Pro Ile Glu Ser Lys Thr Val Thr Asn Ser Ile Lys Gly
            610                 615                 620

Ala Gln Ala Gln Val Glu Asn Gln Asn Phe Glu Met Arg Lys Asn Val
625                 630                 635                 640

Leu Lys Tyr Asp Glu Val Met Asn Glu Gln Arg Lys Val Ile Tyr Ser
                645                 650                 655

Glu Arg Arg Glu Ile Leu Glu Ser Ala Asp Ile Ser Arg Tyr Ile Gln
            660                 665                 670

Asn Met Ile Glu Glu Thr Val Ser Ala Tyr Val Asp Gly Ala Thr Ala
                675                 680                 685

Asn Gly Tyr Val Glu Asp Trp Asp Leu Asp Lys Leu Trp Asn Ala Leu
            690                 695                 700

Glu Ala Leu Tyr Asp Pro Ser Ile Asn Trp Thr Asp Leu Val Glu Gly
705                 710                 715                 720

Ser Glu Tyr Gly Lys Pro Gly Glu Leu Ser Ala Glu Asp Leu Arg Thr
                725                 730                 735

Ala Leu Val Asn Asp Ala His Ala Glu Tyr Ala Lys Leu Glu Glu Ala
            740                 745                 750

Val Ser Ala Ile Gly Gly Glu Ala Gln Ile Arg Asn Ile Glu Arg Met
        755                 760                 765

Val Leu Met Pro Val Ile Asp Thr Lys Trp Arg Glu His Leu Tyr Glu
        770                 775                 780

Met Asp Tyr Leu Lys Glu Gly Ile Gly Leu Arg Ala Met Ala Gln Arg
785                 790                 795                 800

Asp Pro Leu Val Glu Tyr Gln Lys Glu Gly Gly Asp Met Phe Asn Gly
```

-continued

```
                    805                 810                 815
Met Lys Asp Gly Ile Lys Glu Glu Thr Val Arg Gln Leu Phe Leu Leu
                820                 825                 830

Arg Lys Gln Phe Ile Lys Gln Asp Ala Glu Val Ala Asp
            835                 840                 845

<210> SEQ ID NO 49
<211> LENGTH: 911
<212> TYPE: PRT
<213> ORGANISM: Pseudomonas putida GB-1

<400> SEQUENCE: 49

Met Phe Ala Pro Leu Leu Lys Lys Leu Phe Gly Ser Lys Asn Glu Arg
1               5                   10                  15

Glu Val Lys Arg Met Leu Lys Thr Val Ser Ile Val Asn Ala Phe Glu
            20                  25                  30

Glu Lys Met Val Ala Leu Ser Asp Glu Gln Leu Arg Gly Lys Thr Ala
        35                  40                  45

Glu Phe Lys Glu Arg Leu Ala Lys Gly Glu Thr Leu Asp Gln Leu Leu
    50                  55                  60

Pro Glu Ala Phe Ala Val Ala Arg Glu Ala Gly Lys Arg Val Met Gly
65                  70                  75                  80

Met Arg His Phe Asp Val Gln Leu Ile Gly Gly Met Thr Leu His Glu
                85                  90                  95

Gly Met Ile Ala Glu Met Arg Thr Gly Glu Gly Lys Thr Leu Val Gly
            100                 105                 110

Thr Leu Ala Val Tyr Leu Asn Ala Leu Ser Gly Lys Gly Val His Val
        115                 120                 125

Val Thr Val Asn Asp Tyr Leu Ala Arg Arg Asp Ala Asn Trp Met Arg
130                 135                 140

Pro Leu Tyr Glu Phe Leu Gly Leu Ser Val Gly Ile Val Ser Ala Phe
145                 150                 155                 160

Gln Pro Pro Glu Glu Lys Arg Ala Ala Tyr Ala Ser Asp Ile Thr Tyr
                165                 170                 175

Gly Thr Asn Asn Glu Phe Gly Phe Asp Tyr Leu Arg Asp Asn Met Ala
            180                 185                 190

Phe Ser Gln Glu Glu Lys Phe Gln Arg Glu Leu Asn Phe Ala Val Ile
        195                 200                 205

Asp Glu Val Asp Ser Ile Leu Ile Asp Glu Ala Arg Thr Pro Leu Ile
    210                 215                 220

Ile Ser Gly Gln Ala Glu Asp Ser Ser Lys Leu Tyr Ile Glu Ile Asn
225                 230                 235                 240

Arg Leu Ile Pro Arg Leu Thr Gln His Ile Glu Glu Val Glu Gly Gln
                245                 250                 255

Val Thr Gln Glu Gly His Phe Thr Ile Asp Glu Lys Ser Arg Gln Val
            260                 265                 270

Glu Leu Asn Glu Ala Gly His Gln Phe Ile Glu Glu Met Leu Thr Gln
        275                 280                 285

Ala Gly Leu Leu Ala Glu Gly Glu Ser Leu Tyr Ser Ala His Asn Leu
    290                 295                 300

Gly Leu Leu Thr His Val Tyr Ala Gly Leu Arg Ala His Lys Leu Phe
305                 310                 315                 320

His Arg Asn Val Glu Tyr Ile Val Gln Asp Gly Gln Val Leu Leu Ile
                325                 330                 335
```

```
Asp Glu His Thr Gly Arg Thr Met Pro Gly Arg Arg Leu Ser Glu Gly
                340                 345                 350

Leu His Gln Ala Ile Glu Ala Lys Glu Asn Leu Asn Ile Gln Ala Glu
            355                 360                 365

Ser Gln Thr Leu Ala Ser Thr Thr Phe Gln Asn Tyr Phe Arg Leu Tyr
        370                 375                 380

Thr Lys Leu Ser Gly Met Thr Gly Thr Ala Asp Thr Glu Ala Phe Glu
385                 390                 395                 400

Phe Gln Ser Ile Tyr Ala Leu Asn Val Met Val Ile Pro Pro Asn Lys
                405                 410                 415

Pro Leu Ala Arg Lys Asp Phe Asn Asp Leu Val Tyr Leu Thr Ala Asp
            420                 425                 430

Glu Lys Tyr Ala Ala Ile Ile Ala Asp Ile Lys Glu Ser Met Thr Lys
        435                 440                 445

Gly Arg Pro Ile Leu Val Gly Thr Ala Thr Ile Glu Thr Ser Glu His
450                 455                 460

Met Ser Asn Leu Leu Lys Lys Glu Gly Ile Asp His Lys Val Leu Asn
465                 470                 475                 480

Ala Lys Tyr His Glu Lys Glu Ala Glu Ile Ile Ala Gln Ala Gly Ala
                485                 490                 495

Pro Gly Ala Leu Thr Ile Ala Thr Asn Met Ala Gly Arg Gly Thr Asp
            500                 505                 510

Ile Leu Leu Gly Gly Asn Trp Glu Ala Glu Val Ala Ala Leu Glu Asn
        515                 520                 525

Pro Ser Ala Glu Gln Ile Ala Gln Ile Lys Ala Asp Trp Gln Lys Arg
530                 535                 540

His Gln Gln Val Ile Glu Ala Gly Gly Leu His Val Ile Ala Ser Glu
545                 550                 555                 560

Arg His Glu Ser Arg Arg Ile Asp Asn Gln Leu Arg Gly Arg Ser Gly
                565                 570                 575

Arg Gln Gly Asp Pro Gly Ser Ser Arg Phe Tyr Leu Ser Leu Glu Asp
            580                 585                 590

Ser Leu Met Arg Ile Phe Ala Ser Asp Arg Val Lys Asn Phe Met Lys
        595                 600                 605

Ala Leu Gly Met Gln Ser Gly Glu Ala Ile Glu His Arg Met Val Thr
610                 615                 620

Asn Ala Ile Glu Lys Ala Gln Arg Lys Val Glu Gly Arg Asn Phe Asp
625                 630                 635                 640

Ile Arg Lys Gln Leu Leu Glu Tyr Asp Asp Val Ala Asn Glu Gln Arg
                645                 650                 655

Lys Val Ile Tyr His Met Arg Asn Ser Leu Leu Ala Ala Glu Asn Ile
            660                 665                 670

Gly Asp Thr Ile Val Glu Phe Arg Gln Glu Val Leu Asp Ala Thr Ile
        675                 680                 685

Ser Gln His Ile Pro Pro Gln Ser Leu Pro Glu Gln Trp Asp Val Ala
690                 695                 700

Gly Leu Glu Ala Ser Leu Ala Ser Asp Phe Ala Met Lys Leu Pro Ile
705                 710                 715                 720

Gln Gln Trp Leu Asp Glu Asp His Leu Tyr Glu Glu Thr Leu Arg
                725                 730                 735

Glu Lys Leu Leu Asn Glu Ile Thr Thr Ala Tyr Thr Glu Lys Glu Asp
            740                 745                 750

Gln Ala Gly Ile Glu Ala Leu Arg Thr Phe Glu Lys Gln Ile Leu Leu
```

```
                755                 760                 765
Arg Val Leu Asp Asp Leu Trp Lys Asp His Leu Ser Thr Met Asp His
            770                 775                 780

Leu Arg His Gly Ile His Leu Arg Gly Tyr Ala Gln Lys Asn Pro Lys
785                 790                 795                 800

Gln Glu Tyr Lys Arg Glu Ser Phe Ser Leu Phe Gln Glu Leu Leu Glu
                805                 810                 815

Ser Ile Lys Arg Asp Thr Ile Arg Val Leu Ser His Val Gln Val Arg
            820                 825                 830

Arg Glu Asp Pro Ile Glu Glu Ala Arg Leu Arg Arg Glu Ala Glu
        835                 840                 845

Glu Leu Ala Ser Arg Met Gln Phe Gln His Ala Ala Ala Pro Gly Leu
        850                 855                 860

Glu Ser Glu Gln Leu Ser Glu Glu Gly Ala Glu Val Ala Val Ala Ala
865                 870                 875                 880

Ala Pro Val Arg Asn Asp Gln Lys Leu Gly Arg Asn Glu Pro Cys Trp
            885                 890                 895

Cys Gly Ser Gly Lys Lys Phe Lys His Cys His Gly Gln Ile Glu
                900                 905                 910

<210> SEQ ID NO 50
<211> LENGTH: 947
<212> TYPE: PRT
<213> ORGANISM: Streptomyces coelicolor A3(2)

<400> SEQUENCE: 50

Met Ser Val Leu Ser Lys Leu Met Arg Ala Gly Glu Gly Lys Ile Leu
1               5                   10                  15

Arg Lys Leu His Arg Ile Ala Asp Gln Val Asn Ser Ile Glu Glu Asp
            20                  25                  30

Phe Ala Asp Leu Ser Asp Ala Glu Leu Arg Ala Leu Thr Asp Glu Tyr
        35                  40                  45

Lys Gln Arg Tyr Ala Asp Gly Glu Ser Leu Asp Asp Leu Leu Pro Glu
    50                  55                  60

Ala Phe Ala Thr Val Arg Glu Ala Ala Lys Arg Val Leu Gly Gln Arg
65                  70                  75                  80

His Tyr Asp Val Gln Ile Met Gly Gly Ala Leu His Met Gly Tyr
                85                  90                  95

Val Ala Glu Met Lys Thr Gly Glu Gly Lys Thr Leu Val Gly Thr Leu
            100                 105                 110

Pro Ala Tyr Leu Asn Ala Leu Ser Gly Glu Gly Val His Ile Val Thr
        115                 120                 125

Val Asn Asp Tyr Leu Ala Glu Arg Asp Ser Glu Leu Met Gly Arg Val
    130                 135                 140

His Lys Phe Leu Gly Leu Asn Val Gly Cys Ile Leu Ala Asn Gln Thr
145                 150                 155                 160

Pro Ala Gln Arg Arg Glu Met Tyr Ala Cys Asp Ile Thr Tyr Gly Thr
                165                 170                 175

Asn Asn Glu Phe Gly Phe Asp Tyr Leu Arg Asp Asn Met Ala Trp Ser
            180                 185                 190

Lys Asp Glu Leu Val Gln Arg Gly His Asn Phe Ala Ile Val Asp Glu
        195                 200                 205

Val Asp Ser Ile Leu Val Asp Glu Ala Arg Thr Pro Leu Ile Ile Ser
    210                 215                 220
```

```
Gly Pro Ala Asp Gln Ala Thr Lys Trp Tyr Gly Asp Phe Ala Lys Leu
225                 230                 235                 240

Val Thr Arg Leu Lys Lys Gly Glu Ala Gly Asn Thr Leu Lys Gly Ile
            245                 250                 255

Glu Glu Thr Gly Asp Tyr Glu Val Asp Glu Lys Lys Arg Thr Val Ala
        260                 265                 270

Ile His Glu Ser Gly Val Ala Lys Val Glu Asp Trp Leu Gly Ile Asp
    275                 280                 285

Asn Leu Tyr Glu Ser Val Asn Thr Pro Leu Val Gly Tyr Leu Asn Asn
290                 295                 300

Ala Ile Lys Ala Lys Glu Leu Phe Lys Lys Asp Lys Asp Tyr Val Val
305                 310                 315                 320

Leu Asp Gly Glu Val Met Ile Val Asp Glu His Thr Gly Arg Ile Leu
            325                 330                 335

Ala Gly Arg Arg Tyr Asn Glu Gly Met His Gln Ala Ile Glu Ala Lys
        340                 345                 350

Glu Gly Val Asp Ile Lys Asp Glu Asn Gln Thr Leu Ala Thr Ile Thr
    355                 360                 365

Leu Gln Asn Phe Phe Arg Leu Tyr Lys Arg His Asp His Asp Gly Lys
370                 375                 380

Glu Gln Pro Gly Leu Ser Gly Met Thr Gly Thr Ala Met Thr Glu Ala
385                 390                 395                 400

Ala Glu Phe His Gln Ile Tyr Lys Leu Gly Val Val Pro Ile Pro Thr
            405                 410                 415

Asn Arg Pro Met Val Arg Lys Asp Gln Ser Asp Leu Ile Tyr Arg Thr
        420                 425                 430

Glu Val Ala Lys Phe Glu Ala Val Asp Asp Ile Glu Glu Lys His
    435                 440                 445

Arg Lys Gly Gln Pro Ile Leu Val Gly Thr Thr Ser Val Glu Lys Ser
450                 455                 460

Glu Tyr Leu Ser Gln Gln Leu Ser Lys Arg Gly Val Gln His Glu Val
465                 470                 475                 480

Leu Asn Ala Lys Gln His Asp Arg Glu Ala Thr Ile Val Ala Gln Ala
            485                 490                 495

Gly Arg Lys Gly Ser Val Thr Val Ala Thr Asn Met Ala Gly Arg Gly
        500                 505                 510

Thr Asp Ile Lys Leu Gly Gly Asn Pro Glu Asp Leu Ala Glu Ala Glu
    515                 520                 525

Leu Arg Gln Arg Gly Leu Asp Pro Glu Glu His Ile Glu Glu Trp Ala
530                 535                 540

Ala Ala Leu Pro Ala Ala Leu Glu Arg Ala Glu Gln Ala Val Lys Ala
545                 550                 555                 560

Glu Phe Glu Glu Val Lys Glu Leu Gly Gly Leu Tyr Val Leu Gly Thr
            565                 570                 575

Glu Arg His Glu Ser Arg Arg Ile Asp Asn Gln Leu Arg Gly Arg Ser
        580                 585                 590

Gly Arg Gln Gly Asp Pro Gly Glu Ser Arg Phe Tyr Leu Ser Leu Gly
    595                 600                 605

Asp Asp Leu Met Arg Leu Phe Lys Ala Gln Met Val Glu Arg Val Met
610                 615                 620

Ser Met Ala Asn Val Pro Asp Asp Val Pro Ile Glu Asn Lys Met Val
625                 630                 635                 640

Thr Arg Ala Ile Ala Ser Ala Gln Ser Gln Val Glu Thr Gln Asn Phe
```

-continued

```
                645                 650                 655
Glu Thr Arg Lys Asn Val Leu Lys Tyr Asp Glu Val Leu Asn Arg Gln
                    660                 665                 670

Arg Glu Val Ile Tyr Gly Arg Arg Val Leu Glu Gly Glu Asp
                675                 680                 685

Leu Gln Glu Gln Ile Gln His Phe Thr Asn Asp Thr Ile Asp Ala Tyr
            690                 695                 700

Val Gln Ala Glu Thr Ala Glu Gly Phe Pro Glu Asp Trp Asp Leu Asp
705                 710                 715                 720

Arg Leu Trp Gly Ala Phe Lys Gln Leu Tyr Pro Val Lys Val Thr Val
                    725                 730                 735

Glu Glu Leu Glu Glu Ala Ala Gly Asp Arg Ala Gly Leu Thr Ala Asp
                740                 745                 750

Tyr Ile Ala Glu Ser Ile Lys Asp Asp Val Arg Glu Gln Tyr Glu Ala
                755                 760                 765

Arg Glu Lys Gln Leu Gly Ser Glu Ile Met Arg Glu Leu Glu Arg Arg
            770                 775                 780

Val Val Leu Ser Val Leu Asp Arg Lys Trp Arg Glu His Leu Tyr Glu
785                 790                 795                 800

Met Asp Tyr Leu Gln Glu Gly Ile Gly Leu Arg Ala Met Ala Gln Lys
                    805                 810                 815

Asp Pro Leu Val Glu Tyr Gln Arg Glu Gly Phe Asp Met Phe Gln Ala
                820                 825                 830

Met Met Asp Gly Ile Lys Glu Glu Ser Val Gly Tyr Leu Phe Asn Leu
            835                 840                 845

Glu Val Gln Val Glu Gln Val Glu Val Pro Val Glu Asp Ala
850                 855                 860

Ala Pro Ser Leu Asp Lys Gly Ala Gln Asp Ala Val Pro Ala Gln Ala
865                 870                 875                 880

Gly Ala Arg Pro Glu Ile Arg Ala Lys Gly Leu Asp Ala Pro Gln Arg
                    885                 890                 895

Arg Asp Leu His Phe Ser Ala Pro Thr Val Asp Gly Glu Gly Gly Val
                900                 905                 910

Val Glu Gly Glu Phe Thr Asp Gly Glu Pro Ala Gln Ala Gln Ser Asp
            915                 920                 925

Gly Leu Thr Arg Ala Glu Arg Arg Lys Gln Ala Lys Gly Gly Arg Arg
        930                 935                 940

Arg Lys Lys
945

<210> SEQ ID NO 51
<211> LENGTH: 921
<212> TYPE: PRT
<213> ORGANISM: Gluconobacter oxydans 621H

<400> SEQUENCE: 51

Met Phe Ala Arg Leu Ala Arg Ala Leu Phe Gly Ser Ala Asn Asp Arg
1               5                   10                  15

Thr Leu Lys Ala Tyr Gln Arg Arg Val Pro Glu Ile Asn Ala Leu Glu
                20                  25                  30

Pro Ala Val Gln Ala Leu Ser Asp Glu Gln Leu Arg His Lys Thr Thr
            35                  40                  45

Glu Phe Lys Glu Arg Leu Glu Lys Gly Glu Thr Leu Asp Gly Leu Leu
        50                  55                  60
```

-continued

```
Pro Glu Ala Phe Ala Val Cys Arg Glu Ala Ser Arg Arg Val Leu Gly
 65                  70                  75                  80

Lys Arg His Phe Asp Val Gln Leu Ile Gly Gly Met Val Leu His Ala
                 85                  90                  95

Gly Arg Ile Ala Glu Met Arg Thr Gly Glu Gly Lys Thr Leu Val Ala
            100                 105                 110

Thr Leu Ala Val Tyr Leu Asn Ala Leu Ser Gly Lys Gly Val His Val
        115                 120                 125

Val Thr Val Asn Asp Tyr Leu Ala Arg Arg Asp Ala Glu Glu Met Ser
    130                 135                 140

Ile Leu Tyr Ser Phe Leu Gly Leu Thr Thr Gly Val Ile Val Pro Asn
145                 150                 155                 160

Leu Ser Asp Gly Glu Arg Arg Glu Ala Tyr Ala Ala Asp Ile Thr Tyr
                165                 170                 175

Gly Thr Asn Asn Glu Phe Gly Phe Asp Tyr Leu Arg Asp Asn Met Lys
            180                 185                 190

Tyr Ser Leu Ala Asp Met Val Gln Arg Pro Phe Asn His Ala Ile Val
        195                 200                 205

Asp Glu Val Asp Ser Ile Leu Ile Asp Glu Ala Arg Thr Pro Leu Ile
    210                 215                 220

Ile Ser Gly Pro Ala Asp Asp Ser Ser Asp Leu Tyr Arg Ser Val Asp
225                 230                 235                 240

Asp Val Val Val Lys Leu Val Gln Glu Pro Asp Val Tyr Asp Lys Asp
                245                 250                 255

Glu Lys Leu Arg Ser Val Thr Leu Thr Glu His Gly Ser His Arg Val
            260                 265                 270

Glu Glu Leu Leu Ala Glu Ala Gly Val Leu Gln Asp Gly Gly Leu Tyr
        275                 280                 285

Asp Ile His Asn Val Ala Val Val His His Val Gln Gln Ser Leu Arg
    290                 295                 300

Ala His Thr Leu Phe Thr Arg Asp Val Asp Tyr Ile Val Arg Asp Gly
305                 310                 315                 320

Lys Val Val Ile Ile Asp Glu Phe Thr Gly Arg Met Met Asp Gly Arg
                325                 330                 335

Arg Tyr Ser Asp Gly Leu His Gln Ala Leu Glu Ala Lys Glu His Val
            340                 345                 350

Glu Ile Gln Gln Glu Asn Gln Thr Leu Ala Ser Ile Thr Phe Gln Asn
        355                 360                 365

Tyr Phe Arg Leu Tyr Pro Lys Leu Ser Gly Met Thr Gly Thr Ala Met
    370                 375                 380

Thr Glu Ala Asp Glu Phe Ala Glu Ile Tyr His Leu Asp Val Val Glu
385                 390                 395                 400

Ile Pro Thr Asn Leu Pro Val Arg Arg Ile Asp Thr Asp Asp Glu Val
                405                 410                 415

Tyr Leu Thr Ala Ala Glu Lys Phe Ser Ala Val Ala Asp Leu Ile Lys
            420                 425                 430

Glu Ile His Glu Thr Gly Gln Pro Ile Leu Val Gly Thr Thr Ser Ile
        435                 440                 445

Glu Lys Ser Glu Tyr Leu Ser His Ile Leu Thr Gln Arg Gly Ile Pro
    450                 455                 460

His Asn Val Leu Asn Ala Arg Gln His Glu Lys Glu Ala Ile Ile Val
465                 470                 475                 480

Ala Gln Ala Gly Ala Pro Gly Ala Ile Thr Ile Ala Thr Asn Met Ala
```

-continued

```
                485                 490                 495
Gly Arg Gly Thr Asp Ile Lys Leu Gly Gly Asn Ile Glu Met Leu Val
                    500                 505                 510
Lys Ala Ser Thr Glu Gly Val Glu Asp Glu Ala Gln Arg Glu Ser Val
                    515                 520                 525
Glu Gln Asn Ile Arg Ala Ile Val Glu Glu His His Glu Glu Val His
                    530                 535                 540
Lys Ala Gly Gly Leu Tyr Val Ile Gly Thr Glu Arg His Glu Ser Arg
545                 550                 555                 560
Arg Val Asp Asn Gln Leu Arg Gly Arg Ser Gly Arg Gln Gly Asp Pro
                    565                 570                 575
Gly Asn Ser Arg Phe Phe Leu Ser Leu Glu Asp Asp Leu Ile Arg Ile
                    580                 585                 590
Phe Ala Ser Asp Arg Met Gly Ala Met Met Gln Lys Met Gly Leu Lys
                    595                 600                 605
Glu Gly Glu Ala Ile Val His Pro Trp Leu Asn Lys Ala Leu Glu Lys
                    610                 615                 620
Ala Gln Lys Arg Val Glu Ala Arg Asn Phe Asp Met Arg Lys Asn Thr
625                 630                 635                 640
Leu Lys Tyr Asp Asp Val Met Asn Asp Gln Arg Lys Glu Val Tyr Ala
                    645                 650                 655
Gln Arg Arg Glu Tyr Met Ala Thr Asp Asp Leu Ser Gly Val Ile Ala
                    660                 665                 670
Glu Leu Arg Glu His Thr Ile Glu Asp Leu Val His Ala His Ile Pro
                    675                 680                 685
Glu Lys Ser Phe Ala Glu Ala Trp Asp Thr Glu Gly Leu Thr Lys Glu
                    690                 695                 700
Val Ser Arg Ile Leu Asn Leu Asp Leu Pro Ile Ala Asp Trp Ala Lys
705                 710                 715                 720
Glu Asp Gly Met Asp Ser Glu Gly Val Ile Glu Arg Ile Glu Ala Glu
                    725                 730                 735
Ala Ala Lys Ala Gln Ala Ala Arg Thr Ala Asn Met Gly Pro Glu Leu
                    740                 745                 750
Met Arg Leu Ile Glu Lys Gln Val Val Leu Thr Thr Phe Asp Ala Val
                    755                 760                 765
Trp Lys Glu Tyr Leu His Gly Leu Asp Gln Leu Arg Gln Gly Ile Gly
                    770                 775                 780
Leu Arg Ala Tyr Gly Gln Arg Asp Pro Leu Asn Glu Tyr Lys Gln Glu
785                 790                 795                 800
Ala Phe Gln Met Phe Thr Ala Met Leu Asp Asp Met Arg Ile Arg Val
                    805                 810                 815
Thr Glu Thr Met Cys Arg Ile Gln Ala Val Ser Glu Pro Pro Phe
                    820                 825                 830
Pro Val Ile Asn Thr Glu Thr Ser Gly Pro Ser Glu Pro Ala Gly
                    835                 840                 845
Leu Phe Ser Gln Gly Thr Thr Gly Gly Asp Ile Pro Ala Pro Gln Pro
                    850                 855                 860
Met Ala Gly Phe Pro Ser Ala Pro Met Pro Arg Pro Gln Pro
865                 870                 875                 880
Val Pro Thr Gly Ala Glu Pro Asp Ala Ala Thr Leu Gln Arg Trp Tyr
                    885                 890                 895
Ala Glu Thr Pro Arg Asn Ala Leu Cys Pro Cys Gly Ser Gly Leu Lys
                    900                 905                 910
```

```
Phe Lys His Cys His Gly Arg Leu Ala
        915                 920

<210> SEQ ID NO 52
<211> LENGTH: 839
<212> TYPE: PRT
<213> ORGANISM: Clostridium acetobutylicum DSM 792

<400> SEQUENCE: 52

Met Gly Leu Leu Glu Lys Ile Phe Gly Thr Tyr Ser Asp Arg Glu Val
1               5                   10                  15

Lys Arg Ile Ile Pro Leu Val Asp Lys Ile Asp Ala Leu Asp Gly Ser
            20                  25                  30

Met Gln Ala Leu Ser Glu Asp Glu Leu Lys Ala Lys Thr Ala Glu Phe
        35                  40                  45

Lys Gln Arg Tyr Glu Asn Gly Glu Thr Leu Asp Asp Leu Leu Val Glu
    50                  55                  60

Ala Phe Ala Val Val Arg Glu Ala Ser Ser Arg Ile Leu Gly Leu Lys
65                  70                  75                  80

His Phe Arg Glu Gln Ile Ile Gly Gly Ile Val Leu His Gln Gly Arg
                85                  90                  95

Ile Ser Glu Met Lys Thr Gly Glu Gly Lys Thr Leu Val Ala Thr Leu
            100                 105                 110

Pro Ser Tyr Leu Asn Ala Ile Thr Gly Lys Gly Val His Val Val Thr
        115                 120                 125

Val Asn Asp Tyr Leu Ala Lys Arg Asp Met Glu Trp Met Gly Gln Leu
130                 135                 140

Tyr Gln Tyr Leu Gly Leu Thr Thr Gly Val Ile Val His Asp Leu Asp
145                 150                 155                 160

Gln Lys Gln Arg Gln Glu Ala Tyr Ala Ala Asp Ile Thr Tyr Gly Thr
                165                 170                 175

Asn Asn Glu Phe Gly Phe Asp Tyr Leu Arg Asp Asn Met Val Ile Tyr
            180                 185                 190

Lys Glu Glu Arg Val Gln Arg Pro Leu His Phe Cys Ile Val Asp Glu
        195                 200                 205

Val Asp Ser Ile Leu Ile Asp Glu Ala Arg Thr Pro Leu Ile Ile Ser
    210                 215                 220

Gly Glu Gly Glu Lys Ser Thr Glu Phe Tyr Lys Val Ala Asp Asn Phe
225                 230                 235                 240

Ala Lys Met Leu Arg Lys Glu Lys Asp Phe Thr Ile Asp Glu Lys Thr
                245                 250                 255

Asn Ser Ala Ile Leu Thr Asp Glu Gly Val Glu Lys Ala Glu Lys Tyr
            260                 265                 270

Tyr His Ile Asp Asn Tyr Ala Asp Pro Gln Asn Met Glu Ile Gln His
        275                 280                 285

His Thr Ser Gln Ala Leu Lys Ala Asn Tyr Leu Met Lys Arg Asp Lys
    290                 295                 300

Asp Tyr Met Val Lys Glu Asp Glu Val Val Ile Val Asp Glu Phe Thr
305                 310                 315                 320

Gly Arg Leu Met Glu Gly Arg Arg Tyr Ser Asp Gly Leu His Gln Ala
                325                 330                 335

Ile Glu Ala Lys Glu Gly Val Lys Val Gln Lys Glu Ser Lys Thr Leu
            340                 345                 350

Ala Thr Ile Thr Phe Gln Asn Tyr Phe Arg Met Tyr Glu Lys Leu Ser
```

-continued

```
            355                 360                 365
Gly Met Thr Gly Thr Ala Leu Thr Glu Glu Val Glu Phe Arg Glu Ile
            370                 375                 380
Tyr Gly Leu Asp Val Val Ile Pro Thr His Arg Pro Ile Ala Arg
385                     390                 395                 400
Ile Asp Ala Pro Asp Ile Val Tyr Lys Thr Glu Leu Gly Lys Phe Lys
                    405                 410                 415
Ala Val Val Glu Asp Ile Val Glu Thr Asn Lys Asn Gly Gln Pro Val
                420                 425                 430
Leu Val Gly Thr Val Ser Ile Glu Lys Ser Glu Leu Leu Ser Ser Leu
            435                 440                 445
Leu Lys Lys Arg Gly Val Arg His Gln Val Leu Asn Ala Lys Tyr His
        450                 455                 460
Glu Gln Glu Ala Glu Ile Ile Ser His Ala Gly Glu Lys Gly Met Val
465                 470                 475                 480
Thr Ile Ala Thr Asn Met Ala Gly Arg Gly Thr Asp Ile Lys Leu Gly
                    485                 490                 495
Glu Gly Val Thr Asp Val Gly Gly Leu Lys Ile Ile Gly Thr Glu Arg
                500                 505                 510
His Glu Ser Arg Arg Ile Asp Asn Gln Leu Arg Gly Arg Ala Gly Arg
            515                 520                 525
Gln Gly Asp Lys Gly Tyr Ser Arg Phe Tyr Val Ser Leu Glu Asp Asp
        530                 535                 540
Leu Met Arg Ile Phe Gly Ser Asp Lys Leu Lys Asn Met Val Glu Lys
545                 550                 555                 560
Leu Gly Leu Gly Asp Asp Ala Ile Glu Ser Lys Met Val Ser Ser
                    565                 570                 575
Ala Ile Glu Asn Ala Gln Lys Lys Val Glu Gly Asn Asn Phe Asp Ile
                580                 585                 590
Arg Lys Thr Leu Ile Gln Tyr Asp Asp Val Met Asn Lys Gln Arg Glu
            595                 600                 605
Ile Ile Tyr Lys Gln Arg Ser Glu Val Leu Glu Gly Glu Asn Leu Lys
        610                 615                 620
Asp Gln Ile Glu Gly Met Ile Lys Asp Leu Ile Tyr Asn Ala Val Asn
625                 630                 635                 640
Ser His Ile Ser Gly Val Asp Glu Glu Leu Glu Ser Asp Ile Glu Ala
                    645                 650                 655
Ile Leu Asn Tyr Leu Asp Asp Ile Cys Leu Pro Arg Gly Ile Val Glu
                660                 665                 670
Val Glu Glu Leu Ala Thr Met Ser Asn Asp Glu Ile Lys Glu Lys Leu
            675                 680                 685
Tyr Ser Leu Ala Lys Glu Ile Tyr Glu Arg Lys Glu Glu Phe Ser
        690                 695                 700
Ser Asp Gln Met Arg Glu Leu Glu Arg Val Ile Leu Arg Val Val
705                 710                 715                 720
Asp Thr Lys Trp Met Asp His Ile Asp Ser Met Glu His Leu Lys Gln
                    725                 730                 735
Gly Ile Gly Leu Arg Ala Tyr Lys Gln Gln Asp Pro Thr Gln Ala Tyr
                740                 745                 750
Gln Met Glu Gly Ser Asp Met Phe Glu Glu Met Val Glu Asn Ile Lys
            755                 760                 765
Val Glu Thr Val Arg Tyr Leu Phe His Val Gln Ala Glu Arg Ala Pro
        770                 775                 780
```

```
Glu Arg Gln Arg Val Val Lys Glu Thr Glu Ile Asn Tyr Ser Gly Pro
785                 790                 795                 800

Asp Ala Gly Asp Thr Lys Lys Glu Pro Val Arg Arg Lys Glu Lys Lys
            805                 810                 815

Ile Gly Arg Asn Asp Leu Cys Pro Cys Gly Ser Gly Lys Lys Tyr Lys
        820                 825                 830

Asp Cys Cys Gly Arg Arg Ala
        835

<210> SEQ ID NO 53
<211> LENGTH: 37
<212> TYPE: DNA
<213> ORGANISM: Bacillus atrophaeus

<400> SEQUENCE: 53
aaattctttg gaaataacag aaggtatgat atgataa                            37

<210> SEQ ID NO 54
<211> LENGTH: 37
<212> TYPE: DNA
<213> ORGANISM: Bacillus subtilis

<400> SEQUENCE: 54
aaattctttg gaaatggcaa aaggtatgtt atgataa                            37

<210> SEQ ID NO 55
<211> LENGTH: 37
<212> TYPE: DNA
<213> ORGANISM: Bacillus sp.

<400> SEQUENCE: 55
aaattctttg gaaatagcaa aaggtatgtt atgataa                            37

<210> SEQ ID NO 56
<211> LENGTH: 37
<212> TYPE: DNA
<213> ORGANISM: Bacillus siamensis

<400> SEQUENCE: 56
aaattctttg gaaataacca aaggtatgtt atgataa                            37

<210> SEQ ID NO 57
<211> LENGTH: 37
<212> TYPE: DNA
<213> ORGANISM: Bacillus sp.

<400> SEQUENCE: 57
aaattctttg gaaatgaaag aaggtatggt atgataa                            37

<210> SEQ ID NO 58
<211> LENGTH: 37
<212> TYPE: DNA
<213> ORGANISM: Bacillus pumilus

<400> SEQUENCE: 58
aaattctttg gaaatgaagg aaggtatggt atgataa                            37

<210> SEQ ID NO 59
<211> LENGTH: 37
<212> TYPE: DNA
<213> ORGANISM: Bacillus mojavensis
```

```
<400> SEQUENCE: 59
aaattctttg gaaattagag aaggtatgat atgataa                              37

<210> SEQ ID NO 60
<211> LENGTH: 37
<212> TYPE: DNA
<213> ORGANISM: Bacillus subtilis

<400> SEQUENCE: 60
aaattctttg gaaataagag aaggtatgat atgataa                              37

<210> SEQ ID NO 61
<211> LENGTH: 37
<212> TYPE: DNA
<213> ORGANISM: Bacillus sp.

<400> SEQUENCE: 61
aaattctttg gaaataacaa aaggtgtgat atgataa                              37

<210> SEQ ID NO 62
<211> LENGTH: 37
<212> TYPE: DNA
<213> ORGANISM: Bacillus subtilis

<400> SEQUENCE: 62
aaattctttg gaaataacaa aaggtatgat atgataa                              37

<210> SEQ ID NO 63
<211> LENGTH: 37
<212> TYPE: DNA
<213> ORGANISM: Bacillus amyloliquefaciens

<400> SEQUENCE: 63
aaattctttg gaaataacaa aaggtatgtt atgataa                              37

<210> SEQ ID NO 64
<211> LENGTH: 37
<212> TYPE: DNA
<213> ORGANISM: Bacillus sp.

<400> SEQUENCE: 64
atatggtttg gaaatatcat aagatgtgat aaaataa                              37

<210> SEQ ID NO 65
<211> LENGTH: 37
<212> TYPE: DNA
<213> ORGANISM: Bacillus sp.

<400> SEQUENCE: 65
aaattctttg gaaatcaagg aaggtatggt atgataa                              37

<210> SEQ ID NO 66
<211> LENGTH: 37
<212> TYPE: DNA
<213> ORGANISM: Bacillus paralicheniformis

<400> SEQUENCE: 66
aaattgtttg gaaatgacaa aaggtatgat atgatat                              37

<210> SEQ ID NO 67
<211> LENGTH: 37
<212> TYPE: DNA
<213> ORGANISM: Bacillus glycinifermentans
```

<400> SEQUENCE: 67
aaattgtttg gaaatgacaa aggtgtgat atgatat                          37

<210> SEQ ID NO 68
<211> LENGTH: 37
<212> TYPE: DNA
<213> ORGANISM: Bacillus vallismortis

<400> SEQUENCE: 68
aaattctttg gaaataaccc aaggtatgat atgataa                         37

<210> SEQ ID NO 69
<211> LENGTH: 43
<212> TYPE: DNA
<213> ORGANISM: Shigella flexneri

<400> SEQUENCE: 69
tcattactgc tgtggagtgc gcgctttaat gataagattt gtg                  43

<210> SEQ ID NO 70
<211> LENGTH: 43
<212> TYPE: DNA
<213> ORGANISM: Citrobacter sp.

<400> SEQUENCE: 70
tcattactgc tgtggtgcga acgcattaat ggtaatattt gtg                  43

<210> SEQ ID NO 71
<211> LENGTH: 43
<212> TYPE: DNA
<213> ORGANISM: Salmonella bongori

<400> SEQUENCE: 71
tcattactgc tgttgcgtgt acgctttaat gataagattt gtg                  43

<210> SEQ ID NO 72
<211> LENGTH: 43
<212> TYPE: DNA
<213> ORGANISM: Salmonella enterica

<400> SEQUENCE: 72
tcattactgc tgtagcgcgt acgctttaat gataagattt gtg                  43

<210> SEQ ID NO 73
<211> LENGTH: 43
<212> TYPE: DNA
<213> ORGANISM: Citrobacter amalonaticus

<400> SEQUENCE: 73
tcaatactgc tgtagtgcct gcgcattaat gataagattt gtg                  43

<210> SEQ ID NO 74
<211> LENGTH: 43
<212> TYPE: DNA
<213> ORGANISM: Escherichia albertii

<400> SEQUENCE: 74
tcattcctgc tgtggatttc aggctttaat gataagattt gtg                  43

<210> SEQ ID NO 75
<211> LENGTH: 43
<212> TYPE: DNA

-continued

<213> ORGANISM: Escherichia sp.

<400> SEQUENCE: 75
tcattcctgc tgtggacttc gggctttaat gataagattt gtg                43

<210> SEQ ID NO 76
<211> LENGTH: 43
<212> TYPE: DNA
<213> ORGANISM: Escherichia sp.

<400> SEQUENCE: 76
tcattcgtgc tgtggactgc aggctttaat ggtaagattt gtg                43

<210> SEQ ID NO 77
<211> LENGTH: 43
<212> TYPE: DNA
<213> ORGANISM: Escherichia sp.

<400> SEQUENCE: 77
tcattcgtgc tgtggactgt aggctttaat gataagattt gtg                43

<210> SEQ ID NO 78
<211> LENGTH: 43
<212> TYPE: DNA
<213> ORGANISM: Escherichia sp.

<400> SEQUENCE: 78
tcattcgtgc tgtggactgc aggctttaat gataagattt ttg                43

<210> SEQ ID NO 79
<211> LENGTH: 43
<212> TYPE: DNA
<213> ORGANISM: Escherichia sp.

<400> SEQUENCE: 79
tcattcgtgc tgtggaccgc aggctttaat gataagattt gtg                43

<210> SEQ ID NO 80
<211> LENGTH: 43
<212> TYPE: DNA
<213> ORGANISM: Escherichia sp.

<400> SEQUENCE: 80
tcattcgtgc tgcggactgc aggctttaat gataagattt gtg                43

<210> SEQ ID NO 81
<211> LENGTH: 43
<212> TYPE: DNA
<213> ORGANISM: Escherichia sp.

<400> SEQUENCE: 81
tcattcgtgc tgtggactgc aggctttaat gataatattt gtg                43

<210> SEQ ID NO 82
<211> LENGTH: 43
<212> TYPE: DNA
<213> ORGANISM: Escherichia sp.

<400> SEQUENCE: 82
tcattcgtgc tgtggactgc aggctttaat gataagattt gtg                43

<210> SEQ ID NO 83
<211> LENGTH: 43

<212> TYPE: DNA
<213> ORGANISM: Shigella dysenteriae

<400> SEQUENCE: 83
tcattcatgc tgtgggcttc aggctttaat gataagattt gtg        43

<210> SEQ ID NO 84
<211> LENGTH: 43
<212> TYPE: DNA
<213> ORGANISM: Escherichia sp.

<400> SEQUENCE: 84
tcattcgtgc tgtggagttc aggctttaat gataagattt gtg        43

<210> SEQ ID NO 85
<211> LENGTH: 43
<212> TYPE: DNA
<213> ORGANISM: Escherichia sp.

<400> SEQUENCE: 85
tcattcatgc tgtggacttc aggctttaat gataagattt gtg        43

<210> SEQ ID NO 86
<211> LENGTH: 43
<212> TYPE: DNA
<213> ORGANISM: Escherichia sp.

<400> SEQUENCE: 86
tcattcgtgc tgtggacttc aggctttaat gataaaattt gtg        43

<210> SEQ ID NO 87
<211> LENGTH: 43
<212> TYPE: DNA
<213> ORGANISM: Escherichia sp.

<400> SEQUENCE: 87
tcattcgtgc tgtgggcttc aggctttaat gataagattt gtg        43

<210> SEQ ID NO 88
<211> LENGTH: 43
<212> TYPE: DNA
<213> ORGANISM: Escherichia sp.

<400> SEQUENCE: 88
tcattcgtgc tgtggacttc aggctttaat gataagattt gtg        43

<210> SEQ ID NO 89
<211> LENGTH: 43
<212> TYPE: DNA
<213> ORGANISM: Escherichia sp.

<400> SEQUENCE: 89
tcattcctgc tgtggacttc ggcctttaat gataagattt gtg        43

<210> SEQ ID NO 90
<211> LENGTH: 43
<212> TYPE: DNA
<213> ORGANISM: Escherichia sp.

<400> SEQUENCE: 90
tcattcctgc tgtggacttc aggctttaat gataagattt gtg        43

<210> SEQ ID NO 91

```
<211> LENGTH: 43
<212> TYPE: DNA
<213> ORGANISM: Escherichia sp.

<400> SEQUENCE: 91
tcattcctgc tgtggacttc aggctttaat ggtaagattt gtg          43

<210> SEQ ID NO 92
<211> LENGTH: 43
<212> TYPE: DNA
<213> ORGANISM: Citrobacter freundii

<400> SEQUENCE: 92
tcattactgc tgtggagcgt acgctttaat gataagattc gtg          43

<210> SEQ ID NO 93
<211> LENGTH: 43
<212> TYPE: DNA
<213> ORGANISM: Citrobacter sp.

<400> SEQUENCE: 93
tcattactgc tgtggagcgt acgctttaat ggtaatattt atg          43

<210> SEQ ID NO 94
<211> LENGTH: 43
<212> TYPE: DNA
<213> ORGANISM: Citrobacter freundii

<400> SEQUENCE: 94
tcattactgc tgtggtgcga acgcattaat ggtaagattt gtg          43

<210> SEQ ID NO 95
<211> LENGTH: 43
<212> TYPE: DNA
<213> ORGANISM: Citrobacter koseri

<400> SEQUENCE: 95
tcattactgc tgtagagcgt acgctttaat ggtaagattt gtg          43

<210> SEQ ID NO 96
<211> LENGTH: 43
<212> TYPE: DNA
<213> ORGANISM: Citrobacter sp.

<400> SEQUENCE: 96
tcattactgc tgtagagcgt acgctttaat ggtaatattt gtg          43

<210> SEQ ID NO 97
<211> LENGTH: 43
<212> TYPE: DNA
<213> ORGANISM: Citrobacter youngae

<400> SEQUENCE: 97
tcattactgc tgtggagcgt acgctttaat ggtaatattt gtg          43

<210> SEQ ID NO 98
<211> LENGTH: 43
<212> TYPE: DNA
<213> ORGANISM: Escherichia fergusonii

<400> SEQUENCE: 98
tcattactgc tgtggaatac gggctttaat gataagattt gtt          43
```

```
<210> SEQ ID NO 99
<211> LENGTH: 65
<212> TYPE: DNA
<213> ORGANISM: Bacillus pumilus

<400> SEQUENCE: 99
aaatatggac ctgtcaaact tttggacatg ccgaaaaatt gcatgaaata gaggagcgtt    60
attat                                                               65

<210> SEQ ID NO 100
<211> LENGTH: 69
<212> TYPE: DNA
<213> ORGANISM: Bacillus subtilis

<400> SEQUENCE: 100
atacatgggc tagtaaatta tttatacatg cctgcacatc aggcatgtga agatagagga    60
gcgttataa                                                           69

<210> SEQ ID NO 101
<211> LENGTH: 57
<212> TYPE: DNA
<213> ORGANISM: Bacillus glycinifermentans

<400> SEQUENCE: 101
gaaaattact gtttgcctgg ctaataaaca aggaaattta cagaggagcg ttattct       57

<210> SEQ ID NO 102
<211> LENGTH: 39
<212> TYPE: DNA
<213> ORGANISM: Corynebacterium glutamicum

<400> SEQUENCE: 102
atcatctttc cgtatcgcta tttataagga cgactactc                           39

<210> SEQ ID NO 103
<211> LENGTH: 52
<212> TYPE: DNA
<213> ORGANISM: Citrobacter freundii

<400> SEQUENCE: 103
aatggttttg catttgtaac cccaaacgca gggtatatca ggtggcaata ac            52

<210> SEQ ID NO 104
<211> LENGTH: 46
<212> TYPE: DNA
<213> ORGANISM: Salmonella enterica

<400> SEQUENCE: 104
gttttgattc cgtaagccca tgaagggcat atcaggtggc aatgac                   46

<210> SEQ ID NO 105
<211> LENGTH: 29
<212> TYPE: DNA
<213> ORGANISM: Escherichia albertii

<400> SEQUENCE: 105
acgttgaata cgatcgggat ggcaataac                                      29

<210> SEQ ID NO 106
<211> LENGTH: 37
<212> TYPE: DNA
<213> ORGANISM: Staphylococcus saprophyticus
```

<400> SEQUENCE: 106
gtaagcgaag agttaaaaag ctaaaggagc gaacaga         37

<210> SEQ ID NO 107
<211> LENGTH: 40
<212> TYPE: DNA
<213> ORGANISM: Staphylococcus epidermidis

<400> SEQUENCE: 107
gtaagccaaa cagttttag ttaaaggagc gacgcgtgca         40

<210> SEQ ID NO 108
<211> LENGTH: 50
<212> TYPE: DNA
<213> ORGANISM: Bacillus megaterium

<400> SEQUENCE: 108
gatagttgat ggataaactt gttcacttaa atcaaagggg gaaatgtaat         50

<210> SEQ ID NO 109
<211> LENGTH: 50
<212> TYPE: DNA
<213> ORGANISM: Artificial Sequence
<220> FEATURE:
<223> OTHER INFORMATION: Artificial 5'UTR including a RBS/Shine Dalgarno
      sequence

<400> SEQUENCE: 109
atcaagcaaa gggcaaggtg tcctagtaag gtcgacaagg aggtctaatt         50

<210> SEQ ID NO 110
<211> LENGTH: 75
<212> TYPE: DNA
<213> ORGANISM: Artificial Sequence
<220> FEATURE:
<223> OTHER INFORMATION: Artificial 5'UTR including a RBS/Shine Dalgarno
      sequence

<400> SEQUENCE: 110
agttactagt agcggccgct gcagtccggc aaaaaagggc aaggtgtcct agtaaggtcg         60
acaggaggac tctct         75

<210> SEQ ID NO 111
<211> LENGTH: 48
<212> TYPE: DNA
<213> ORGANISM: Artificial Sequence
<220> FEATURE:
<223> OTHER INFORMATION: Artificial 5'UTR including a RBS/Shine Dalgarno
      sequence

<400> SEQUENCE: 111
gtggaattgt gagcggataa caattcccaa ttaaggagg aaggatca         48

<210> SEQ ID NO 112
<211> LENGTH: 42
<212> TYPE: DNA
<213> ORGANISM: Artificial Sequence
<220> FEATURE:
<223> OTHER INFORMATION: Artificial 5'UTR including a RBS/Shine Dalgarno
      sequence

<400> SEQUENCE: 112
aattgtgagc ggataacaat taagcttaag gaggtgtatc ta         42

```
<210> SEQ ID NO 113
<211> LENGTH: 25
<212> TYPE: DNA
<213> ORGANISM: Artificial Sequence
<220> FEATURE:
<223> OTHER INFORMATION: Artificial 5'UTR including a RBS/Shine Dalgarno
      sequence

<400> SEQUENCE: 113
actagagaaa ggtggtgaat actag                                            25

<210> SEQ ID NO 114
<211> LENGTH: 47
<212> TYPE: DNA
<213> ORGANISM: Artificial Sequence
<220> FEATURE:
<223> OTHER INFORMATION: Artificial 5'UTR including a RBS/Shine Dalgarno
      sequence

<400> SEQUENCE: 114
aatttgaaaa ttatgtatta tgtgaataaa gaggaggaga gtgagat                    47

<210> SEQ ID NO 115
<211> LENGTH: 23
<212> TYPE: DNA
<213> ORGANISM: Artificial Sequence
<220> FEATURE:
<223> OTHER INFORMATION: Artificial 5'UTR including a RBS/Shine Dalgarno
      sequence

<400> SEQUENCE: 115
aaaattagct aggggaata att                                               23

<210> SEQ ID NO 116
<211> LENGTH: 45
<212> TYPE: DNA
<213> ORGANISM: Artificial Sequence
<220> FEATURE:
<223> OTHER INFORMATION: Artificial 5'UTR including a RBS/Shine Dalgarno
      sequence

<400> SEQUENCE: 116
aacggcattg ctagacggtt acaagaagga ggacgaataa ttata                      45

<210> SEQ ID NO 117
<211> LENGTH: 44
<212> TYPE: DNA
<213> ORGANISM: Artificial Sequence
<220> FEATURE:
<223> OTHER INFORMATION: Consensus sequence for SecA promoter from
      Bacillus
<220> FEATURE:
<221> NAME/KEY: unsure
<222> LOCATION: (2)..(2)
<223> OTHER INFORMATION: All occurrences of k indicate one of the
      following nucleotides: G, T
<220> FEATURE:
<221> NAME/KEY: unsure
<222> LOCATION: (3)..(3)
<223> OTHER INFORMATION: All occurrences of n indicate one of the
      following nucleotides: A, C, G, T
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: unsure
<222> LOCATION: (13)..(24)
<223> OTHER INFORMATION: All occurrences of n indicate one of the
      following nucleotides: A, C, G, T; this sequence segment can be
      from 8 to 12 nucleotides long
```

```
<220> FEATURE:
<221> NAME/KEY: misc_feature
<222> LOCATION: (13)..(24)
<223> OTHER INFORMATION: n is a, c, g, or t
<220> FEATURE:
<221> NAME/KEY: unsure
<222> LOCATION: (25)..(25)
<223> OTHER INFORMATION: All occurrences of r indicate one of the
      following nucleotides: A, G
<220> FEATURE:
<221> NAME/KEY: unsure
<222> LOCATION: (27)..(27)
<223> OTHER INFORMATION: All occurrences of r indicate one of the
      following nucleotides: A, G
<220> FEATURE:
<221> NAME/KEY: unsure
<222> LOCATION: (30)..(30)
<223> OTHER INFORMATION: All occurrences of n indicate one of the
      following nucleotides: A, C, G, T
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: unsure
<222> LOCATION: (33)..(33)
<223> OTHER INFORMATION: All occurrences of w indicate one of the
      following nucleotides: A, T
<220> FEATURE:
<221> NAME/KEY: unsure
<222> LOCATION: (34)..(34)
<223> OTHER INFORMATION: All occurrences of r indicate one of the
      following nucleotides: A, G
<220> FEATURE:
<221> NAME/KEY: unsure
<222> LOCATION: (38)..(38)
<223> OTHER INFORMATION: All occurrences of w indicate one of the
      following nucleotides: A, T
<220> FEATURE:
<221> NAME/KEY: unsure
<222> LOCATION: (39)..(44)
<223> OTHER INFORMATION: All occurrences of n indicate one of the
      following nucleotides: A, C, G, T; this sequence segment can be
      from 4 to 6 nucleotides long
<220> FEATURE:
<221> NAME/KEY: misc_feature
<222> LOCATION: (39)..(44)
<223> OTHER INFORMATION: n is a, c, g, or t

<400> SEQUENCE: 117
tkntttggaa atnnnnnnnn nnnnrtrtgn tawratawnn nnnn                    44

<210> SEQ ID NO 118
<211> LENGTH: 48
<212> TYPE: DNA
<213> ORGANISM: Artificial Sequence
<220> FEATURE:
<223> OTHER INFORMATION: Consensus sequence for SecA promoter from
      Enterobacter
<220> FEATURE:
<221> NAME/KEY: unsure
<222> LOCATION: (4)..(4)
<223> OTHER INFORMATION: All occurrences of w indicate one of the
      following nucleotides: A, T
<220> FEATURE:
<221> NAME/KEY: unsure
<222> LOCATION: (6)..(6)
<223> OTHER INFORMATION: All occurrences of m indicate one of the
      following nucleotides: A, C
<220> FEATURE:
<221> NAME/KEY: unsure
<222> LOCATION: (7)..(7)
<223> OTHER INFORMATION: All occurrences of n indicate one of the
      following nucleotides: A, C, G, T
<220> FEATURE:
<221> NAME/KEY: misc_feature
<222> LOCATION: (7)..(7)
```

```
<223> OTHER INFORMATION: n is a, c, g, or t
<220> FEATURE:
<221> NAME/KEY: unsure
<222> LOCATION: (13)..(13)
<223> OTHER INFORMATION: All occurrences of y indicate one of the
      following nucleotides: C, T
<220> FEATURE:
<221> NAME/KEY: unsure
<222> LOCATION: (14)..(26)
<223> OTHER INFORMATION: All occurrences of n indicate one of the
      following nucleotides: A, C, G, T; this sequence segment can be
      from 11 to 13 nucleotides long
<220> FEATURE:
<221> NAME/KEY: misc_feature
<222> LOCATION: (14)..(26)
<223> OTHER INFORMATION: n is a, c, g, or t
<220> FEATURE:
<221> NAME/KEY: unsure
<222> LOCATION: (33)..(33)
<223> OTHER INFORMATION: All occurrences of r indicate one of the
      following nucleotides: A, G
<220> FEATURE:
<221> NAME/KEY: unsure
<222> LOCATION: (37)..(37)
<223> OTHER INFORMATION: All occurrences of d indicate one of the
      following nucleotides: A, G, T
<220> FEATURE:
<221> NAME/KEY: unsure
<222> LOCATION: (41)..(41)
<223> OTHER INFORMATION: All occurrences of y indicate one of the
      following nucleotides: C, T
<220> FEATURE:
<221> NAME/KEY: unsure
<222> LOCATION: (42)..(42)
<223> OTHER INFORMATION: All occurrences of d indicate one of the
      following nucleotides: A, G, T
<220> FEATURE:
<221> NAME/KEY: unsure
<222> LOCATION: (44)..(48)
<223> OTHER INFORMATION: All occurrences of n indicate one of the
      following nucleotides: A, C, G, T; this sequence segment can be
      from 4 to 5 nucleotides long
<220> FEATURE:
<221> NAME/KEY: misc_feature
<222> LOCATION: (44)..(48)
<223> OTHER INFORMATION: n is a, c, g, or t

<400> SEQUENCE: 118
tcawtmntgc tgynnnnnnn nnnnnnttaa tgrtaadatt ydtnnnnn                    48
```